(12) United States Patent
Tharp et al.

(10) Patent No.: US 11,185,672 B2
(45) Date of Patent: Nov. 30, 2021

(54) NEEDLING DEVICE AND DRUG APPLICATOR

(71) Applicant: Follica, Inc., Boston, MA (US)

(72) Inventors: David C. Tharp, Boston, MA (US); Scott Kellogg, Mattapoisett, MA (US); Daniel DeRuntz, Somerville, MA (US); Jason Robinson, Tewksbury, MA (US); Greg Wolos, Cambridge, MA (US); Alex Staudt, Cambridge, MA (US); David Chastain, Boston, MA (US); Daniel P. Smith, Portsmouth, RI (US); Justin David Morse, Cranston, RI (US); Anthony Vincent Dibella, Franklin, MA (US); Joseph Gordon, Mansfield, MA (US); Nathan Rollins, Boylston, MA (US)

(*) Notice: Subject to any disclaimer, the term of this patent is extended or adjusted under 35 U.S.C. 154(b) by 102 days.

(21) Appl. No.: 15/763,682

(22) PCT Filed: Sep. 27, 2016

(86) PCT No.: PCT/US2016/053972
§ 371 (c)(1),
(2) Date: Mar. 27, 2018

(87) PCT Pub. No.: WO2017/054009
PCT Pub. Date: Mar. 30, 2017

(65) Prior Publication Data
US 2018/0280675 A1    Oct. 4, 2018

Related U.S. Application Data

(60) Provisional application No. 62/233,373, filed on Sep. 27, 2015.

(51) Int. Cl.
*A61M 37/00* (2006.01)
*A61M 35/00* (2006.01)
(Continued)

(52) U.S. Cl.
CPC ........ *A61M 37/0015* (2013.01); *A61B 17/20* (2013.01); *A61B 17/205* (2013.01);
(Continued)

(58) Field of Classification Search
CPC .. A61M 37/0015; A61M 35/003; A61M 5/32; A61M 2037/0023;
(Continued)

(56) References Cited

U.S. PATENT DOCUMENTS 9,132,058 B2  9/2015  Imboden et al.
9,636,491 B1  5/2017  O'Brien et al.
(Continued)

FOREIGN PATENT DOCUMENTS

CA  3 049 932  7/2018
GB  2518021  3/2005
(Continued)

OTHER PUBLICATIONS

International Search Report dated Mar. 10, 2021 for PCT/US2020/063194 (3 pages).
(Continued)

*Primary Examiner* — Bhisma Mehta
*Assistant Examiner* — Rachel T. Smith
(74) *Attorney, Agent, or Firm* — Jones Day

(57) ABSTRACT

A needling device may be used for needling of a subject's skin, and a drug applicator device may be used for applying a drug to a subject's skin. For example, a needling device may be applied to a subject's skin for hair growth applications, or may be used for wrinkle, scar, or tattoo removal. A drug applicator device may be used for multiple drug application purposes such as applying a hair growth compound to the skin of a subject.

20 Claims, 42 Drawing Sheets

(51) Int. Cl.
  *A61B 17/20* (2006.01)
  *A61M 5/32* (2006.01)
  *A61B 17/00* (2006.01)
  *A61B 90/30* (2016.01)
  *A61B 90/00* (2016.01)

(52) U.S. Cl.
  CPC ............ *A61M 5/32* (2013.01); *A61M 35/003* (2013.01); *A61B 90/30* (2016.02); *A61B 2017/00398* (2013.01); *A61B 2017/00734* (2013.01); *A61B 2017/00747* (2013.01); *A61B 2017/00752* (2013.01); *A61B 2017/00761* (2013.01); *A61B 2017/00769* (2013.01); *A61B 2090/0813* (2016.02); *A61H 2205/021* (2013.01); *A61M 2037/0023* (2013.01)

(58) Field of Classification Search
  CPC ........ A61M 2037/0061; A61M 5/3295; A61M 5/3202; A61M 5/158; A61M 5/3298; A61M 5/46; A61B 17/205; A61B 17/20; A61B 2090/0813; A61B 2017/00398; A61B 2017/00734; A61B 2017/00747; A61B 90/30; A61B 2017/00769; A61B 2017/00752; A61B 2017/00761; A61H 2205/021
  See application file for complete search history.

(56) References Cited

U.S. PATENT DOCUMENTS

| | | | |
|---|---|---|---|
| 2002/0120261 A1 | 8/2002 | Morris et al. | |
| 2006/0253079 A1* | 11/2006 | McDonough | A61M 37/0015 604/173 |
| 2007/0270738 A1 | 11/2007 | Wu et al. | |
| 2008/0221548 A1 | 9/2008 | Danenberg et al. | |
| 2009/0032049 A1 | 2/2009 | Rabin et al. | |
| 2010/0023003 A1 | 1/2010 | Mulholland | |
| 2010/0036317 A1* | 2/2010 | Oginski | A61M 37/00 604/131 |
| 2011/0144631 A1 | 6/2011 | Elkins et al. | |
| 2012/0158100 A1 | 6/2012 | Schomacker | |
| 2014/0128685 A1* | 5/2014 | Na | A61M 37/00 600/249 |
| 2014/0330196 A1* | 11/2014 | Ingman | A61N 1/322 604/21 |
| 2017/0224935 A1* | 8/2017 | Hoffmann | A61M 5/44 |

FOREIGN PATENT DOCUMENTS

| | | |
|---|---|---|
| KR | 10-2009-0073716 | 7/2009 |
| WO | WO 2012/140354 | 10/2002 |

OTHER PUBLICATIONS

International Search Report dated Feb. 27, 2017 in connection of PCT Application No. PCT/US2016/053972 filed Sep. 27, 2016.
Written Opinion dated Feb. 27, 2017 in connection of PCT Application No. PCT/US2016/053972 filed Sep. 27, 2016.
Office Action dated Aug. 11, 2020 issued in Japanese Patent Application No. 2018-515792 (7 pages; English translation).

* cited by examiner

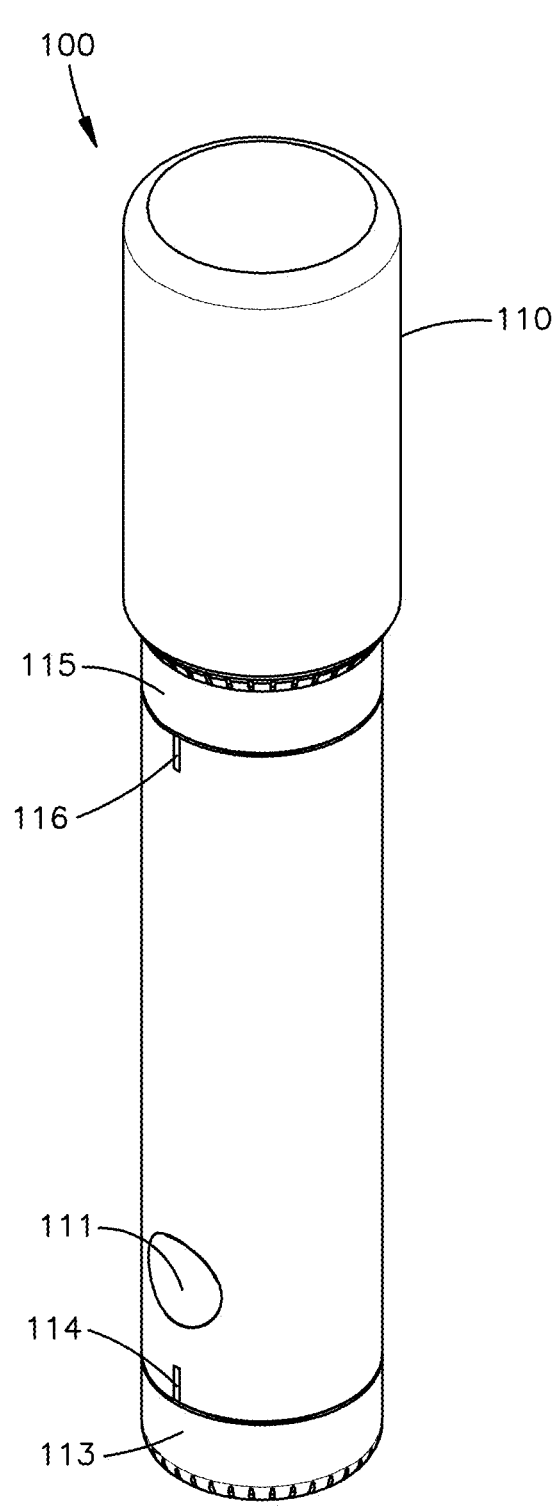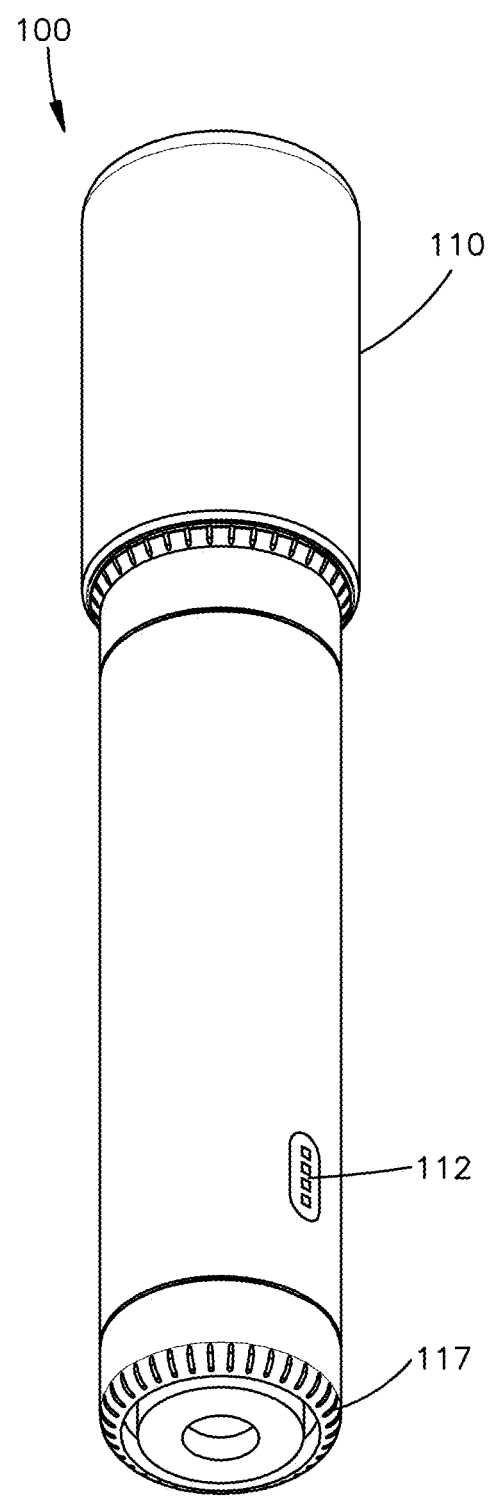

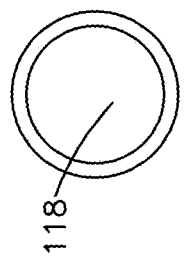
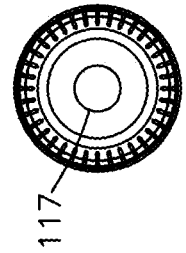
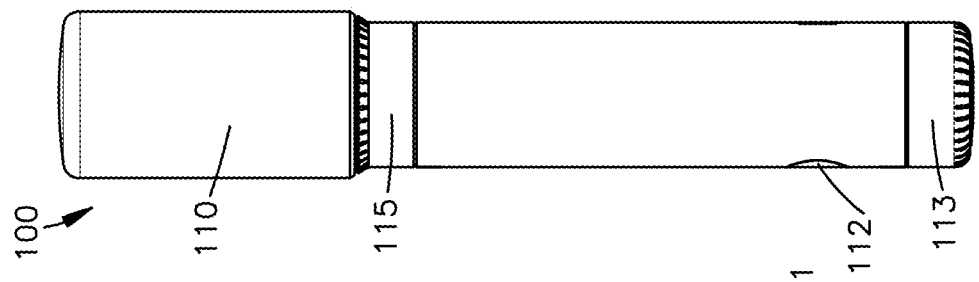
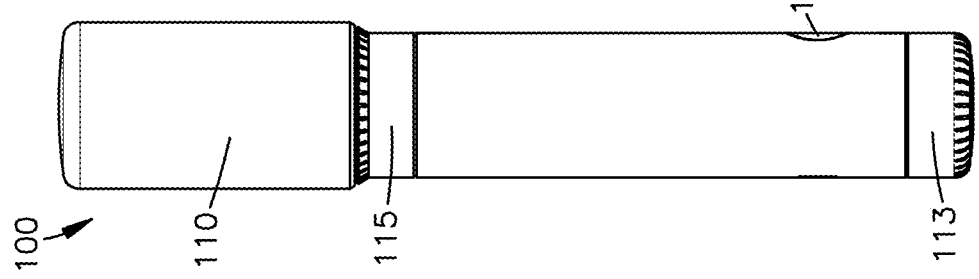
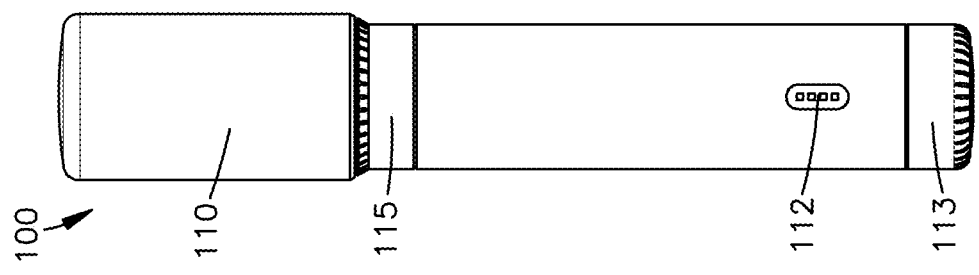
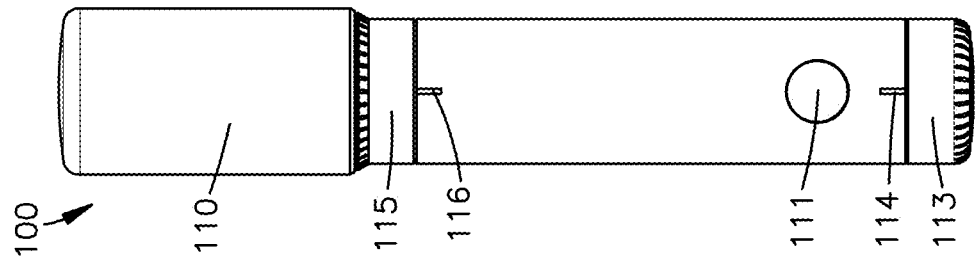

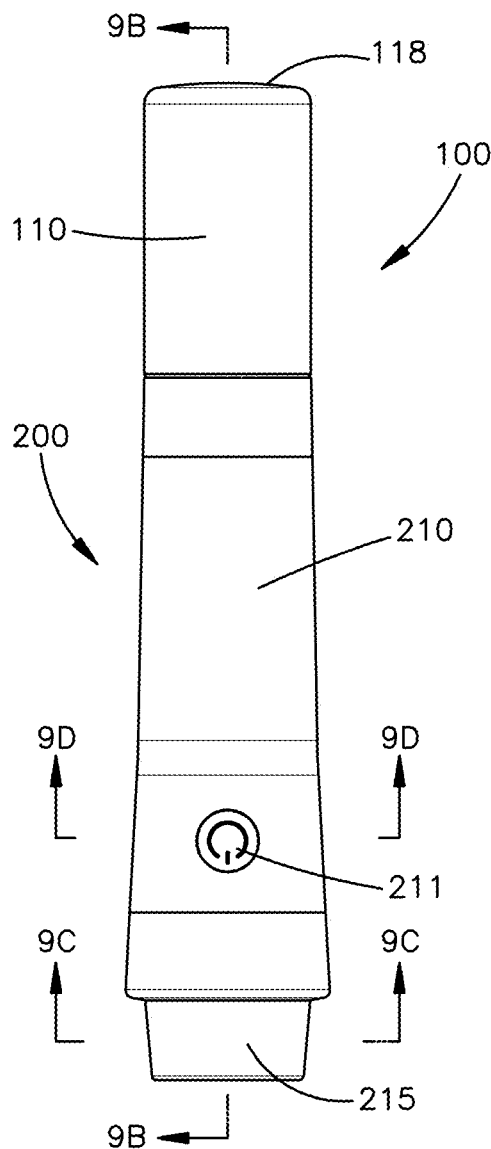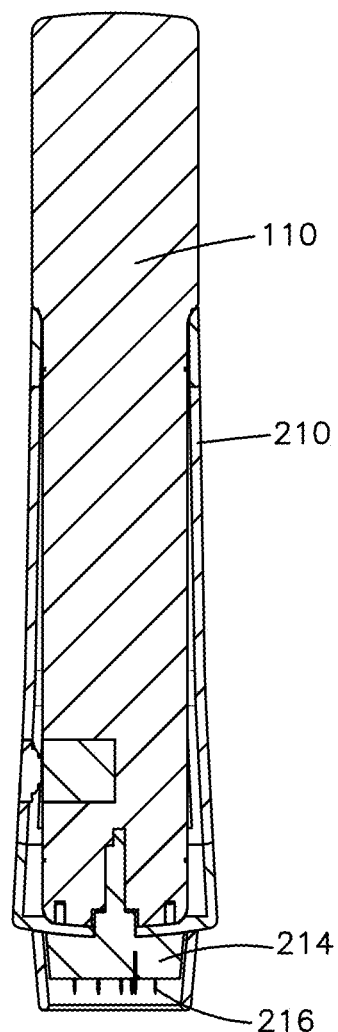
Fig.9A  Fig.9B
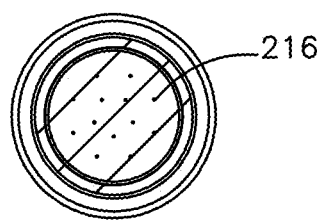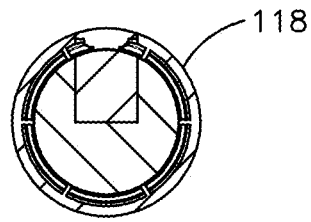
Fig.9C  Fig.9D

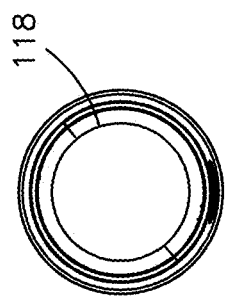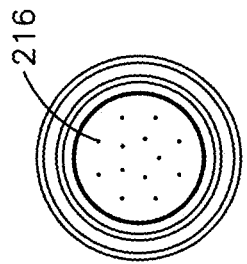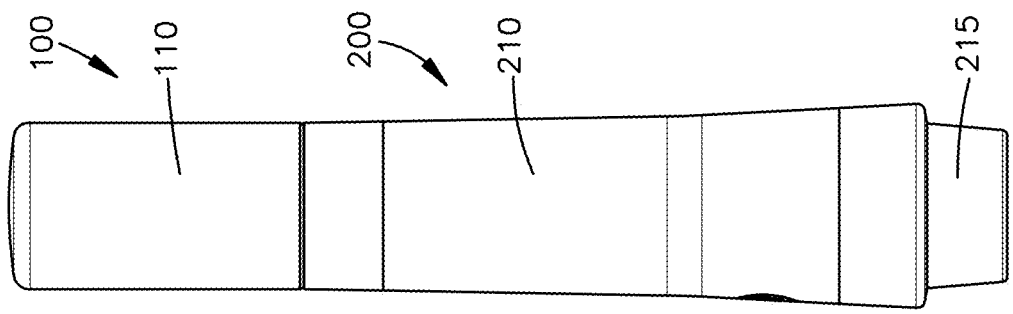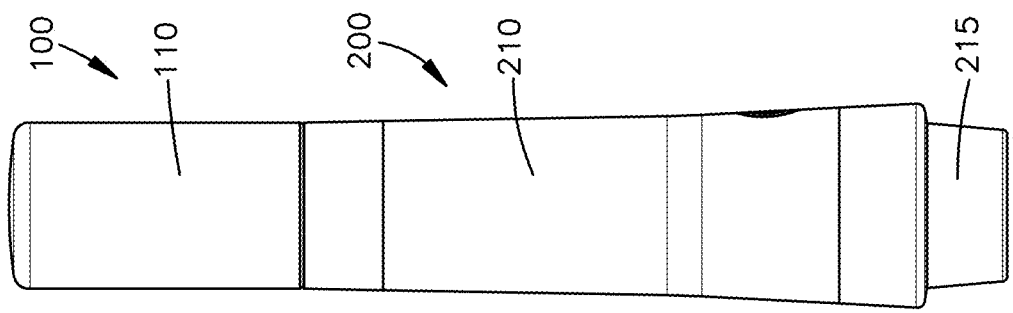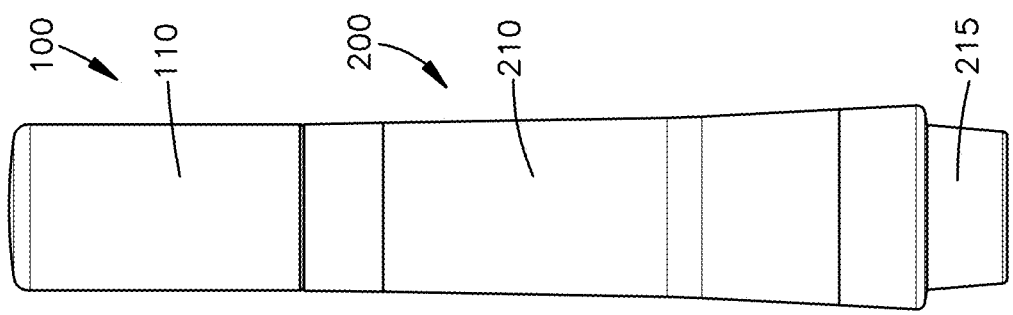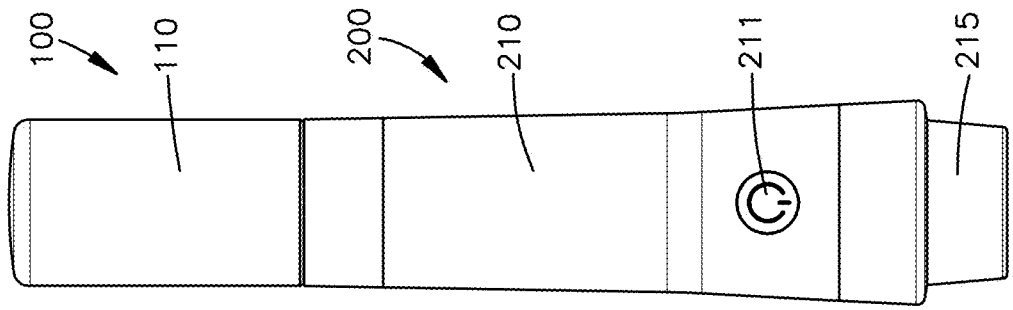

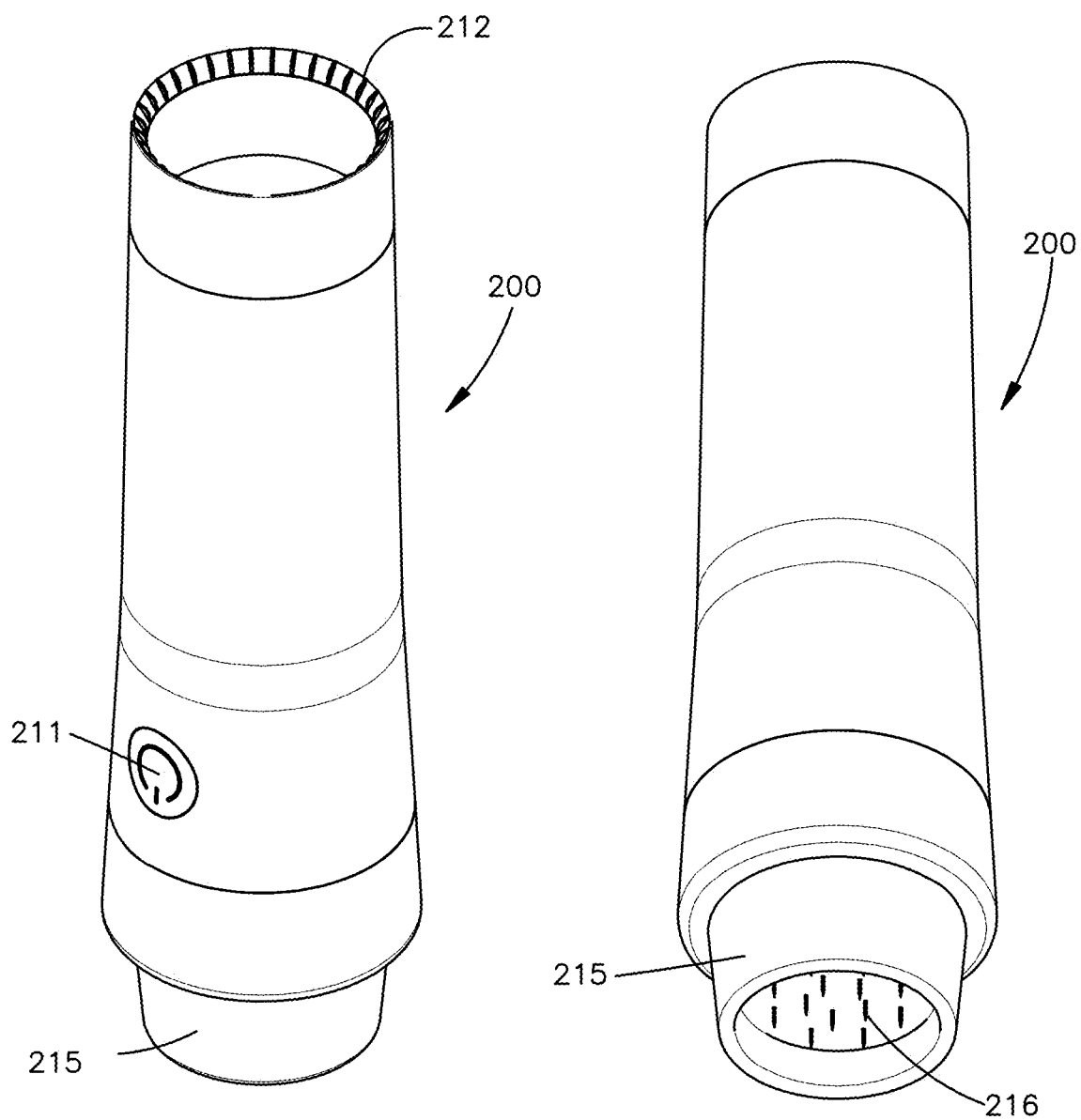

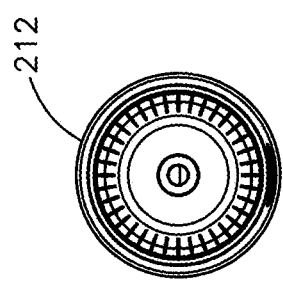
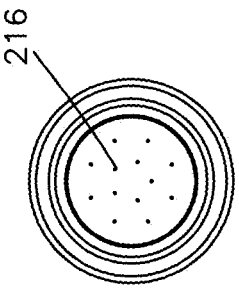
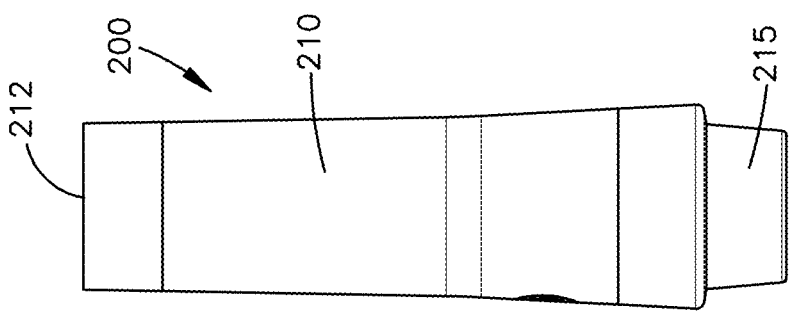
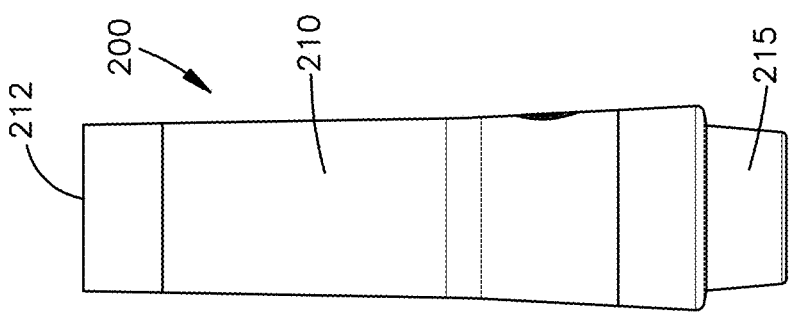
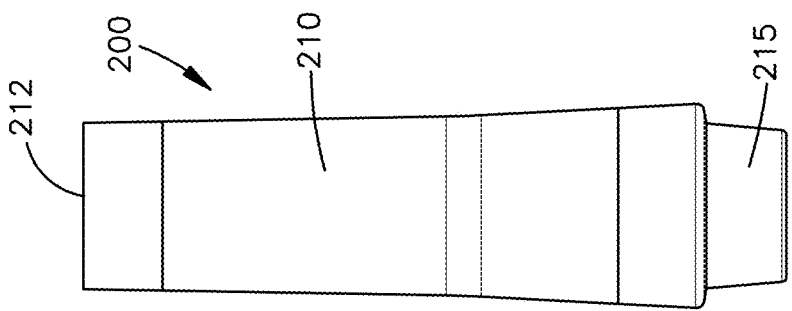
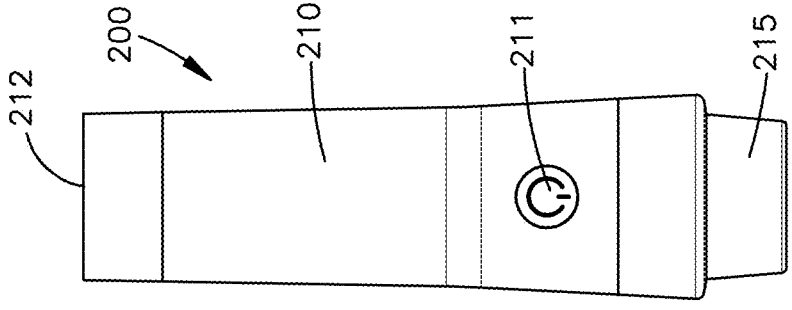

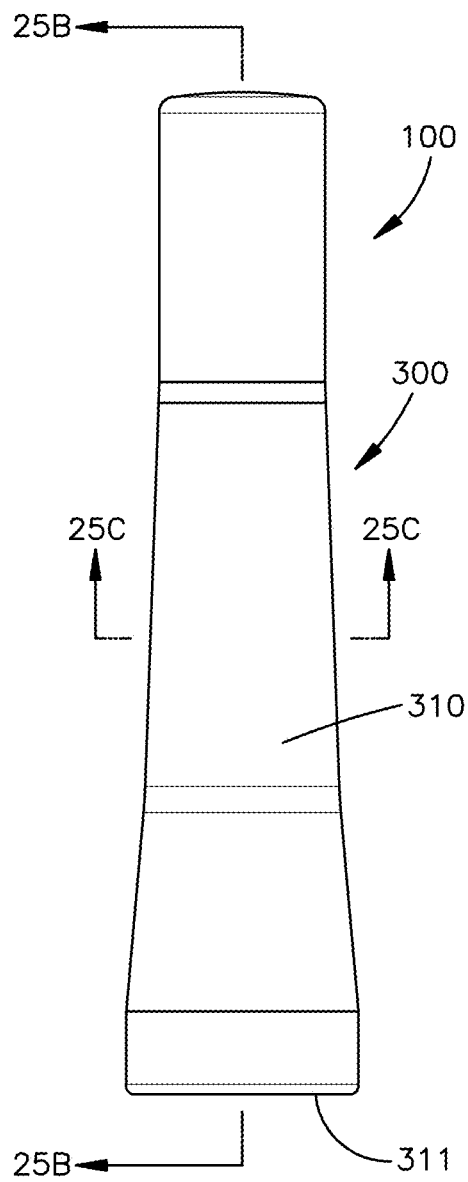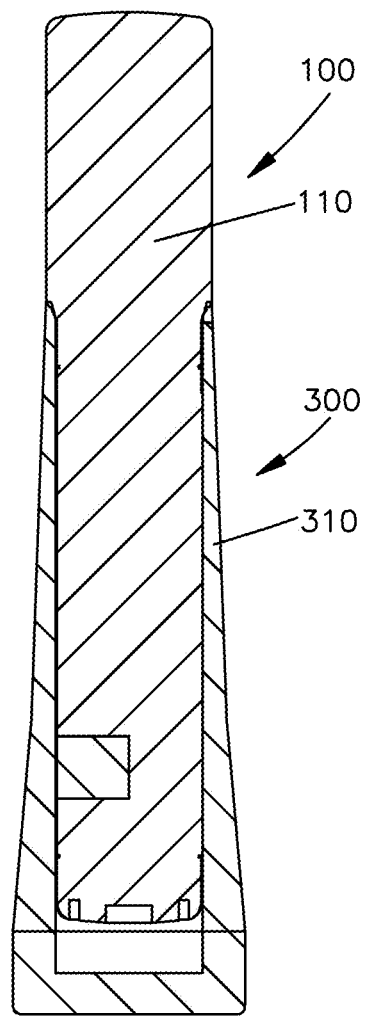
Fig.25A  Fig.25B
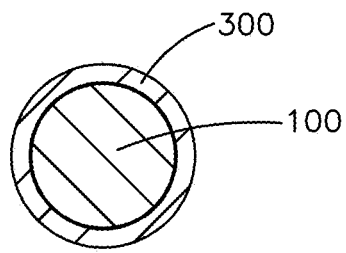
Fig.25C

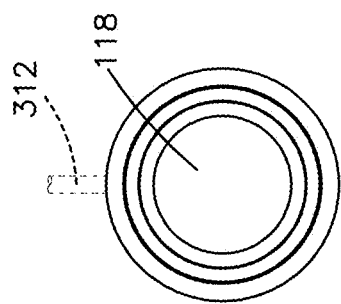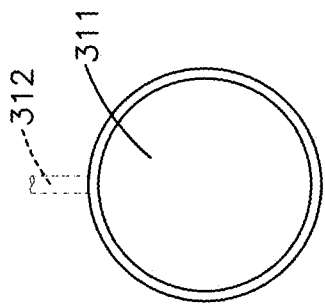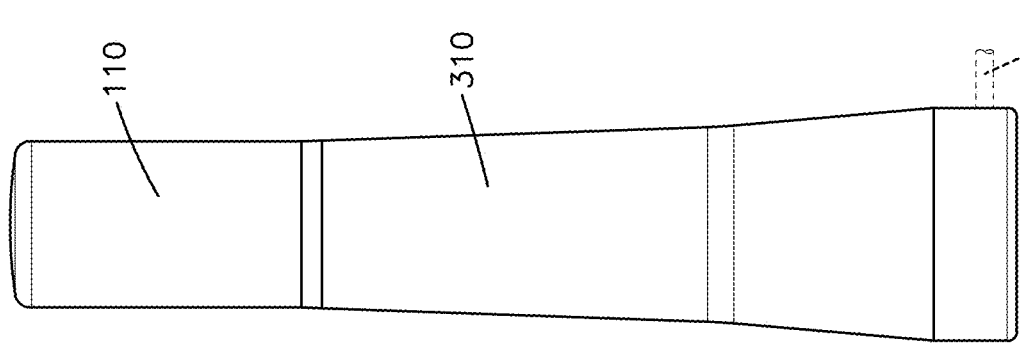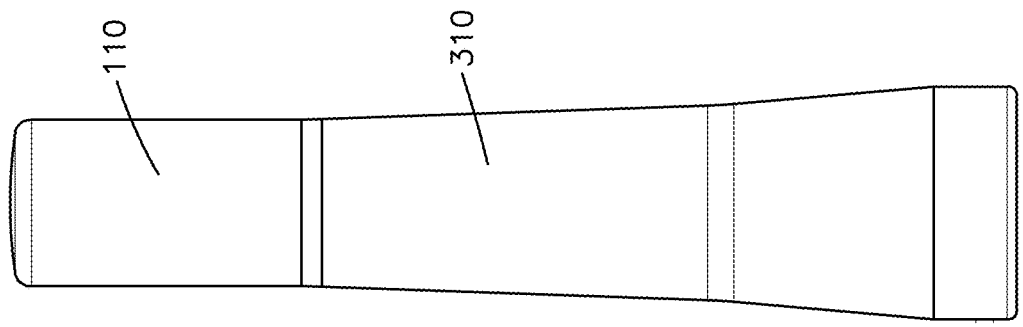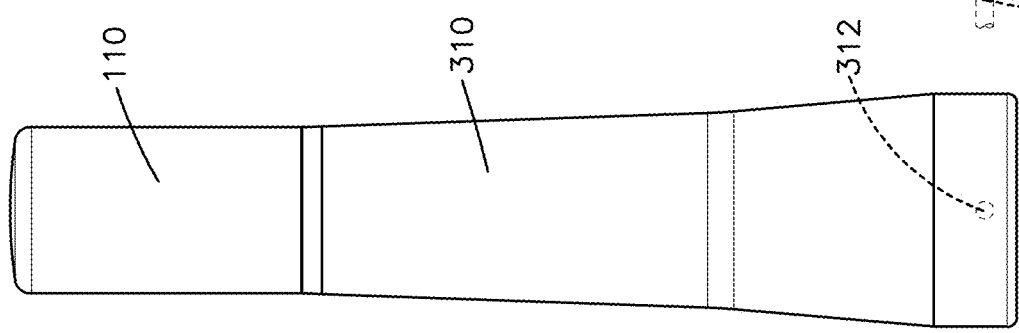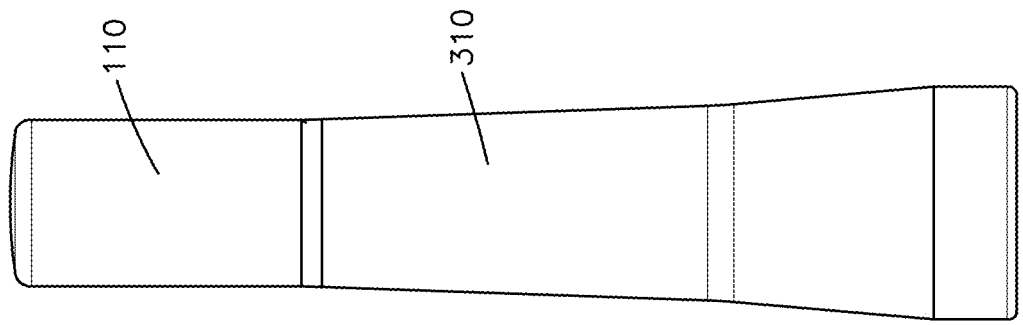

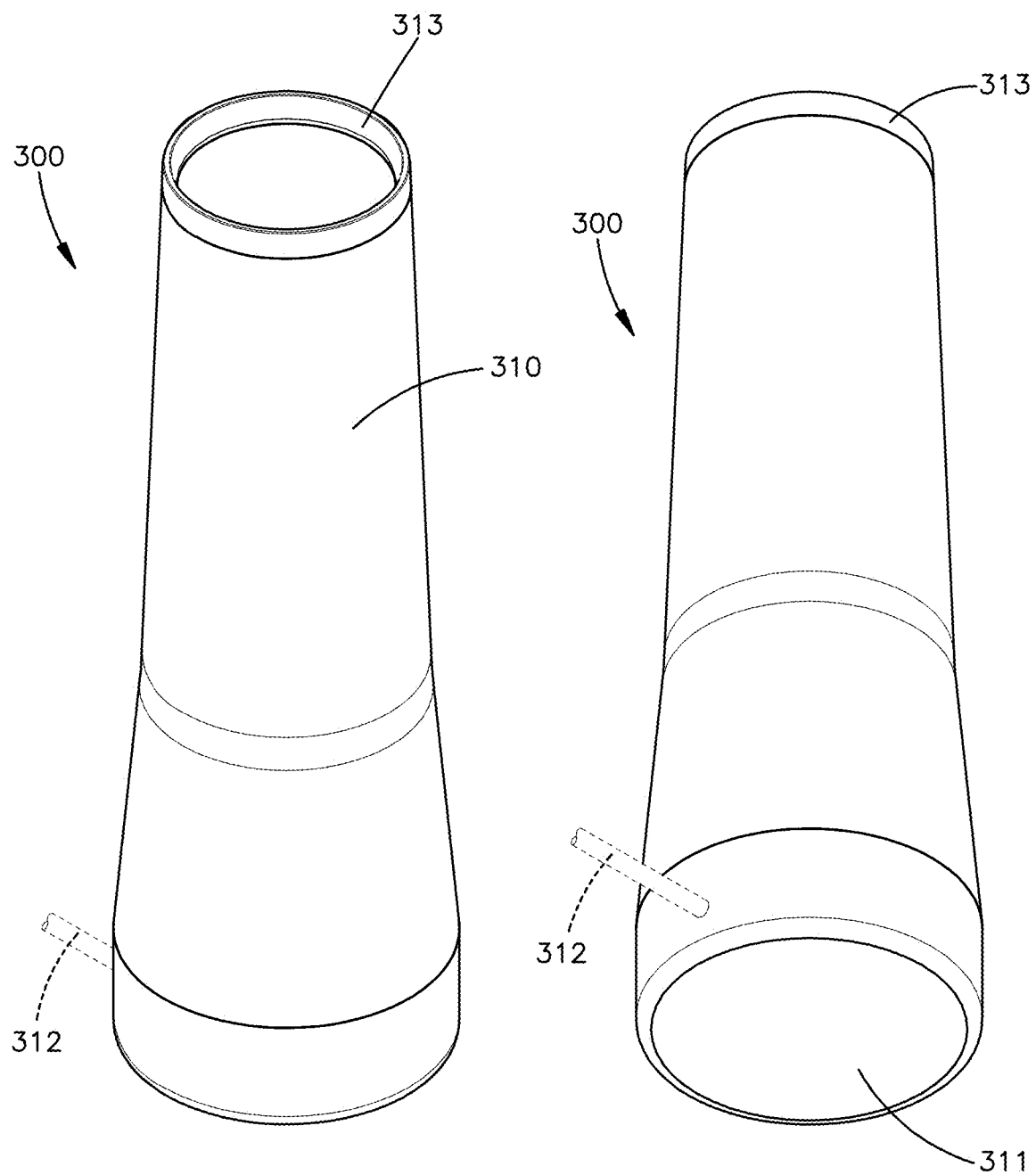

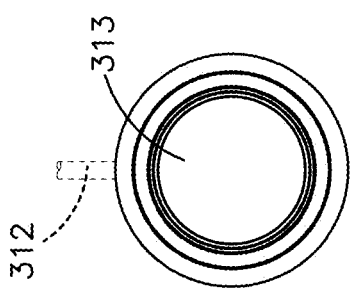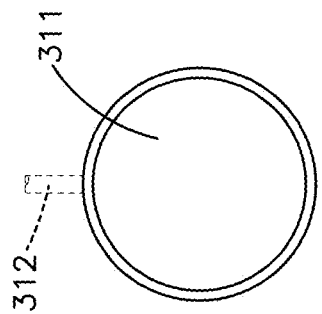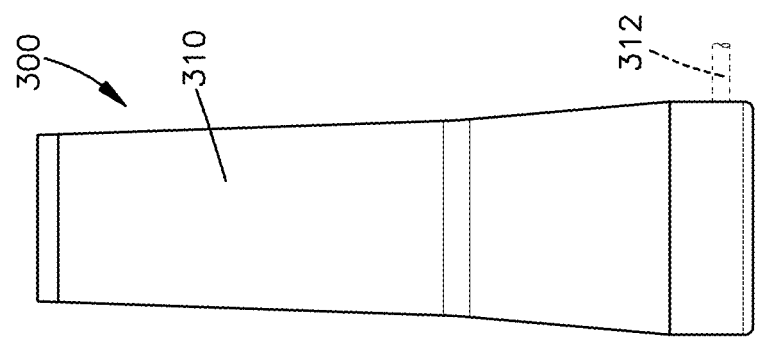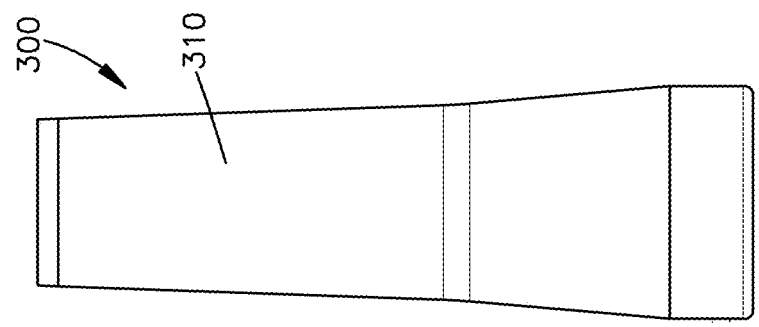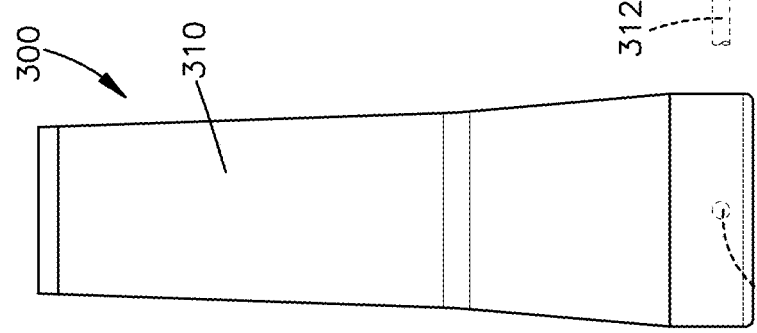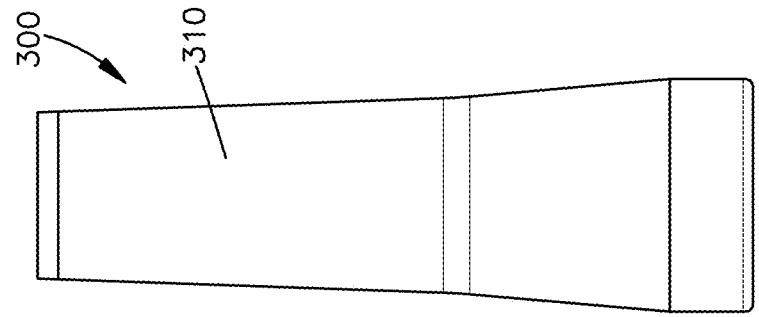

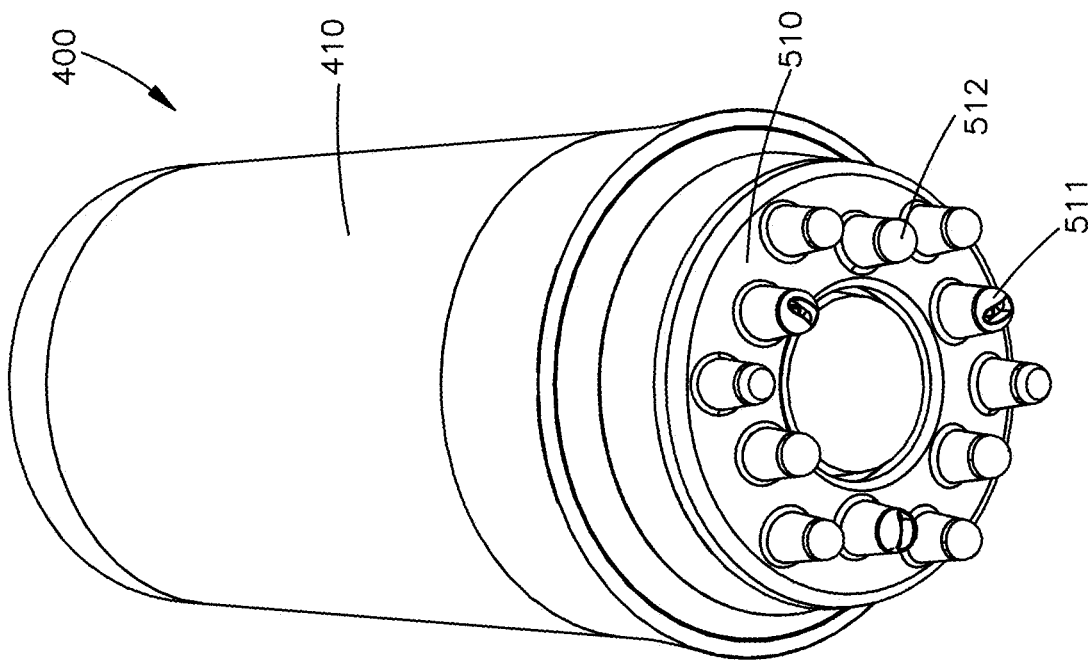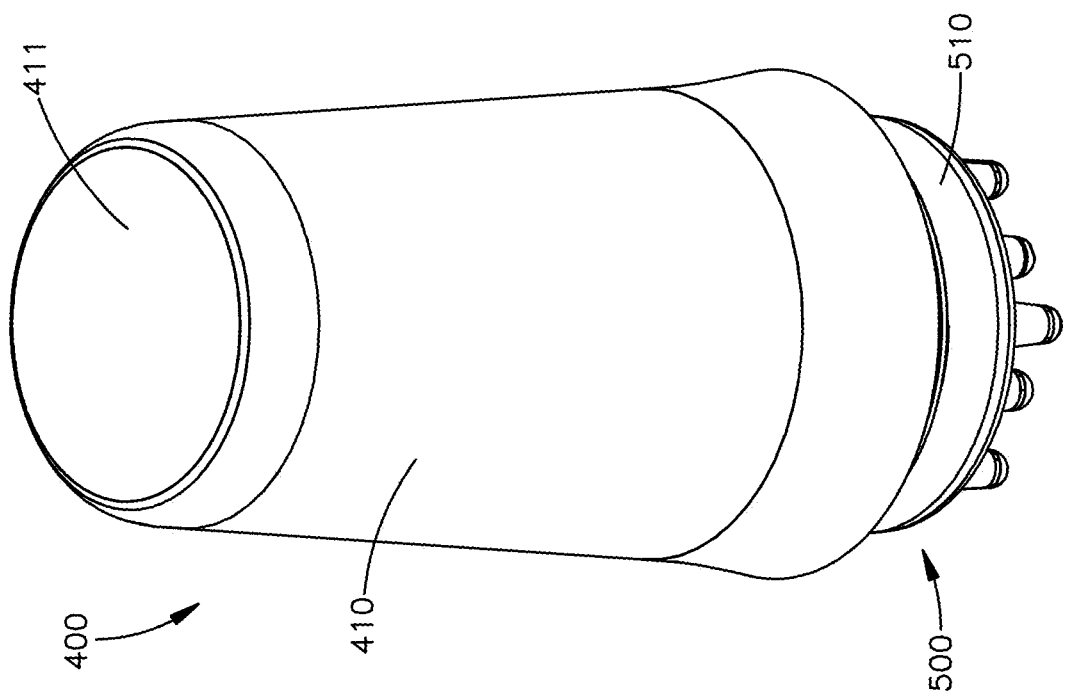

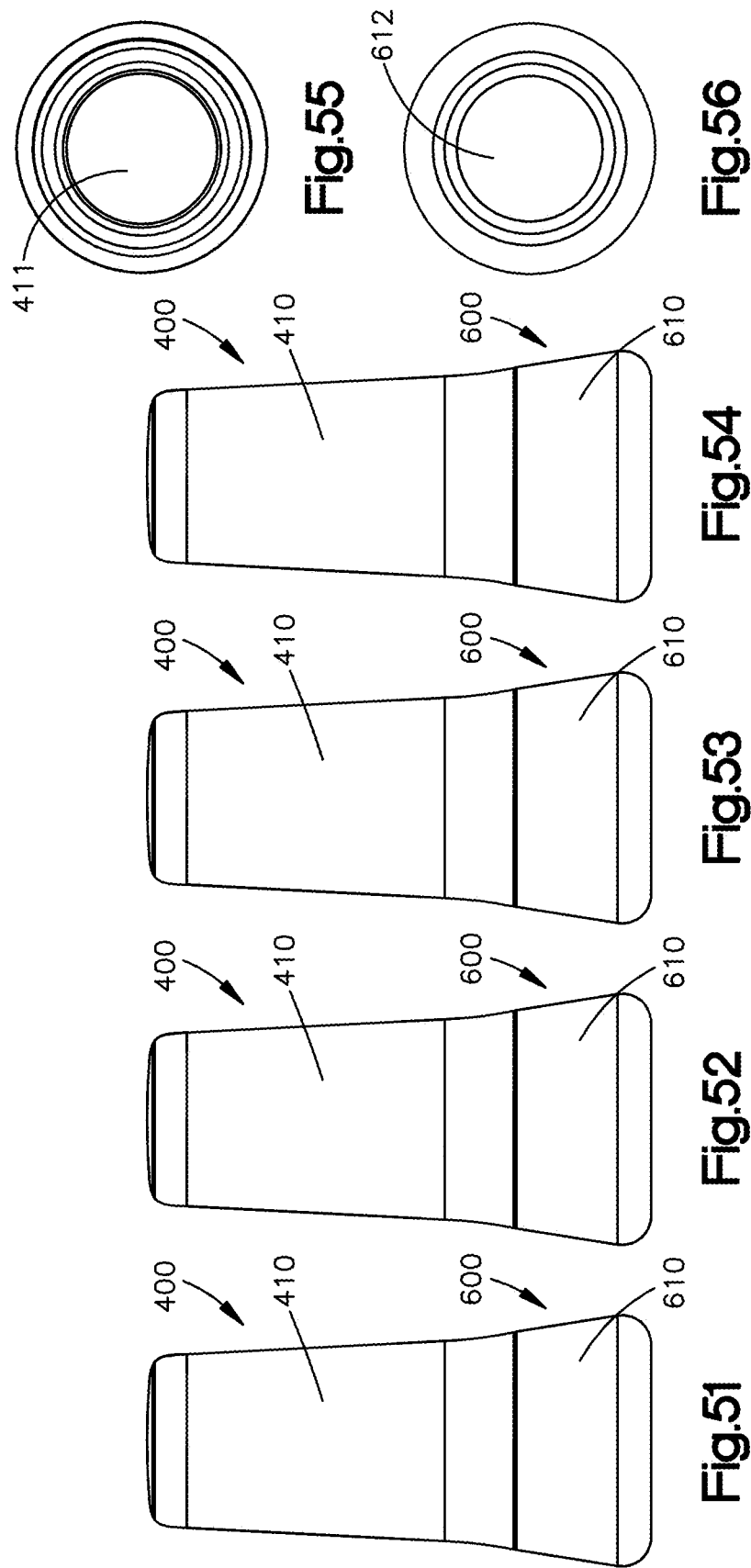

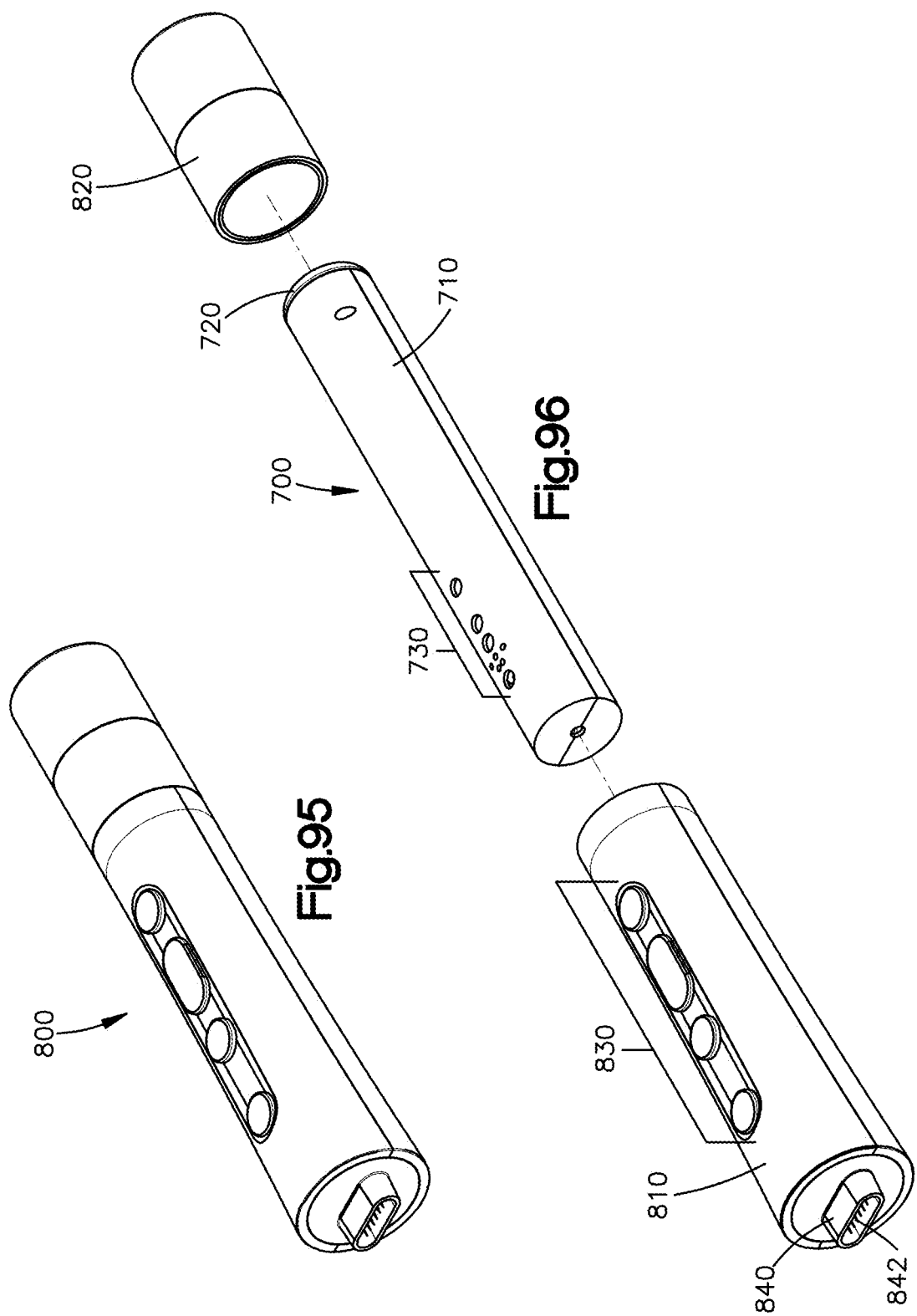

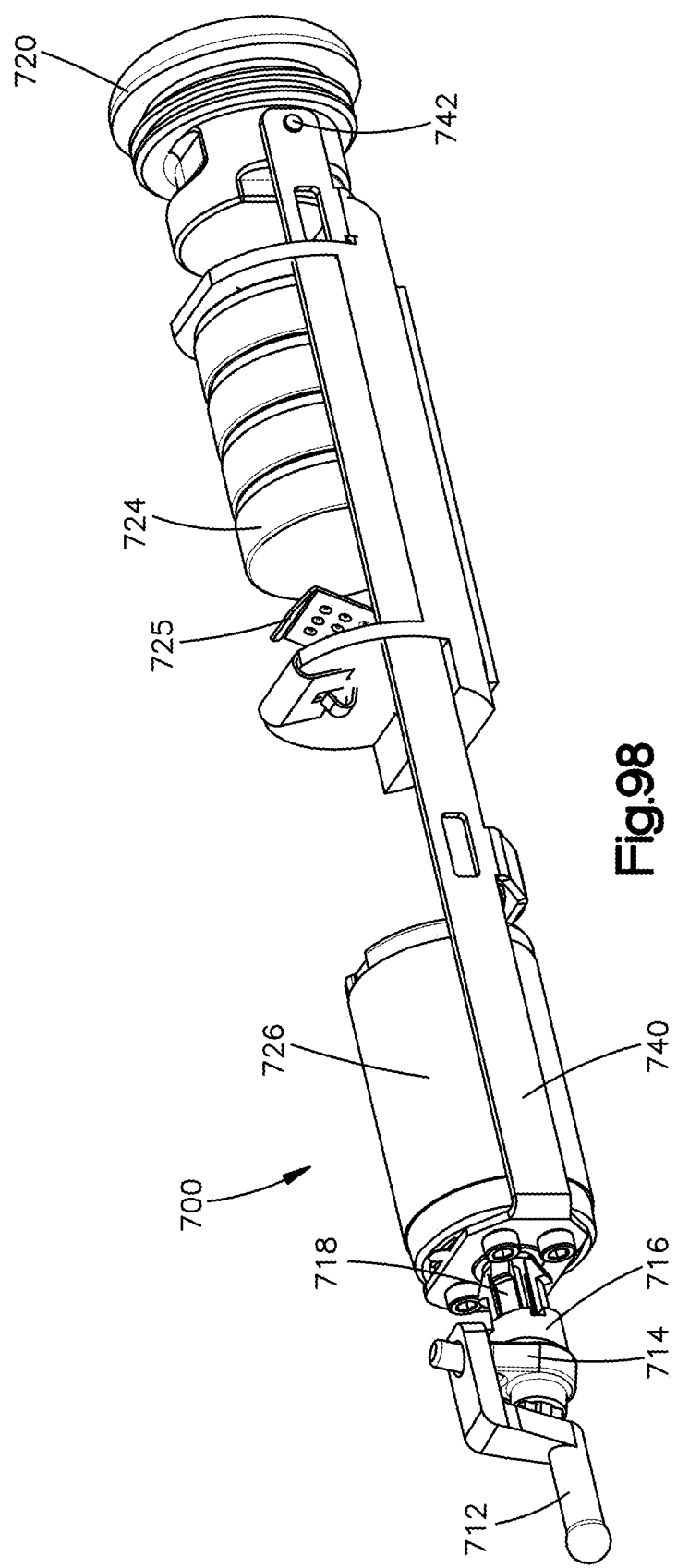

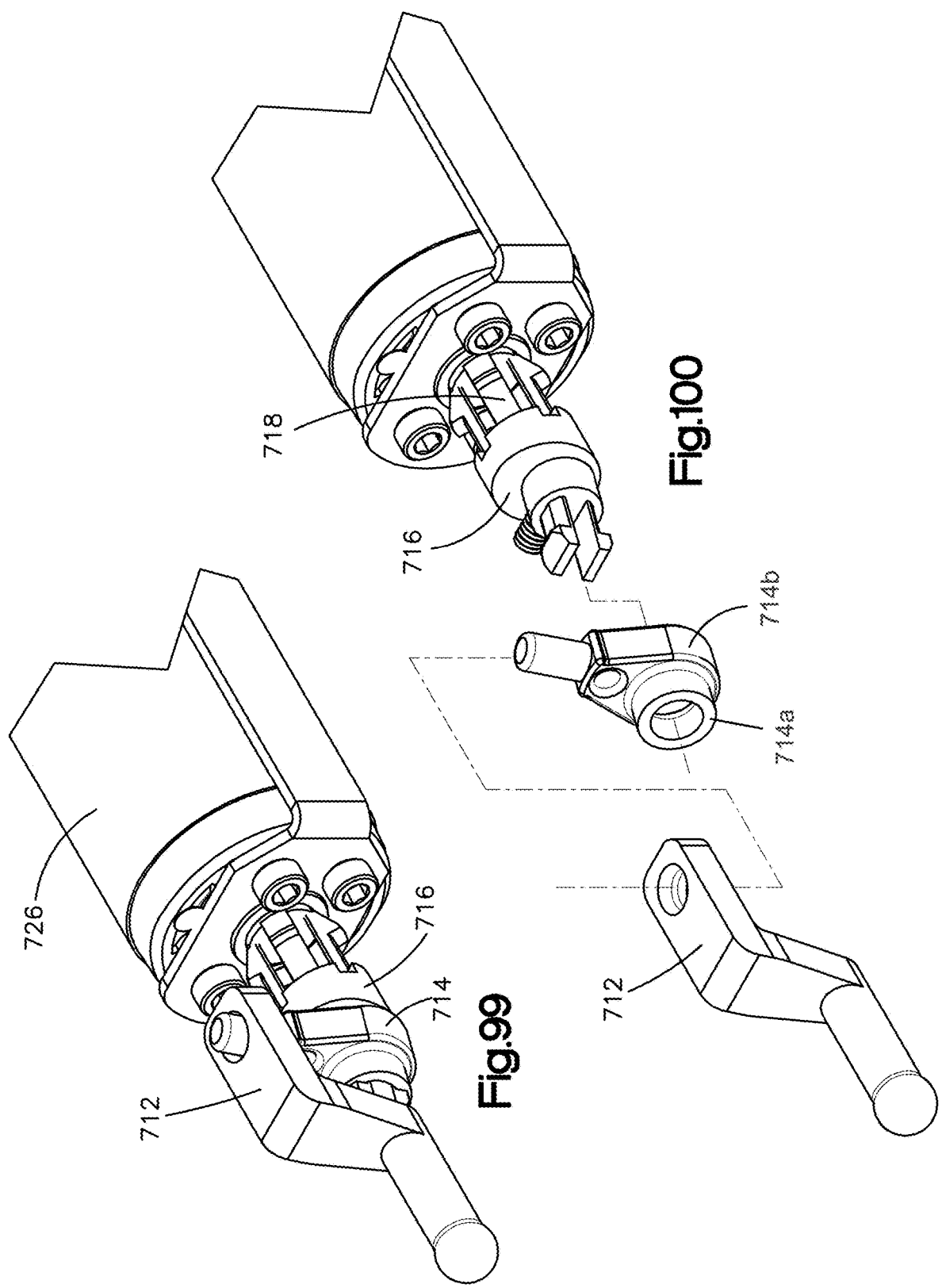

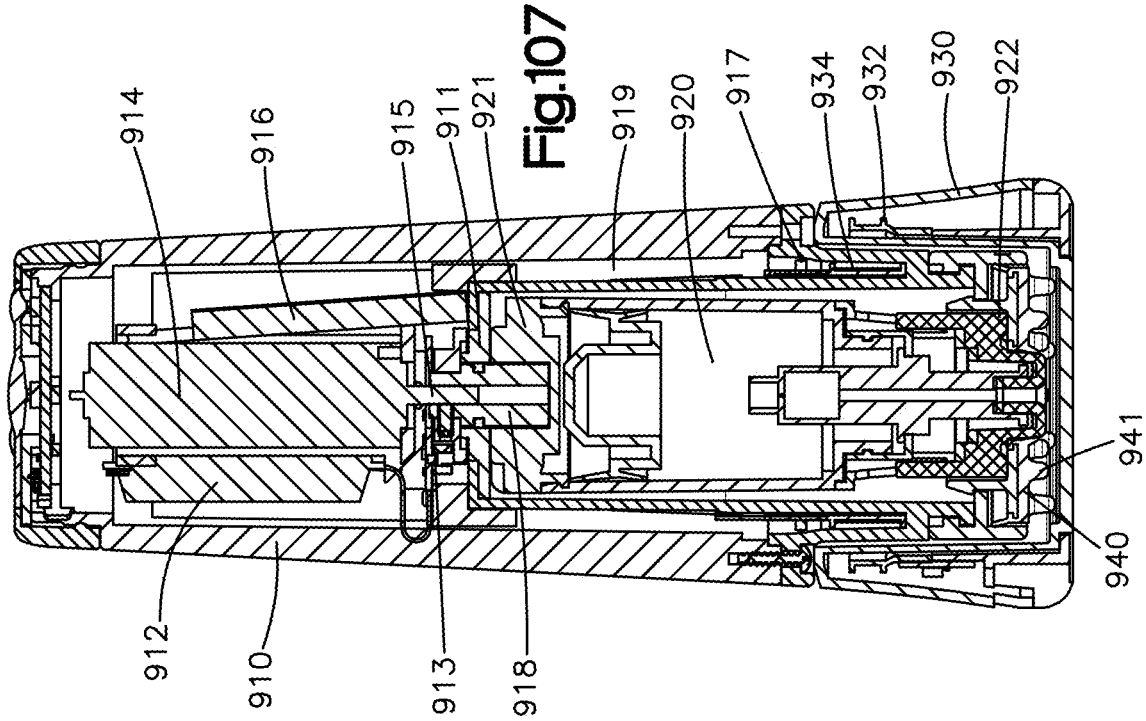
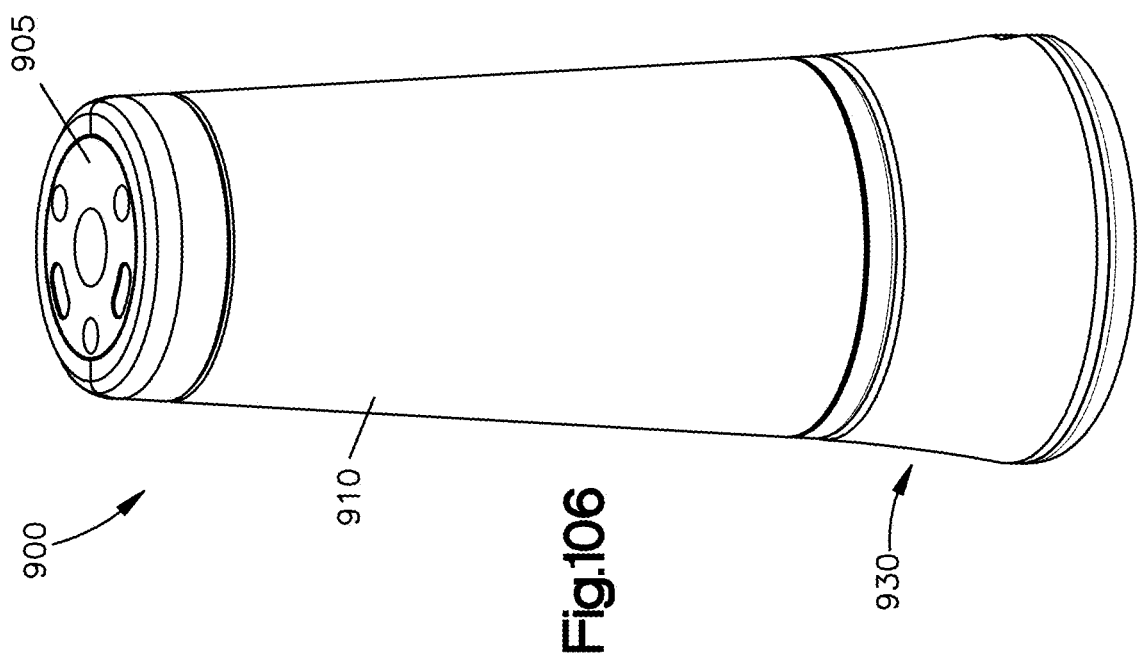

NEEDLING DEVICE AND DRUG APPLICATOR

1. CROSS-REFERENCE TO RELATED APPLICATIONS

This application is a national stage of International Patent Application No. PCT/US2016/053972, filed Sep. 27, 2016, which claims the benefit of U.S. Provisional Application No. 62/233,373, filed on Sep. 27, 2015, each of which is incorporated herein by reference in its entirety for all purposes.

2. BACKGROUND OF THE INVENTION

2.1 Field of the Invention

The following description relates to a needling device for needling of a subject's skin by a user such as a physician or any user, and a fluid or drug dispensing applicator device for massaging and applying a fluid or drug to a subject's skin. In certain embodiments, the subject is in need of inducing hair growth or hair follicle neogenesis, is need of preventing hair loss, and/or is a subject as described in Section 5.5. For example, a needling device may be applied to a subject's skin for hair growth applications, or may also be used for wrinkle reduction, scar revision, hair removal, tattoo removal, and pigmentation. The fluid or drug applicator device may be used for multiple drug application purposes such as applying a hair growth compound to the skin of a subject or treatment for other dermatological conditions.

2.2 Description of Related Art

Needling devices are typically used for tattoo removal or wrinkle reduction mechanisms by lightly penetrating a subject's skin without penetrating deeper areas of a subject's skin or scalp. A conventional needling device does not allow a user to easily interchange needling adapters, and maintain the sterility of the combined device. A conventional device must also be sterilized by a physician, a user, or a clinic prior to use. Further, a conventional needling device provides a set of needles that does not allow uniform needling, and interchangeability and versatility of a device. In addition, conventional needling arrays are provided in configurations that do not allow a user or operator to clearly view a target area while performing the needling operation.

Examples of conventional drug applicators, such as the applicator described in U.S. Patent Application Publication No. 2008/0161737 to Hilditch, allow the manual dispensing of a drug and include a massage head. However, such devices are not programmable, do not allow a user or physician to program the device to automatically follow a preset procedure, and do not provide easy replacement or refilling of the drug to be dispensed. Thus, a device that provides programmable massaging and drug dispensing operations, and ease of replacement and refilling of the liquid or drug to be dispensed, is needed.

3. SUMMARY

In an aspect, a needling device includes a sheath assembly having a needle array and a main unit comprising a motor for driving the needle array, where the main unit is configured to be fully encapsulated within the sheath assembly so that all parts of the main unit are protected from the outside environment. In a specific embodiment, the needle array is driven axially by the motor in a direction that is parallel with a longitudinal axis of the needling device along which the needling device extends. In a specific embodiment, the needling device is adapted to perform needling of a human scalp for promoting hair growth, of skin tissue for skin repair, or of scar tissue for scar removal. In a specific embodiment, the needling device is adapted to treat baldness or chemotherapy-induced alopecia. In a specific embodiment, the needling device is adapted to disrupt a basal or suprabasal epidermal layer of a human skin. In a specific embodiment, the sheath assembly keeps the main unit substantially germ free, sterile, or free from biological contamination as a result of fully encapsulating the main unit. In a specific embodiment, the needling device further comprises a bio-barrier within the sheath assembly to prevent contamination from a subject's blood. In a specific embodiment, the sheath assembly further comprises a sheath cap. In a specific embodiment, the sheath cap is removable for inserting or removing the main unit. In a specific embodiment, the sheath cap is configured to control a depth of the needle array without removing the fully encapsulated main unit from within the sheath assembly. In a specific embodiment, the depth of the needle array ranges from a depth extending beyond an end of the sheath assembly and towards a subject's skin to a depth that is fully retracted within the sheath assembly and away from the subject's skin. In a specific embodiment, the main unit further comprises a main unit cap and the sheath cap is configured to rotate the main unit cap. In a specific embodiment, the needling device further comprises one or more buttons for controlling the needling device positioned on a surface of the sheath assembly without removing the fully encapsulated main unit from within the sheath assembly. In a specific embodiment, the one or more buttons are configured to control one or more of a depth of skin penetration of the needle array, a speed of needling, a power of the needling device, and a LED for illumination of a perturbation area. In a specific embodiment, the main unit further comprises a main unit cap and a drive shuttle chassis for controlling a depth of the needle array, the sheath assembly further comprises a sheath cap, and in response to a user rotating the sheath cap, the main unit cap is rotated, the drive shuttle chassis is axially displaced, and the depth of the penetration of the needle array is adjusted. In a specific embodiment, the needling device eliminates dragging of needles in a subject's skin. In a specific embodiment, the needle array comprises a rectangular base and two substantially parallel rows of needles on the rectangular base so that a speed of needling is increased and a number of needling strokes is reduced. In a specific embodiment, the main unit further comprises a drive shaft that is configured to contact the needle array for controlling needling. In a specific embodiment, the main unit further comprises a drive element and the drive element is attached to the drive shaft for actively controlling a positive and return motion of the needle array, the positive motion being towards a skin of a subject and the return motion being away from the skin of the subject and towards the needling device. In a specific embodiment, the needling device is configured to eliminate vibration to reduce fatigue to a user's hand while operating the needling device. In a specific embodiment, the main unit further comprises a drive element that is attached to the motor for controlling a positive and return motion of needling, the positive motion being towards a skin of a subject and the return motion being away from the skin of the subject and towards the needling device. In a specific embodiment, the needling device further comprises a means for emitting infrared rays, wherein follicles of a subject's scalp can be stimulated using both the needle array and the emitted infrared rays. In a specific embodiment, the needling device further comprises a light for illuminating a target region on a subject's skin.

In another aspect, a needling device includes a sheath assembly having a needle array and a main unit having a motor for driving the needle array in a controlled manner, where the needle array includes a rectangular base and two substantially parallel rows of needles on the rectangular base so that a speed of needling is increased and a number of needling strokes is reduced.

In yet another aspect, a needling device includes a sheath assembly having a needle array, and a main unit having a motor for driving the needle array, where the main unit further includes a main unit cap and a drive shuttle chassis for controlling a depth penetration of the needle array, the sheath assembly further includes a sheath cap, and in response to a user rotating the sheath cap, the main unit cap is rotated, the drive shuttle chassis is axially displaced, and the depth of penetration of the needle array in the skin is adjusted.

In an additional aspect, a needling device includes a sheath assembly having a needle array and a main unit having a motor for driving the needle array, where the main unit further includes a drive shaft that is configured to contact the needle array for controlling needling. and a drive element, and where the drive element is attached to the drive shaft for actively controlling a positive and return motion of the needle array, the positive motion being towards a skin of a subject and the return motion being away from the skin of the subject and towards the needling device.

In another additional aspect, a method of using a needling device for stimulating hair growth includes providing a needling device having a sheath assembly having a needle array and a main unit having a motor for driving the needle array, opening the sheath assembly and placing the main unit within the sheath assembly so that the main unit is fully encapsulated and protected from the outside environment, and powering on the needling device. In a specific embodiment wherein the sheath assembly comprises a needle array, the method further comprises removing the sheath assembly; and replacing the sheath assembly with another sheath assembly comprising another needle array.

In yet another additional aspect, a method of using a needling device and a drug applicator for stimulating hair growth includes providing a needling device including a sheath assembly having a needle array and a main unit having a motor for driving the needle array, providing a drug applicator for drug delivery and massaging including a housing, a drug delivery cartridge carried by the housing, a massage head which is mounted on the housing for massaging a subject's skin, using the needling device to perform targeted cutaneous perturbation for disrupting a layer of a human scalp, after using the needling device, using the drug applicator for applying a drug to the disrupted area of the human scalp. In a specific embodiment, the disrupted layer of the human scalp is the basal or suprabasal epidermal layer, and the drug that is applied is minoxidil or a proteasome inhibitor including lactacystin, a peptidyl aldehyde, or pentoxyfilline (PTX). In a specific embodiment, the method further comprises delivering the drug directly to the human scalp to facilitate transdermal transport. In a specific embodiment, the method further comprises massaging the drug that is delivered to the human scalp to evenly spread the drug.

In a further aspect, an applicator for drug delivery and massaging includes a housing, a drug delivery cartridge, and a massage head mounted on the housing, where the drug delivery cartridge is configured to dispense a drug automatically by a dispensing mechanism that is linked to movement of the massage head. In a specific embodiment, the applicator is configured to stretch or massage a subject's skin while simultaneously dispensing the drug. In a specific embodiment, an amount of drug being dispensed can be controlled by controlling a number of massaging strokes per massaging cycle, a stroke distance per massaging cycle, or a profile of the dispensing mechanism. In a specific embodiment, the drug that is applied is minoxidil or a proteasome inhibitor including lactacystin, a peptidyl aldehyde, or pentoxyfilline (PTX). In a specific embodiment, the drug delivery cartridge and the massage head are attached and configured to be removed and replaced simultaneously by a user. In a specific embodiment, the massage head comprises a rigid disc and an elastic massaging element. In a specific embodiment, a speed of the movement of the massage head and a frequency of the massaging effect is adjustable by the user. In a specific embodiment, the adjustable frequency of the massaging effect comprises 1 Hertz, 2 Hertz, and 4 Hertz. In a specific embodiment, the applicator further comprises a controller and a sensor that are configured to detect a rotation angle of the massage head to determine a dispensed dosage using the detected angle. In a specific embodiment, the applicator is operable in a massage-only or a massage-and-dispense mode. In a specific embodiment, a rotation angle of the massage head controls whether the applicator is in the massage-only mode or the massage-and-dispense mode. In a specific embodiment, the applicator further comprises a keypad positioned on a surface of the applicator. In a specific embodiment, the applicator further comprises an LED and a control unit configured to operate the LED in response to determining that a next dose is due. In a specific embodiment, the applicator further comprises an inductive charging base configured to receive the housing for charging the applicator. In a specific embodiment, the applicator further comprises a light for illuminating a target region of the user's skin.

In a further aspect, an applicator for drug delivery and massaging includes a housing, a drug delivery cartridge carried by the housing for dispensing a drug, a massage head which is mounted on the housing for massaging a subject's skin, a cam drive which is mounted in the housing and rotates the drug delivery cartridge and the massage head for providing a massaging effect, and a controller and sensors that are configured to detect a rotation angle of the massage head to determine a dispensed dosage using the detected angle. In a specific embodiment, the drug delivery cartridge and massage head are attached and configured to be removed and replaced simultaneously by a user. In a specific embodiment, the massage head comprises a rigid disc and an elastic massaging element. In a specific embodiment, a speed of the rotation of the massage head and a frequency of the massaging effect is adjustable by the user. In a specific embodiment, the adjustable frequency of the massaging effect comprises 1 Hertz, 2 Hertz, and 4 Hertz. In a specific embodiment, the applicator is operable in a massage-only or a massage-and-dispense mode. In a specific embodiment, a rotation angle of the massage head controls whether the applicator is in the massage-only or the massage-and-dispense operation. In a specific embodiment, the applicator further comprises a keypad positioned on a surface of the applicator. In a specific embodiment, the applicator further comprises an LED and a control unit configured to operate the LED in response to determining that a next dose is due.

In a specific embodiment, the applicator further comprises an inductive charging base configured to receive the housing for charging the applicator.

In a further aspect, a method of using an applicator for hair growth applications includes providing an applicator including a housing, a drug delivery cartridge carried by the housing, and a massage head which is mounted on the housing, powering on the applicator, and dispensing a drug automatically by a dispensing mechanism that is linked to movement of the massage head. In a specific embodiment, the drug that is applied is minoxidil or a proteasome inhibitor including lactacystin, a peptidyl aldehyde, or pentoxyfilline (PTX). In a specific embodiment, the method of using the applicator further comprises controlling the applicator remotely. In a specific embodiment, the method of using the applicator further comprises receiving notifications from and interacting with the applicator using a remote user interface. In a specific embodiment, the remote user interface is a mobile application that is configured to communicate with a user in order to facilitate compliance with set parameters.

4. BRIEF DESCRIPTION OF THE SEVERAL VIEWS OF THE DRAWINGS

The foregoing summary, as well as the following detailed description, will be better understood when read in conjunction with the appended drawings. For the purpose of illustration, there is shown in the drawings certain embodiments of the present disclosure. It should be understood, however, that the invention is not limited to the precise arrangements and instrumentalities shown. The accompanying drawings, which are incorporated in and constitute a part of this specification, illustrate an implementation of systems and apparatuses consistent with the present invention and, together with the description, serve to explain advantages and principles consistent with the invention.

FIG. 1 is a right side perspective view illustrating an example of a needling device.

FIG. 2 is a left side perspective view illustrating an example of a needling device.

FIG. 3 is a right side elevational view illustrating an example of a needling device.

FIG. 4 is a left side elevational view illustrating an example of a needling device.

FIG. 5 is a top side elevational view illustrating an example of a needling device.

FIG. 6 is a bottom side elevational view illustrating an example of a needling device.

FIG. 7 is a top end elevational view illustrating an example of a needling device.

FIG. 8 is a bottom end elevational view illustrating an example of a needling device.

FIG. 9A is a side view of an example of a needling device.

Figure 9:
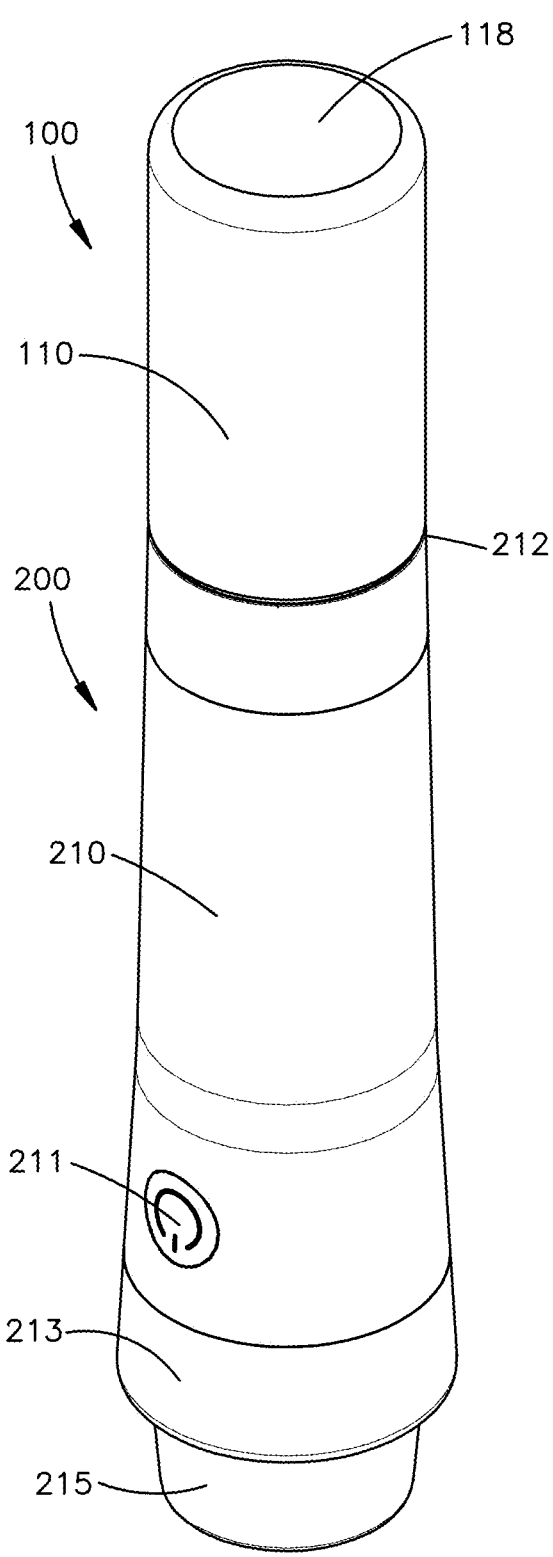
FIG. 9 is a right side perspective view illustrating an example of a needling device with a needling adaptor.

FIGS. 9B, 9C, and 9D are diagrams illustrating sectional views of the needling device along the lines illustrated in FIG. 9A.

Figure 10:
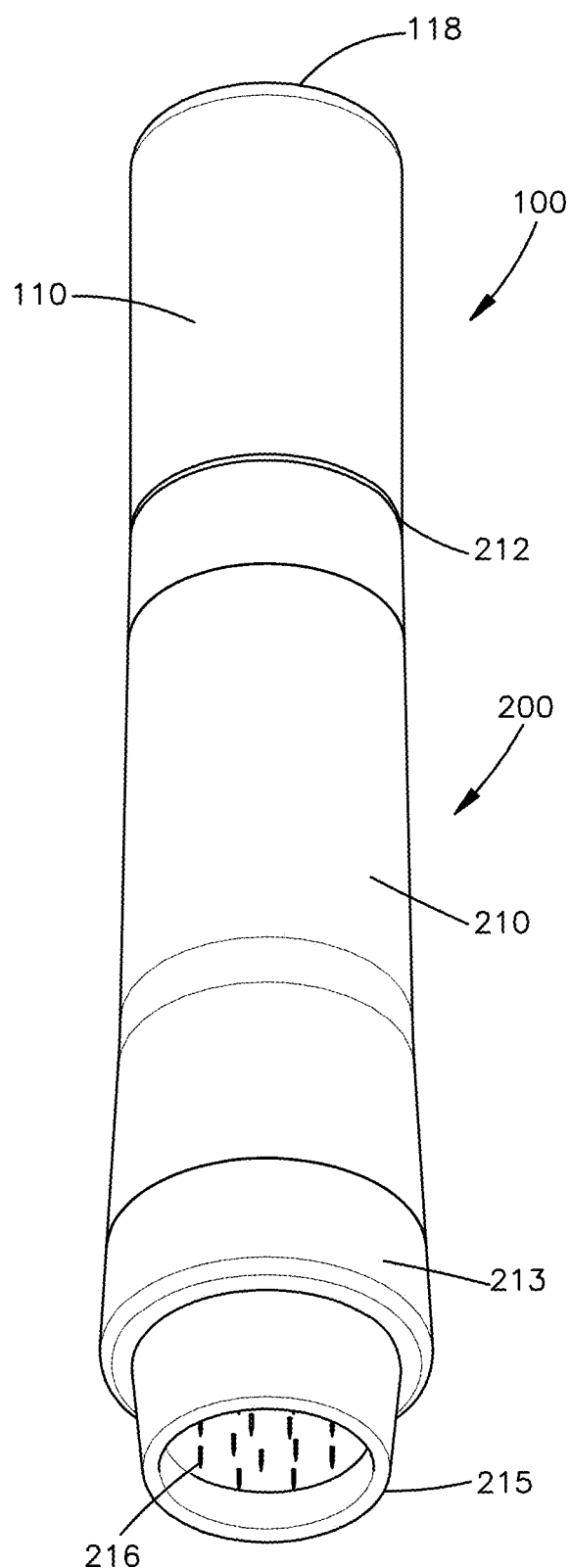

FIG. 10 is a left side perspective view illustrating an example of a needling device with a needling adaptor.

FIG. 11 is a right side elevational view illustrating an example of a needling device with a needling adaptor.

FIG. 12 is a left side elevational view illustrating an example of a needling device with a needling adaptor.

FIG. 13 is a top side elevational view illustrating an example of a needling device with a needling adaptor.

FIG. 14 is a bottom side elevational view illustrating an example of a needling device with a needling adaptor.

FIG. 15 is a top end elevational view illustrating an example of a needling device with a needling adaptor.

FIG. 16 is a bottom end elevational view illustrating an example of a needling device with a needling adaptor.

FIG. 17 is a right side perspective view illustrating an example of a needling adaptor for a needling device.

FIG. 18 is a left side perspective view illustrating an example of a needling adaptor for a needling device.

FIG. 19 is a right side elevational view illustrating an example of a needling adaptor for a needling device.

FIG. 20 is a left side elevational view illustrating an example of a needling adaptor for a needling device.

FIG. 21 is a top side elevational view illustrating an example of a needling adaptor for a needling device.

FIG. 22 is a bottom side elevational view illustrating an example of a needling adaptor for a needling device.

FIG. 23 is a top end elevational view illustrating an example of a needling adaptor for a needling device.

FIG. 24 is a bottom end elevational view illustrating an example of a needling adaptor for a needling device.

Figure 25:
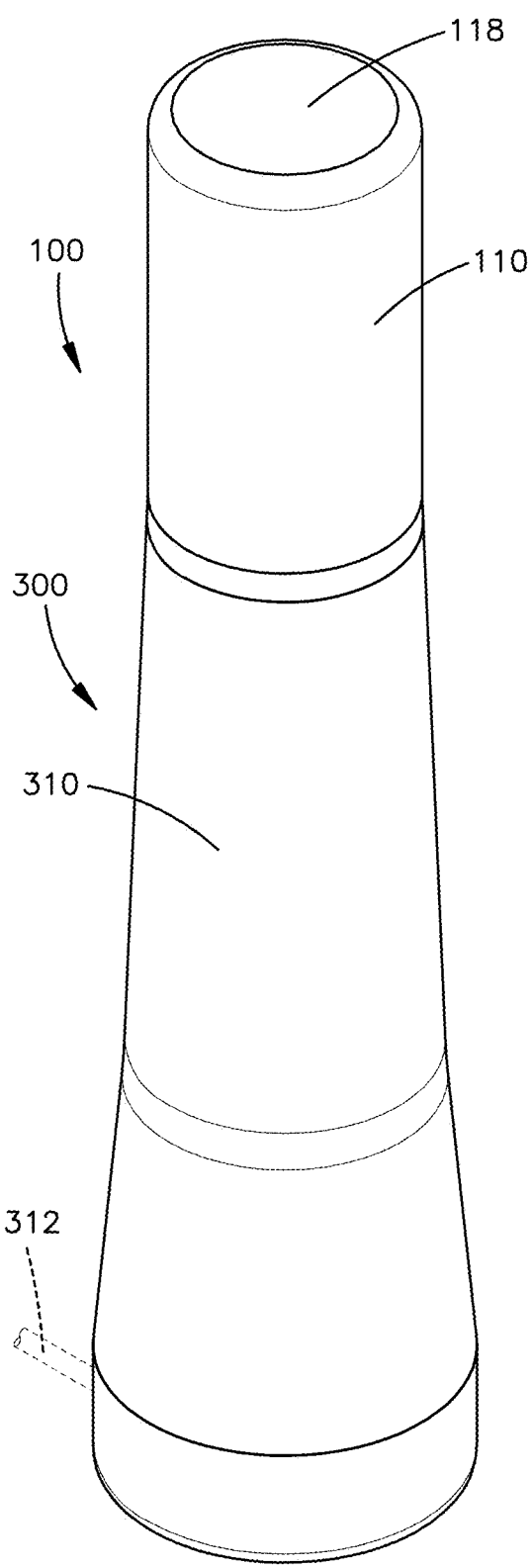

FIG. 25 is a right side perspective view illustrating an example of a needling device with a charging station.

FIG. 25A is a side view of an example of a needling device with a charging station.

FIGS. 25B and 25C are diagrams illustrating sectional views along the lines illustrated in FIG. 25A.

Figure 26:
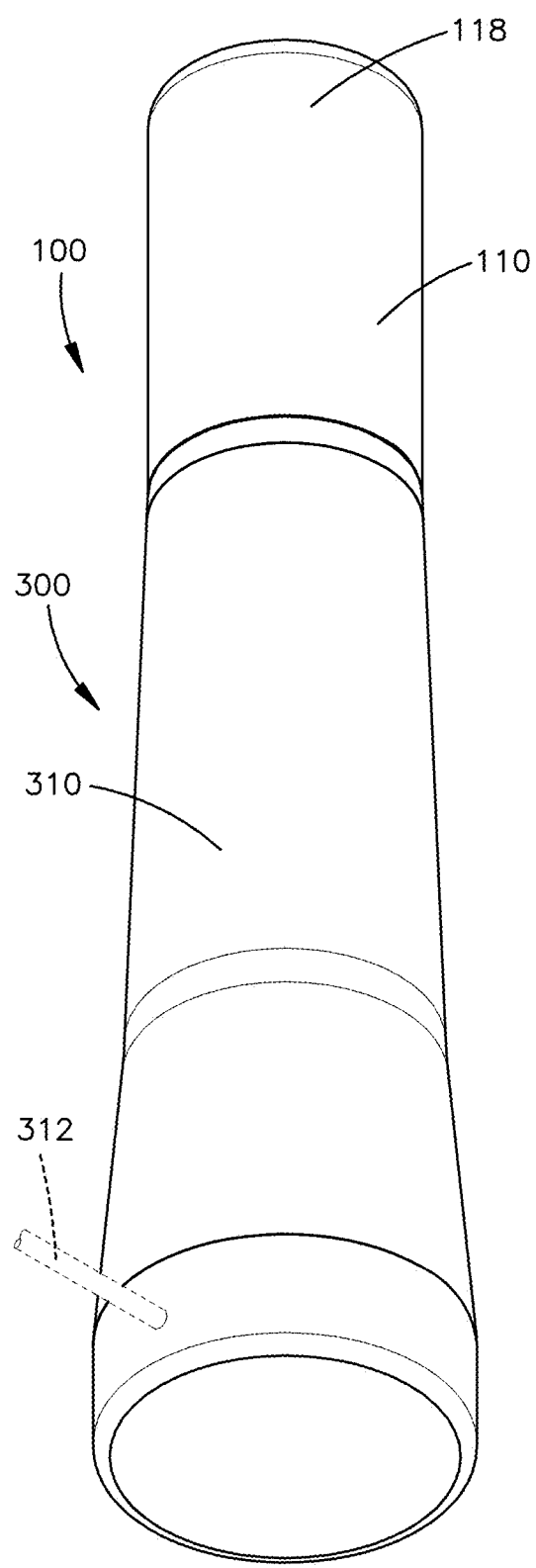

FIG. 26 is a left side perspective view illustrating an example of a needling device with a charging station.

FIG. 27 is a right side elevational view illustrating an example of a needling device with a charging station.

FIG. 28 is a left side elevational view illustrating an example of a needling device with a charging station.

FIG. 29 is a top side elevational view illustrating an example of a needling device with a charging station.

FIG. 30 is a bottom side elevational view illustrating an example of a needling device with a charging station.

FIG. 31 is a top end elevational view illustrating an example of a needling device with a charging station.

FIG. 32 is a bottom end elevational view illustrating an example of a needling device with a charging station.

FIG. 33 is a right side perspective view illustrating an example of a charging station for a needling device.

FIG. 34 is a left side perspective view illustrating an example of a charging station for a needling device.

FIG. 35 is a right side elevational view illustrating an example of a charging station for a needling device.

FIG. 36 is a left side elevational view illustrating an example of a charging station for a needling device.

FIG. 37 is a top side elevational view illustrating an example of a charging station for a needling device.

FIG. 38 is a bottom side elevational view illustrating an example of a charging station for a needling device.

FIG. 39 is a top end elevational view illustrating an example of a charging station for a needling device.

FIG. 40 is a bottom end elevational view illustrating an example of a charging station for a needling device.

FIG. 41 is a right side perspective view illustrating an example of a drug applicator with a massage head.

FIG. 42 is a left side perspective view illustrating an example of a drug applicator with a massage head.

Figure 43:
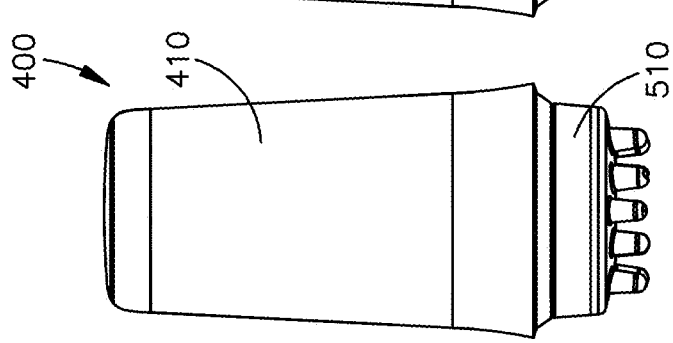

FIG. 43 is a right side elevational view illustrating an example of a drug applicator with a massage head.

Figure 44:
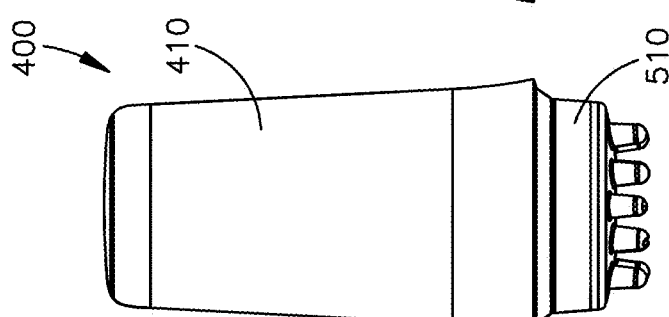

FIG. 44 is a left side elevational view illustrating an example of a drug applicator with a massage head.

Figure 45:
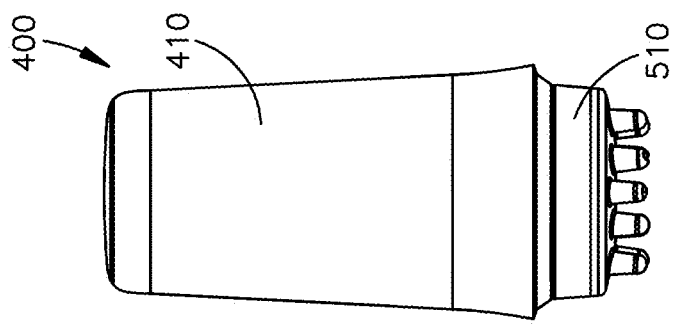

FIG. 45 is a top side elevational view illustrating an example of a drug applicator with a massage head.

Figure 46:
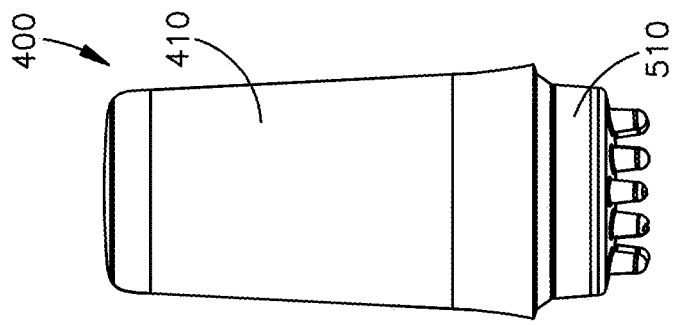

FIG. 46 is a bottom side elevational view illustrating an example of a drug applicator with a massage head.

Figure 47:
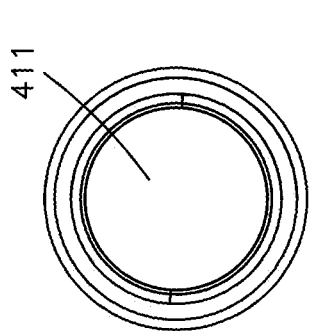

FIG. 47 is a top end elevational view illustrating an example of a drug applicator with a massage head.

Figure 48:
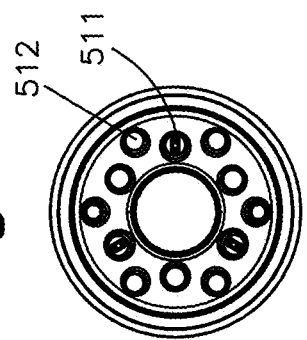

FIG. 48 is a bottom end elevational view illustrating an example of a drug applicator with a massage head.

Figure 49:
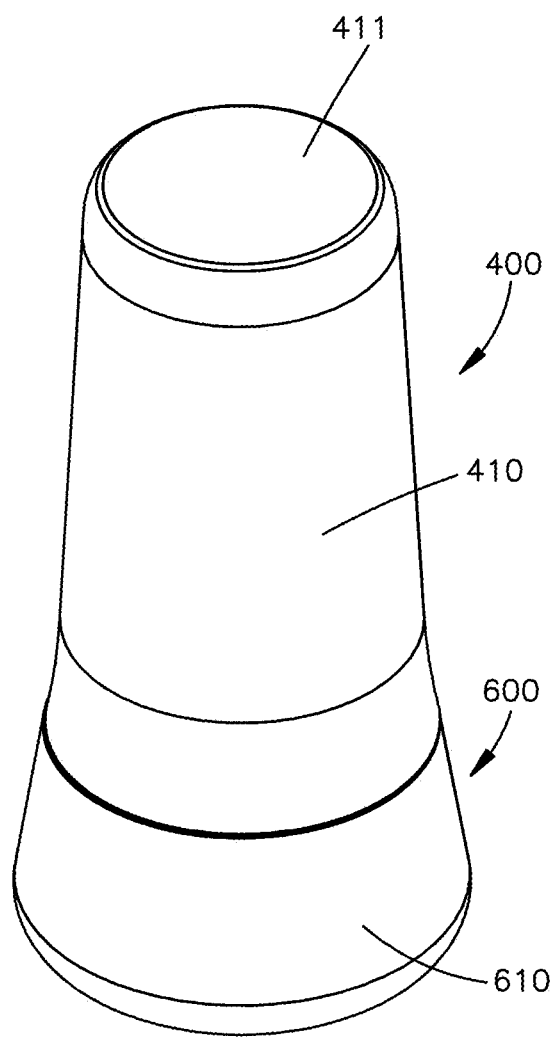

FIG. 49 is a right side perspective view illustrating an example of a drug applicator with a charging station.

Figure 50:
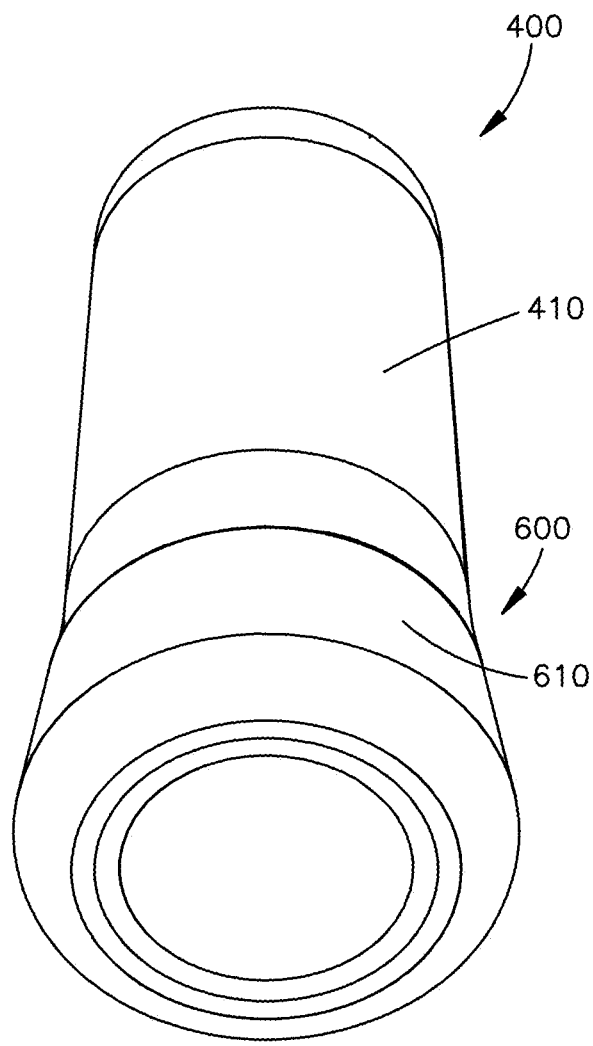

FIG. 50 is a left side perspective view illustrating an example of a drug applicator with a charging station.

FIG. 51 is a right side elevational view illustrating an example of a drug applicator with a charging station.

FIG. 52 is a left side elevational view illustrating an example of a drug applicator with a charging station.

FIG. 53 is a top side elevational view illustrating an example of a drug applicator with a charging station.

FIG. 54 is a bottom side elevational view illustrating an example of a drug applicator with a charging station.

FIG. 55 is a top end elevational view illustrating an example of a drug applicator with a charging station.

FIG. 56 is a bottom end elevational view illustrating an example of a drug applicator with a charging station.

Figure 57:
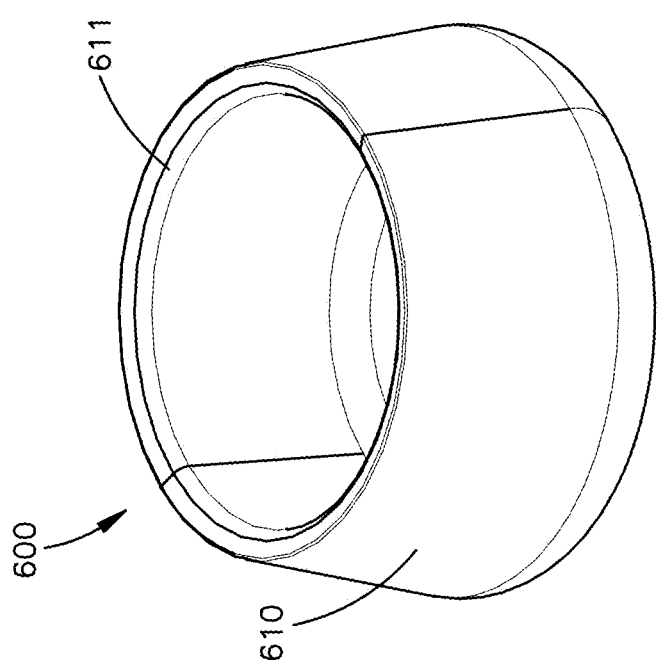

FIG. 57 is a right side perspective view illustrating an example of a charging station for a drug applicator.

Figure 58:
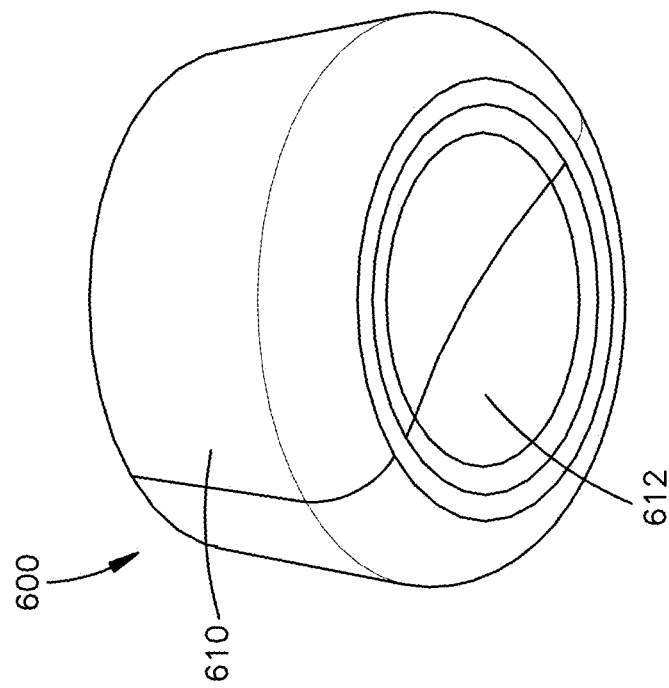

FIG. 58 is a left side perspective view illustrating an example of a charging station for a drug applicator.

Figure 59:
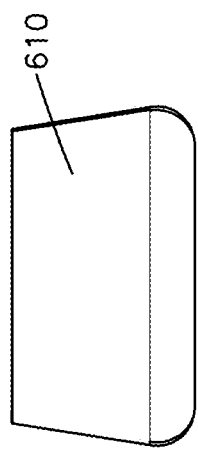

FIG. 59 is a right side elevational view illustrating an example of a charging station for a drug applicator.

Figure 60:
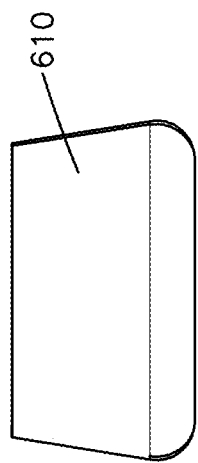

FIG. 60 is a left side elevational view illustrating an example of a charging station for a drug applicator.

Figure 61:
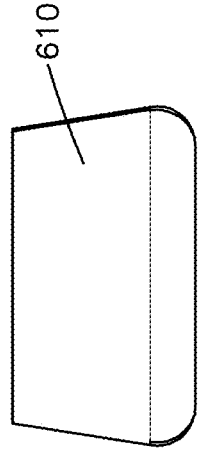

FIG. 61 is a top side elevational view illustrating an example of a charging station for a drug applicator.

Figure 62:
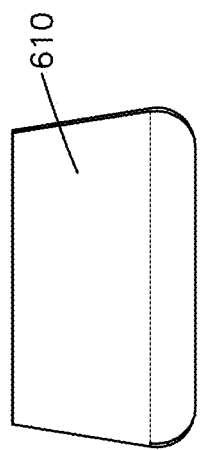

FIG. 62 is a bottom side elevational view illustrating an example of a charging station for a drug applicator.

Figure 63:
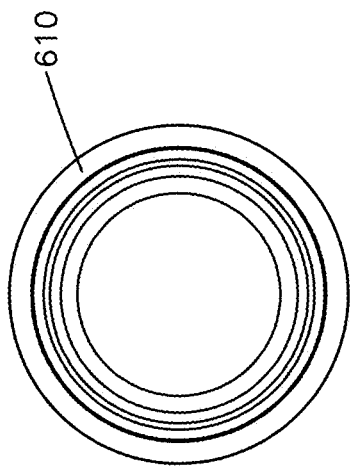

FIG. 63 is a top end elevational view illustrating an example of a charging station for a drug applicator.

Figure 64:
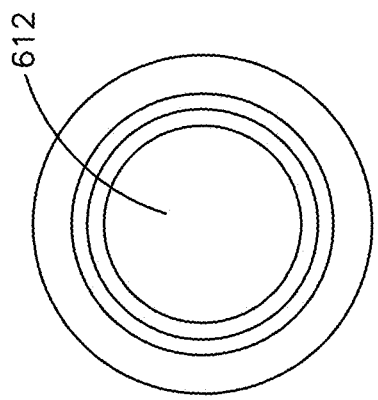

FIG. 64 is a bottom end elevational view illustrating an example of a charging station for a drug applicator.

Figure 65:
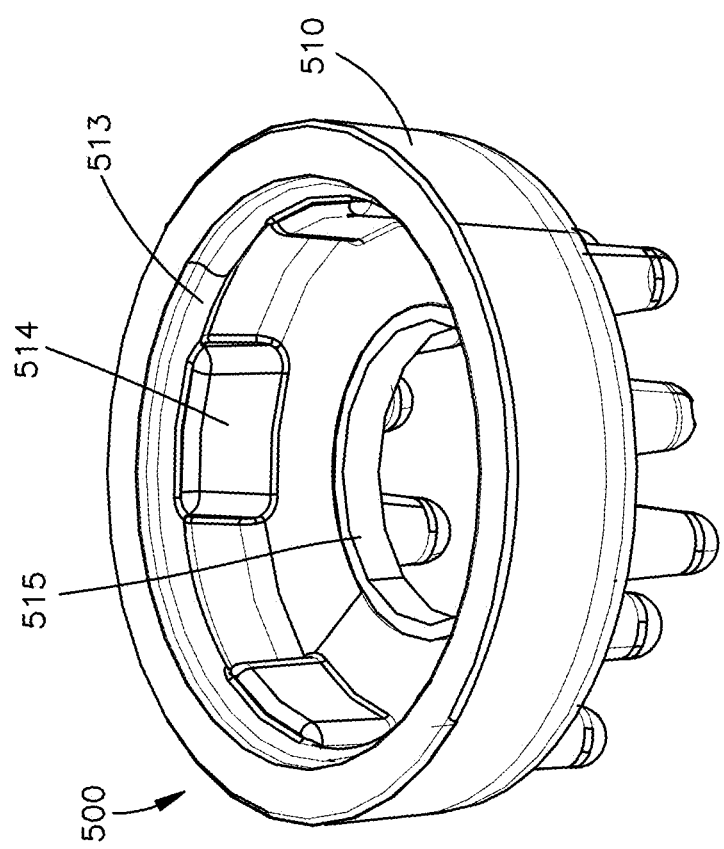

FIG. 65 is a right side perspective view illustrating an example of a massage head for a drug applicator.

Figure 66:
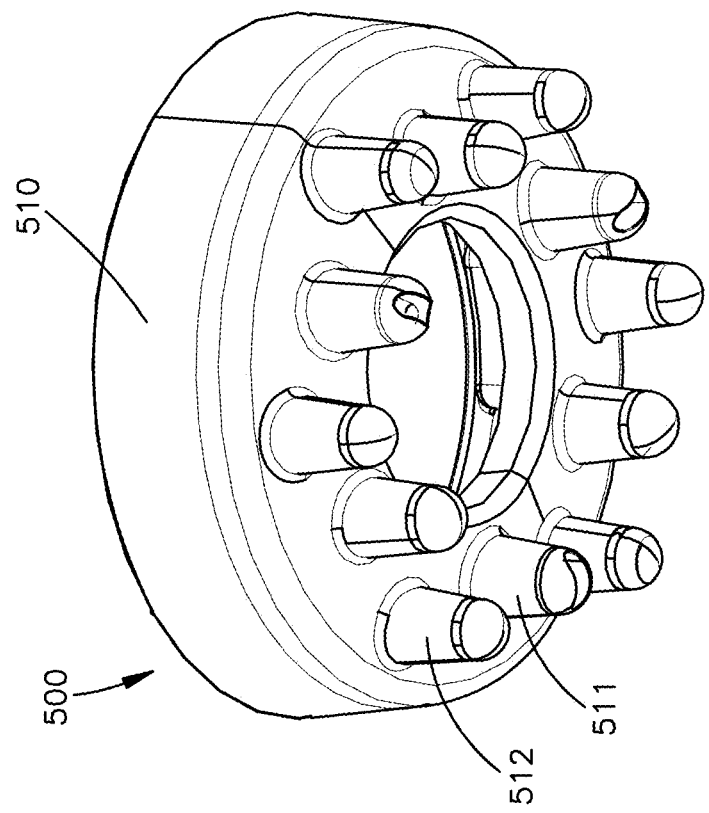

FIG. 66 is a left side perspective view illustrating an example of a massage head for a drug applicator.

Figure 67:
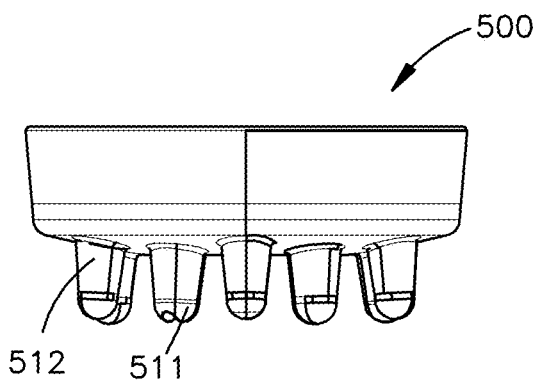

FIG. 67 is a right side elevational view illustrating an example of a massage head for a drug applicator.

Figure 68:
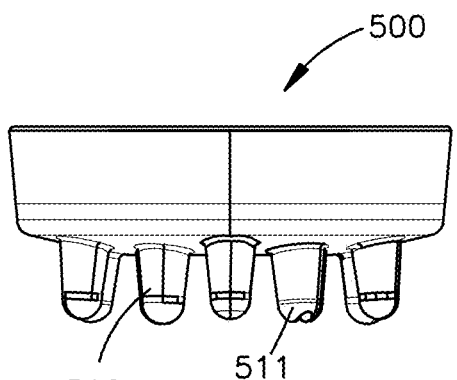

FIG. 68 is a left side elevational view illustrating an example of a massage head for a drug applicator.

Figure 69:
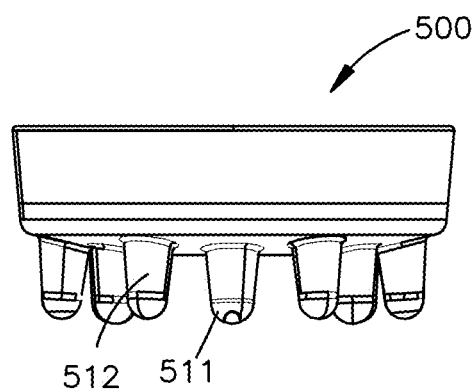

FIG. 69 is a top side elevational view illustrating an example of a massage head for a drug applicator.

Figure 70:
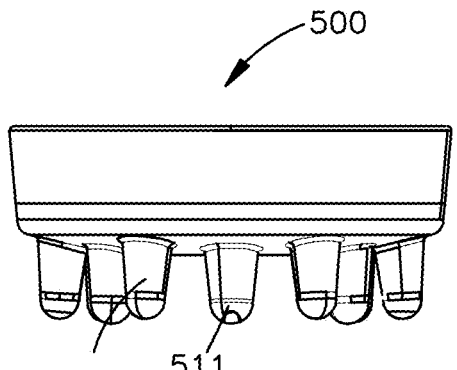

FIG. 70 is a bottom side elevational view illustrating an example of a massage head for a drug applicator.

Figure 71:
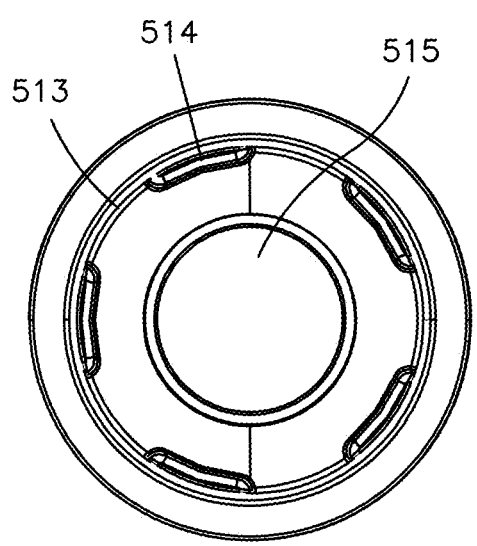

FIG. 71 is a top end elevational view illustrating an example of a massage head for a drug applicator.

Figure 72:
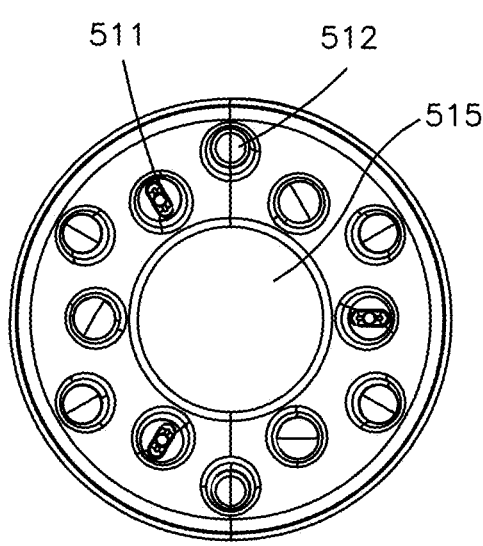

FIG. 72 is a bottom end elevational view illustrating an example of a massage head for a drug applicator.

Figure 73:
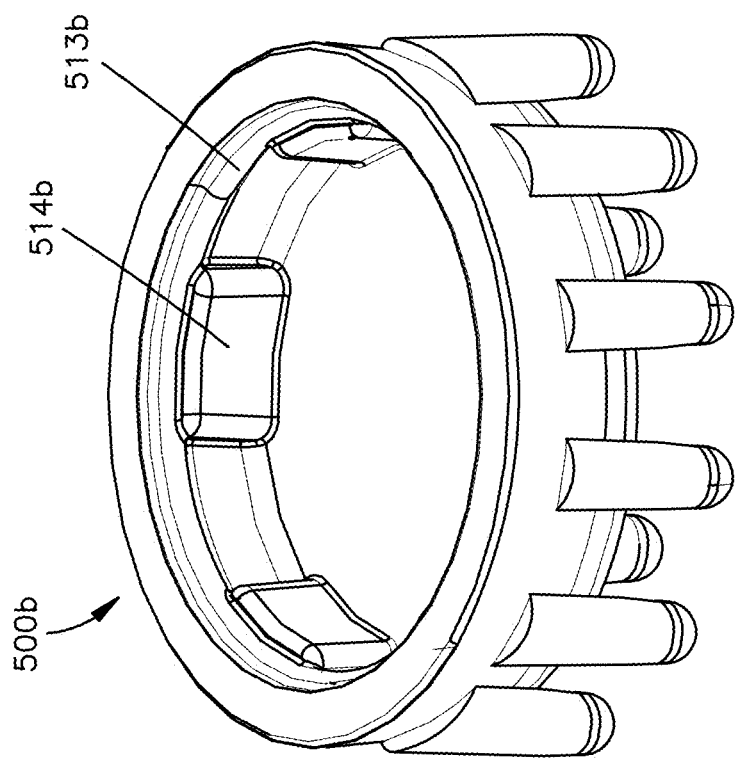

FIG. 73 is a right side perspective view illustrating an example of another massage head for a drug applicator.

Figure 74:
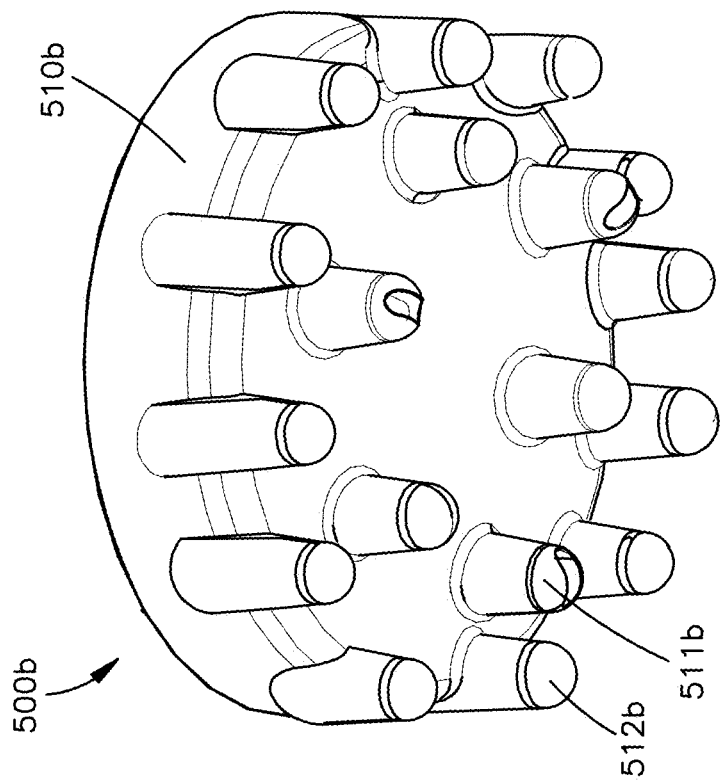

FIG. 74 is a left side perspective view illustrating an example of another massage head for a drug applicator.

Figure 75:
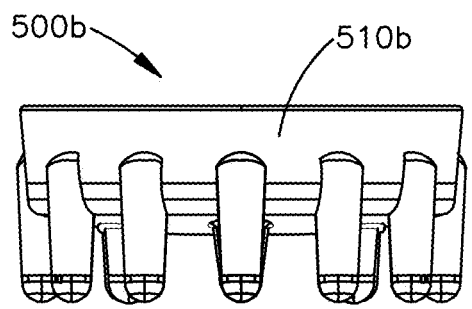

FIG. 75 is a right side elevational view illustrating an example of another massage head for a drug applicator.

Figure 76:
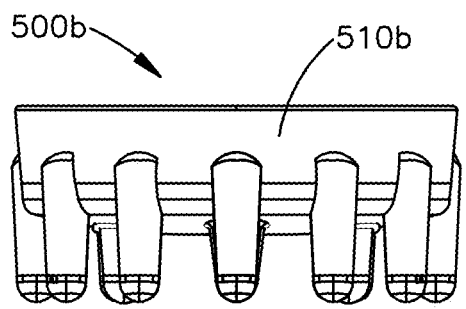

FIG. 76 is a left side elevational view illustrating an example of another massage head for a drug applicator.

Figure 77:
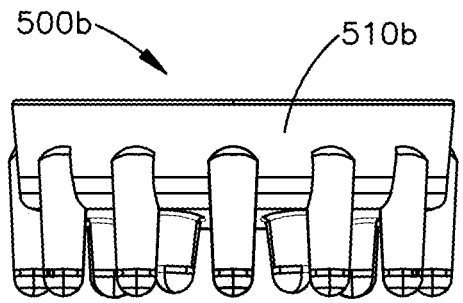

FIG. 77 is a top side elevational view illustrating an example of another massage head for a drug applicator.

Figure 78:
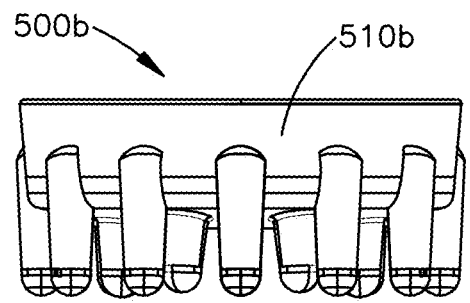

FIG. 78 is a bottom side elevational view illustrating an example of another massage head for a drug applicator.

Figure 79:
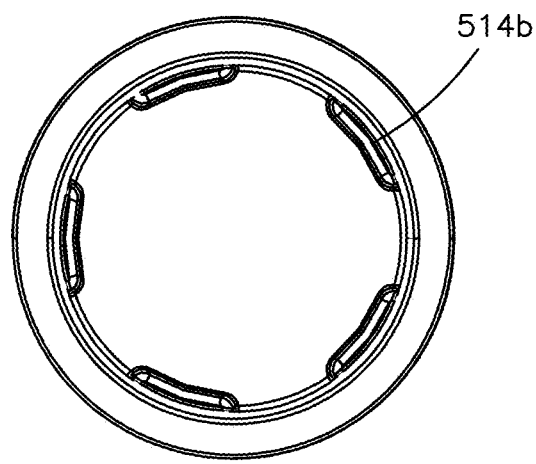

FIG. 79 is a top end elevational view illustrating an example of another massage head for a drug applicator.

Figure 80:
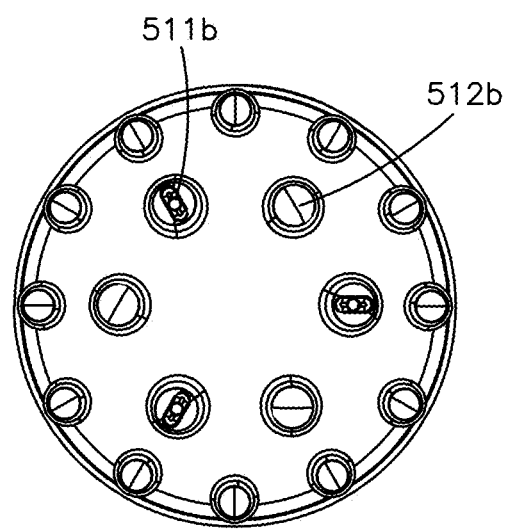

FIG. 80 is a bottom end elevational view illustrating an example of another massage head for a drug applicator.

Figure 81:
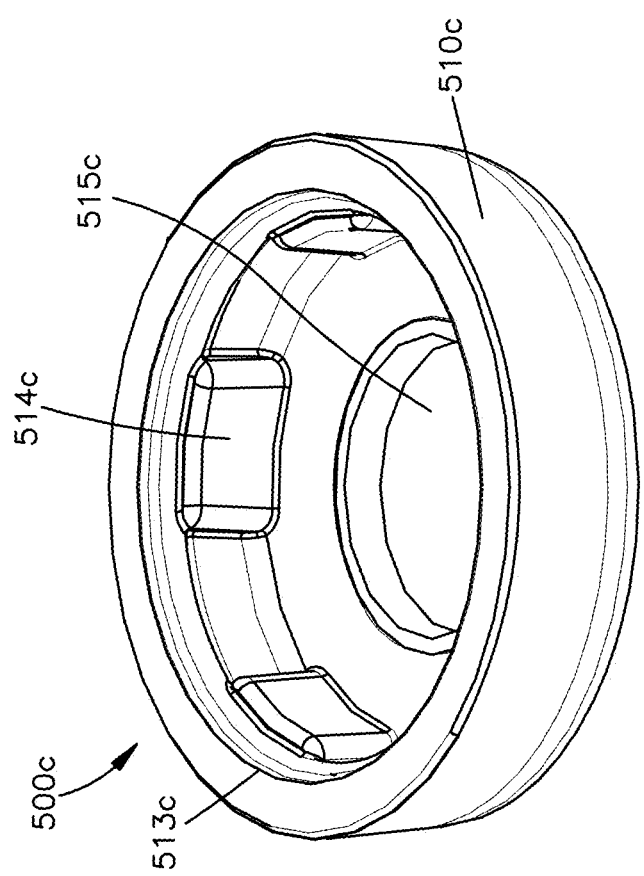

FIG. 81 is a right side perspective view illustrating an example of yet another massage head for a drug applicator.

Figure 82:
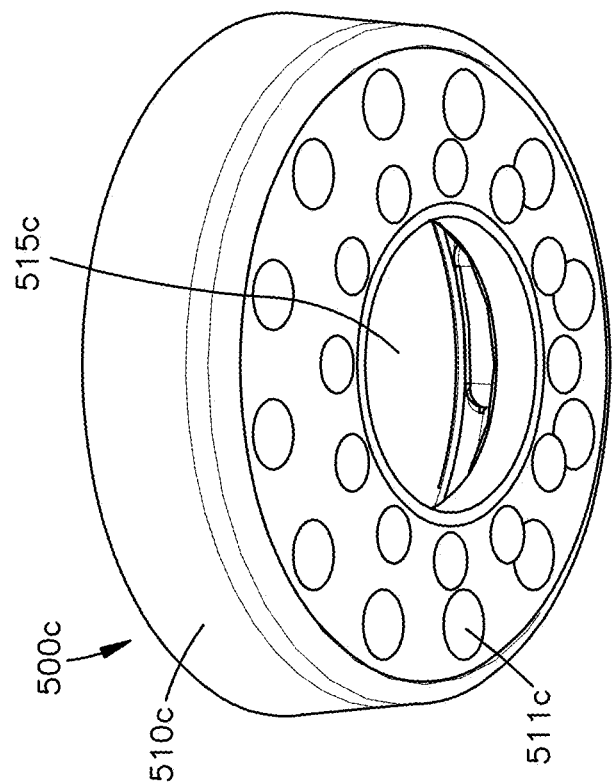

FIG. 82 is a left side perspective view illustrating an example of yet another massage head for a drug applicator.

Figure 83:
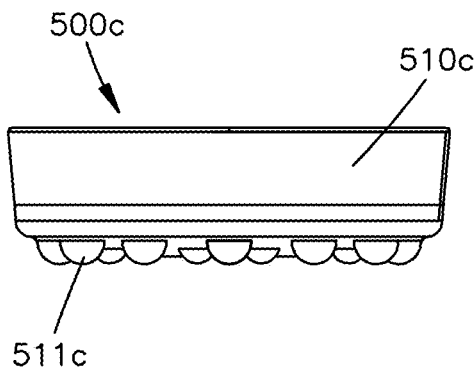

FIG. 83 is a right side elevational view illustrating an example of yet another massage head for a drug applicator.

Figure 84:
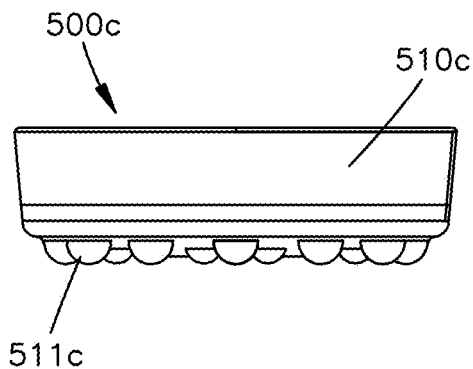

FIG. 84 is a left side elevational view illustrating an example of yet another massage head for a drug applicator.

Figure 85:
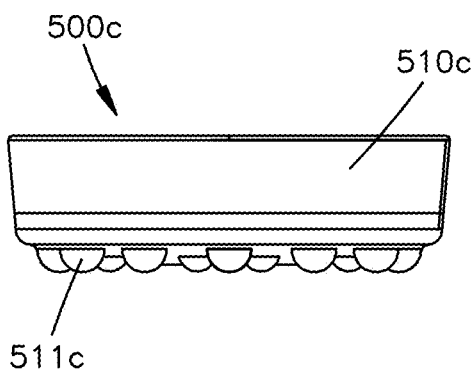

FIG. 85 is a top side elevational view illustrating an example of yet another massage head for a drug applicator.

Figure 86:
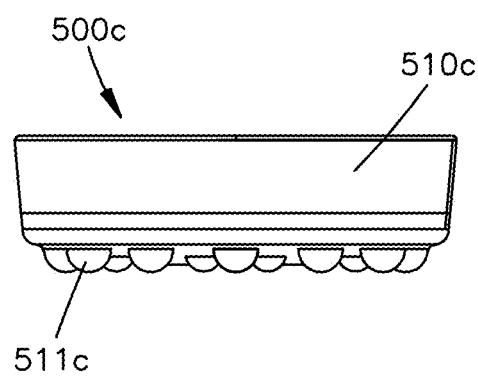

FIG. 86 is a bottom side elevational view illustrating an example of yet another massage head for a drug applicator.

Figure 87:
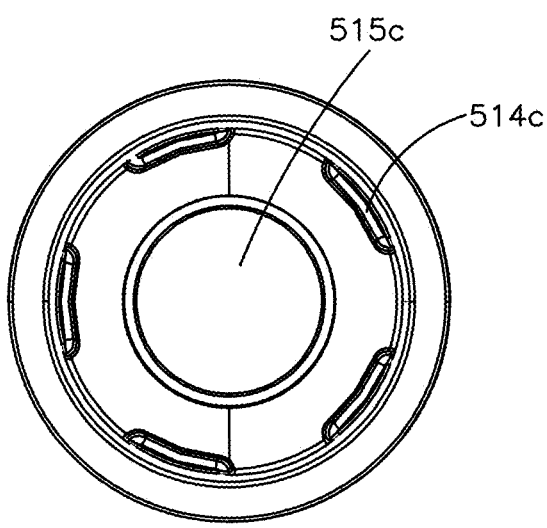

FIG. 87 is a top end elevational view illustrating an example of yet another massage head for a drug applicator.

Figure 88:
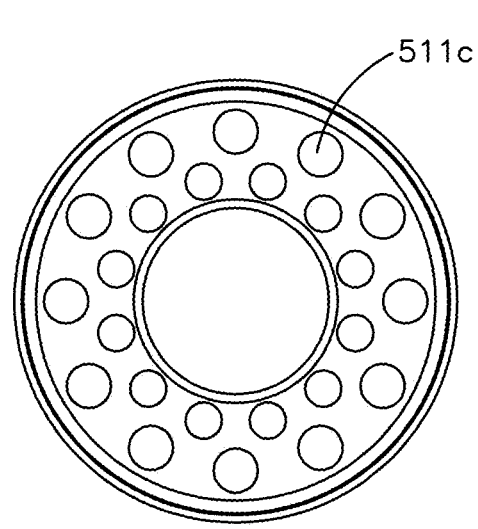

FIG. 88 is a bottom end elevational view illustrating an example of yet another massage head for a drug applicator.

Figure 89:
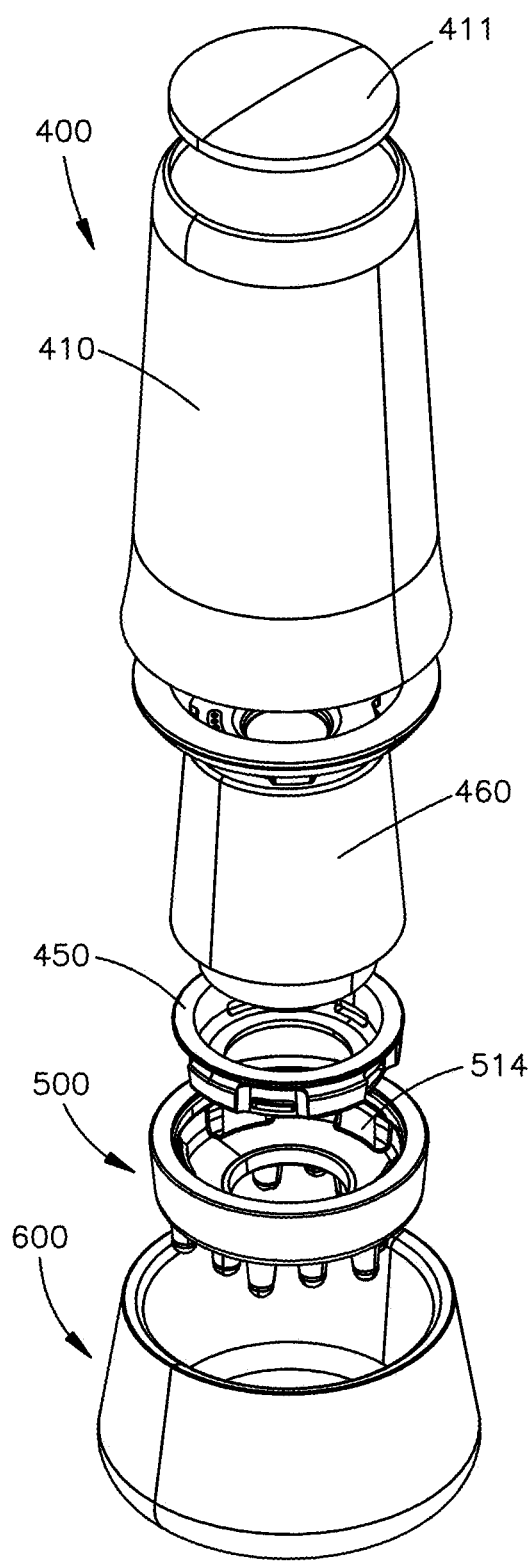

FIG. 89 is a diagram illustrating an example of an exploded view of the drug applicator, massage head, and charging station.

Figure 90:
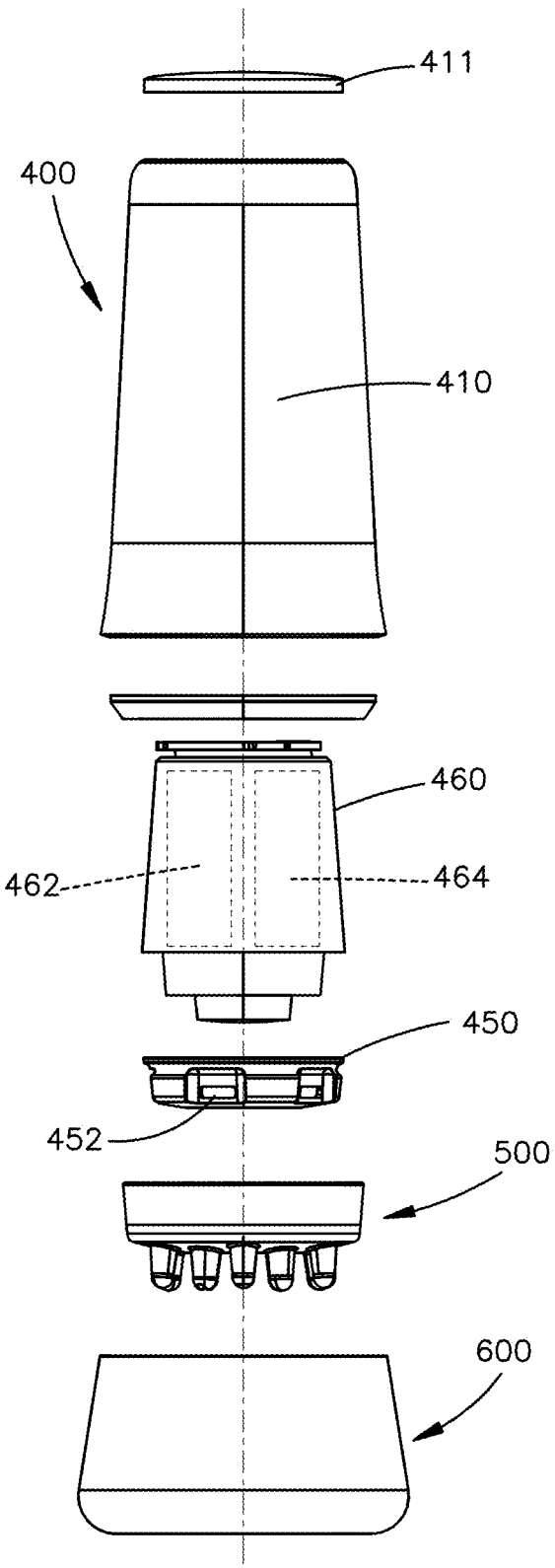

FIG. 90 is a diagram illustrating an example of an exploded cross-sectional view of the drug applicator, massage head, and charging station.

Figures 91, 92:
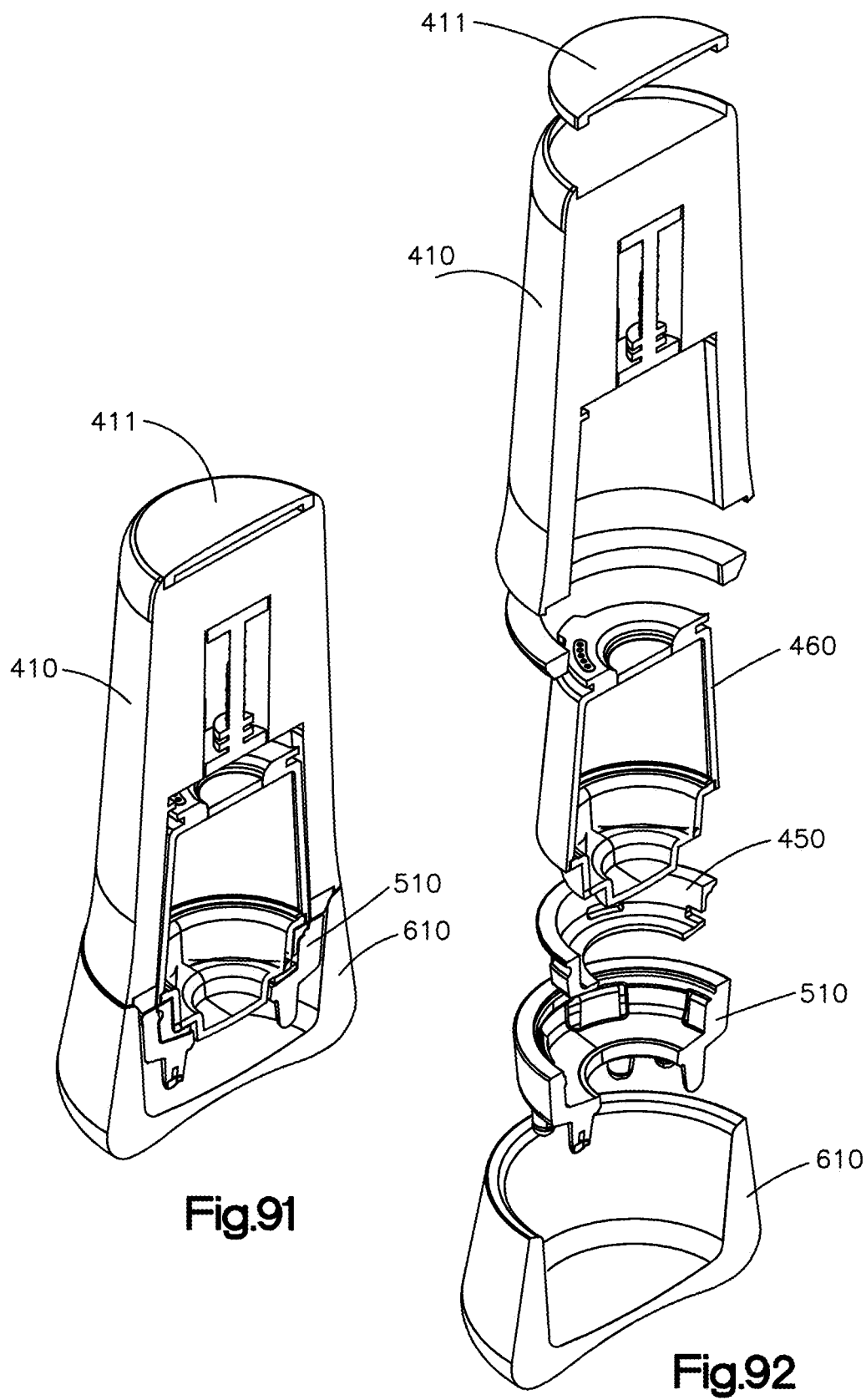

FIG. 91 is a diagram illustrating an example of a cross-sectional view of the drug applicator, massage head, and charging station.

FIG. 92 is a diagram illustrating an example of an exploded three dimensional cross-section of the drug applicator, massage head, and charging station.

Figure 93:
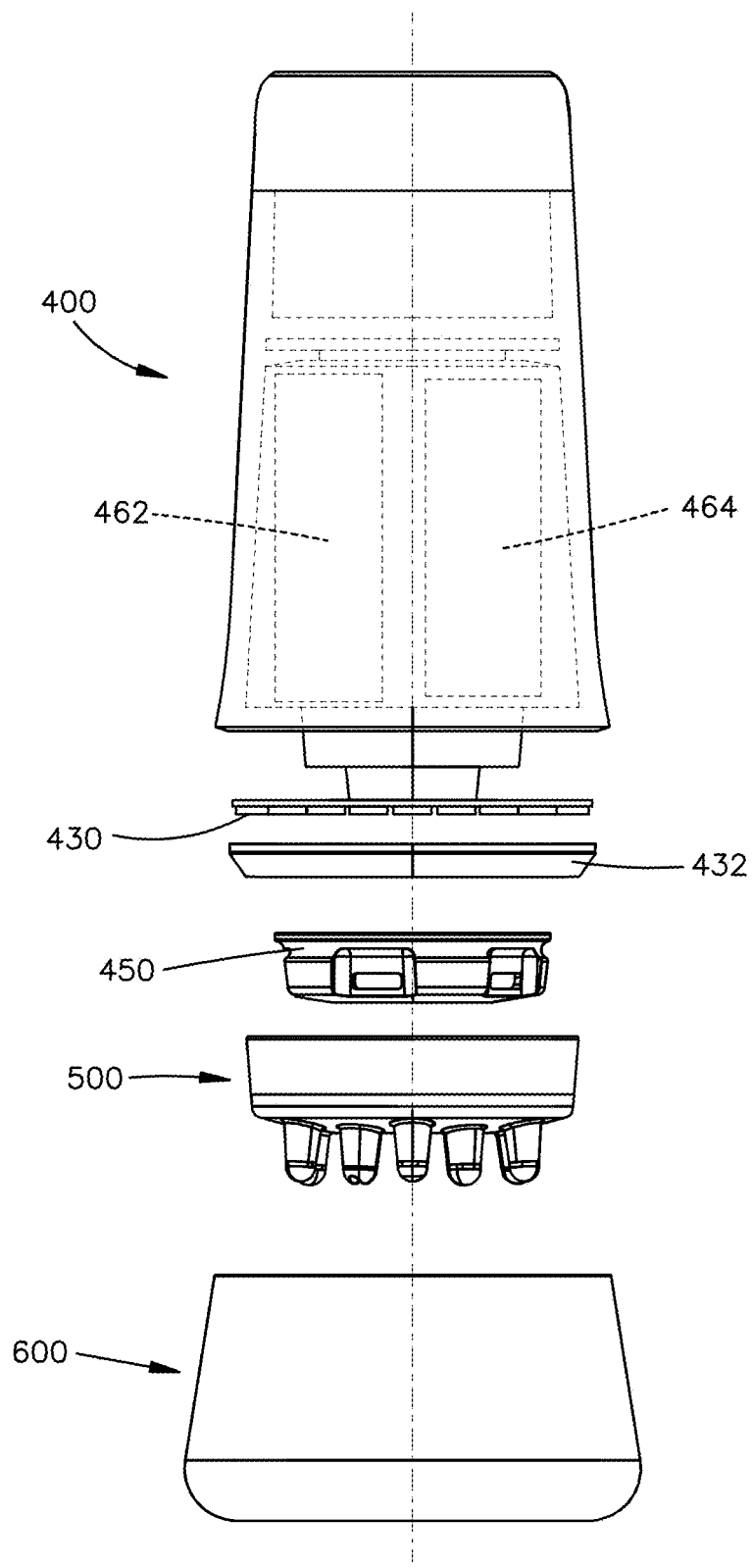

FIG. 93 is a diagram illustrating an example of a cross-sectional view of the drug applicator, massage head, and charging station.

Figure 94:
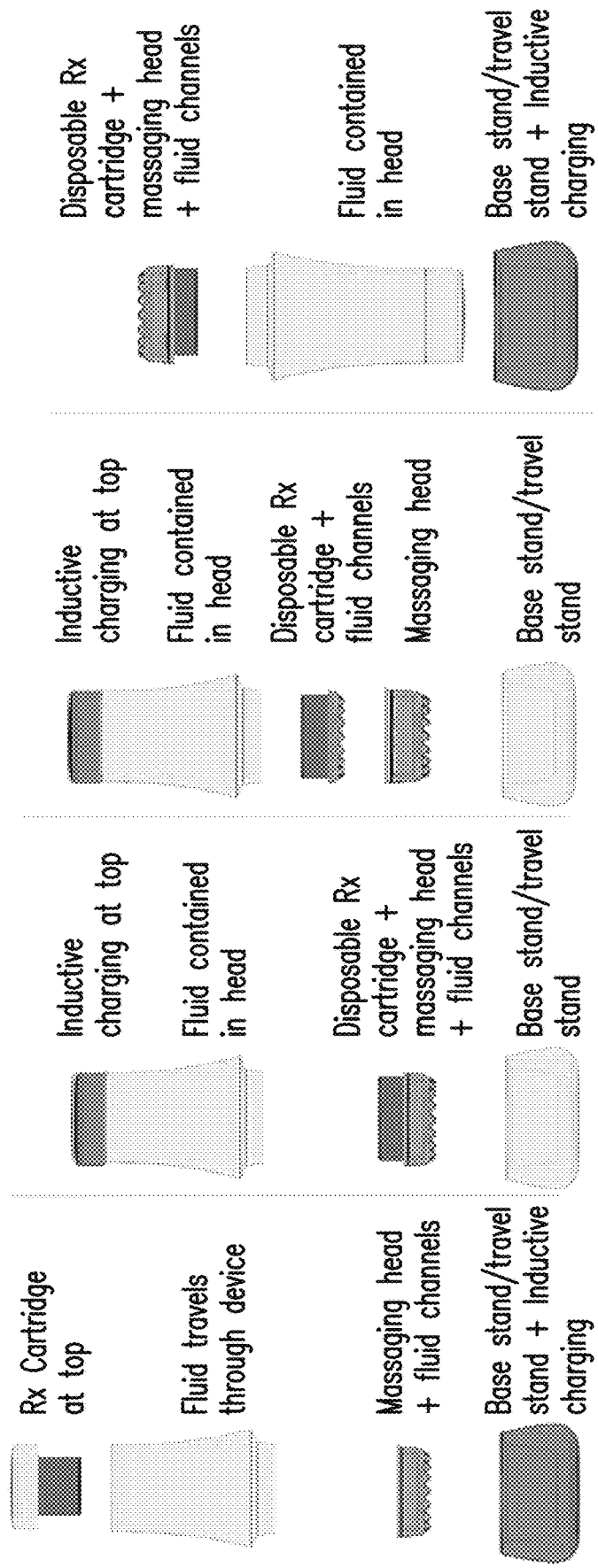

FIG. 94 is a diagram illustrating alternative designs for the removable fluid cartridge of the drug applicator.

FIG. 95 is a diagram illustrating a perspective view of another example of a needling device enclosed within a needling adaptor.

FIG. 96 is a diagram illustrating an exploded view of another example of a needling device enclosed within needling adaptor.

Figure 97:
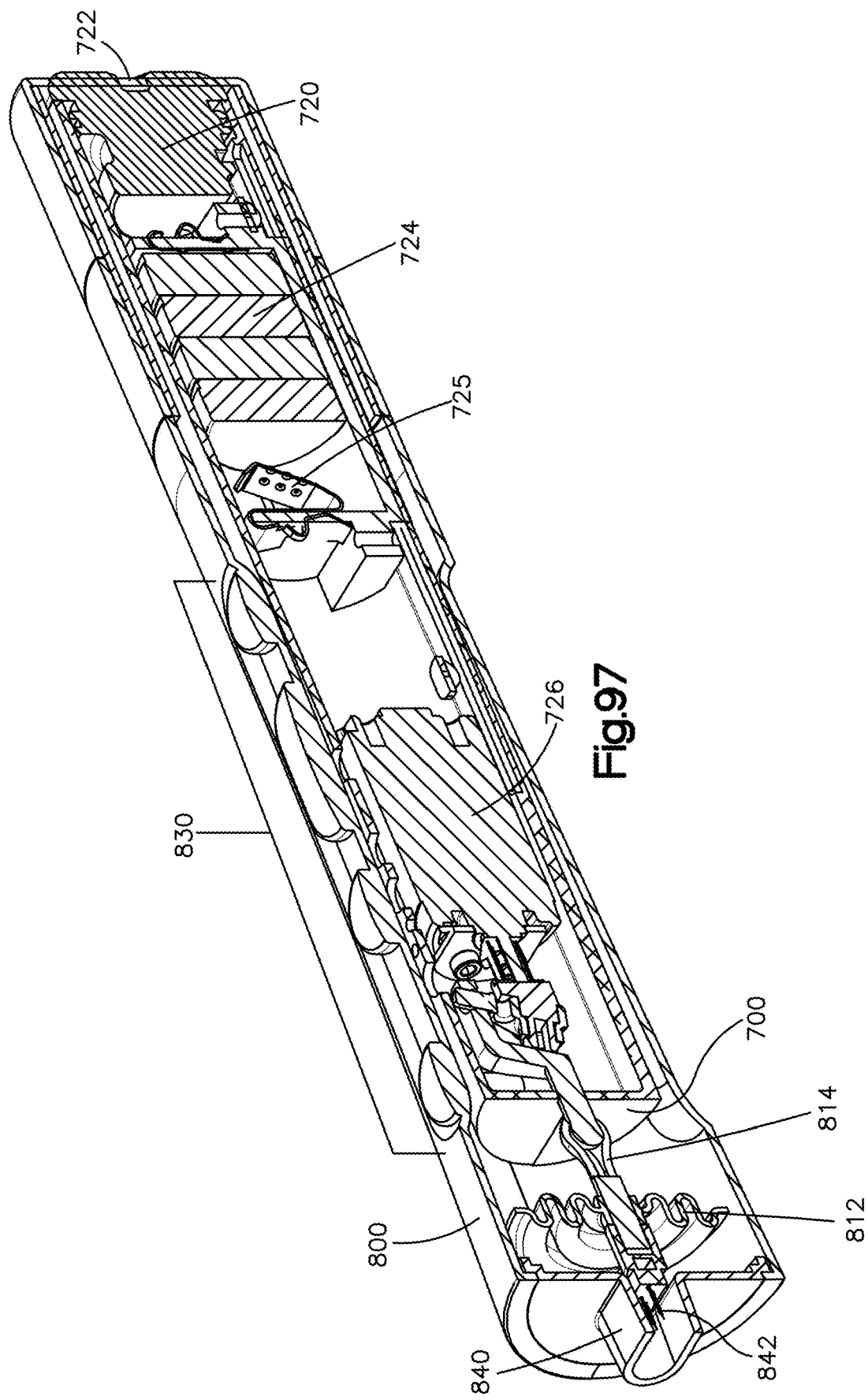

FIG. 97 is a diagram illustrating a cross-sectional view of another example of a needling device enclosed within a needling adaptor.

FIG. 98 is a diagram illustrating a perspective view of the inner components of another example of a needling device.

FIG. 99 is a diagram illustrating a magnified view of the inner components of another example of a needling device.

FIG. 100 is a diagram illustrating an exploded view of the inner components of another example of a needling device.

Figure 101:
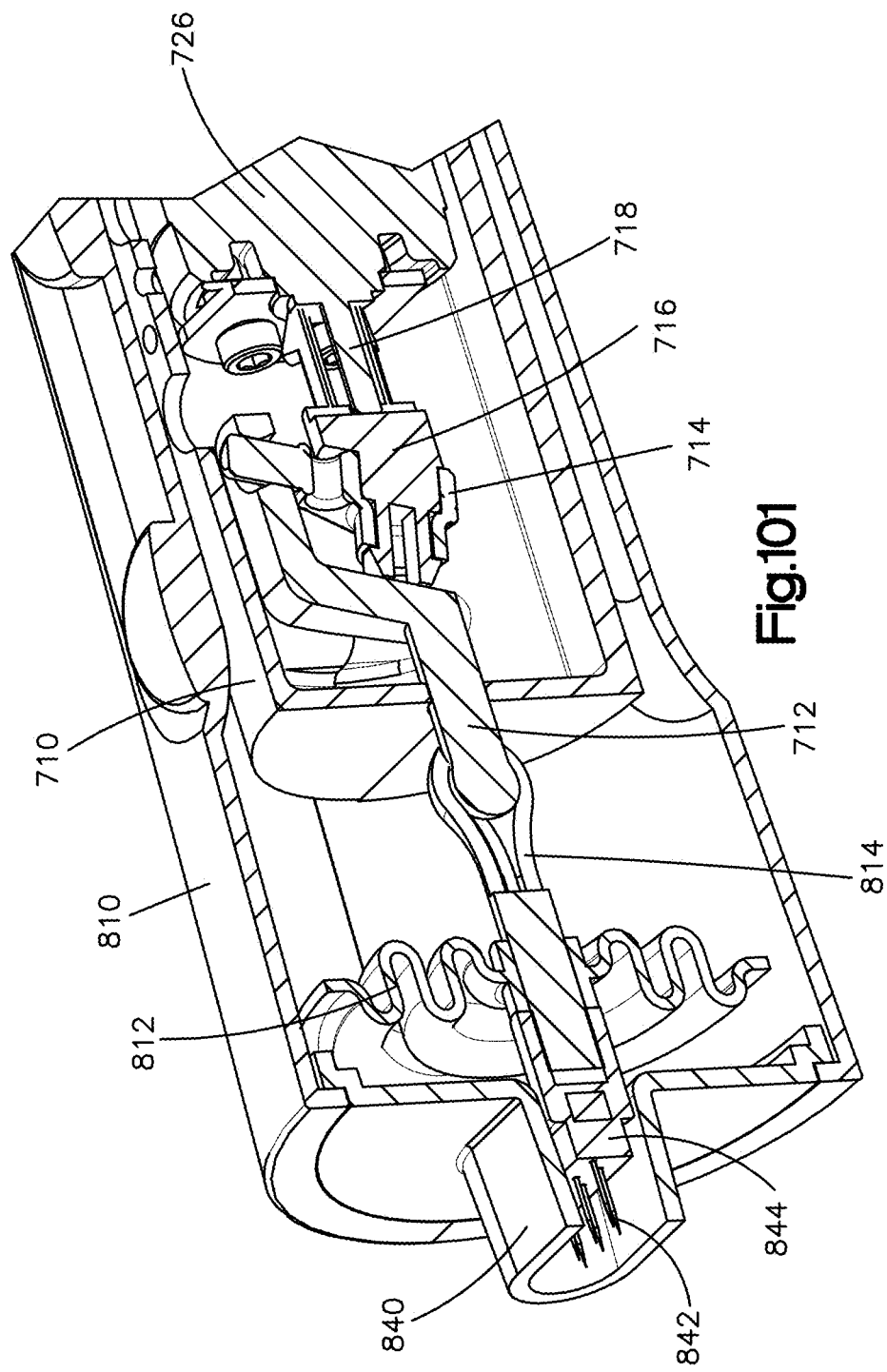

FIG. 101 is a diagram illustrating a magnified view of the cross-section of another example of a needling device enclosed within a needling adaptor.

Figure 102:
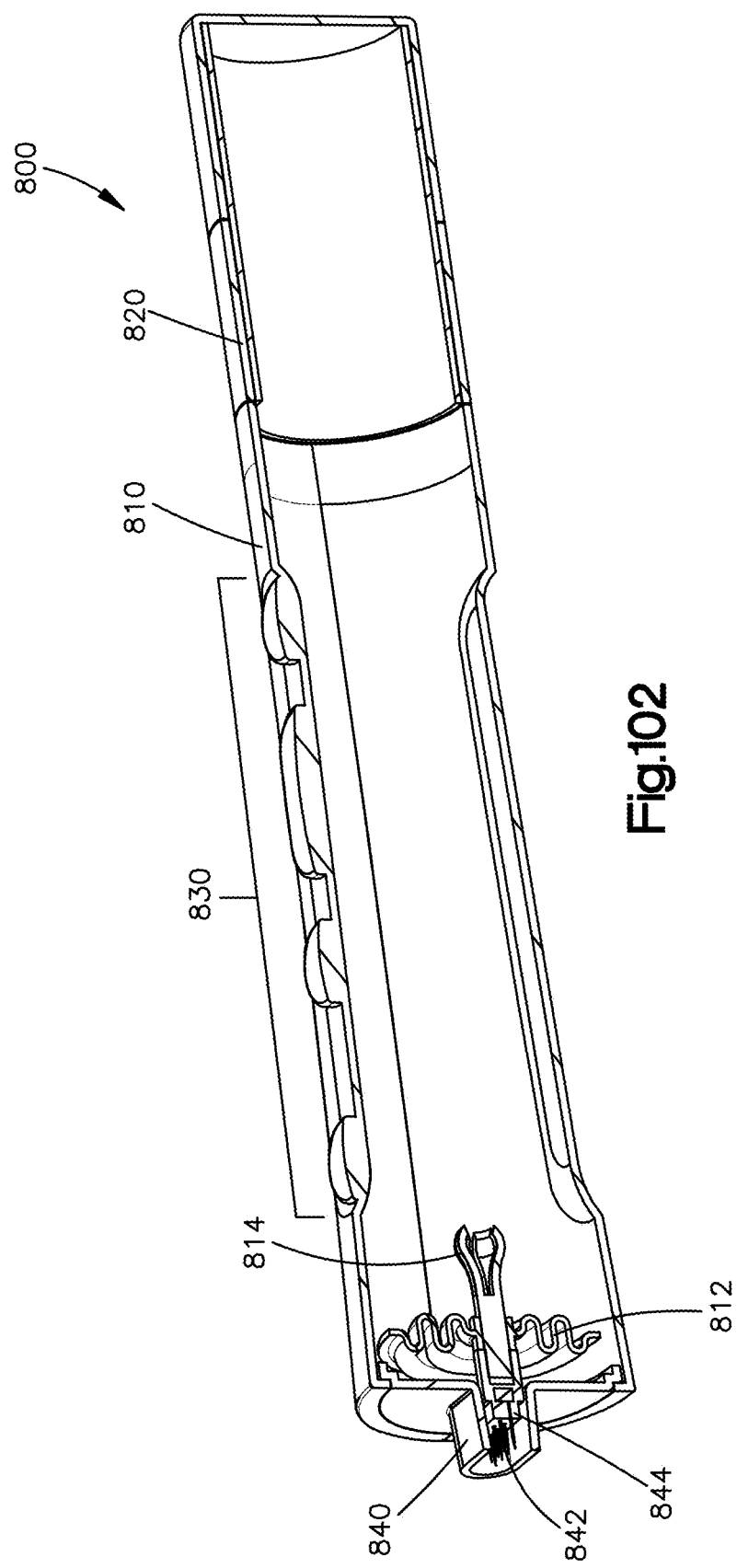

FIG. 102 is a diagram illustrating a cross-sectional view of another example of a needling adaptor.

Figure 103:
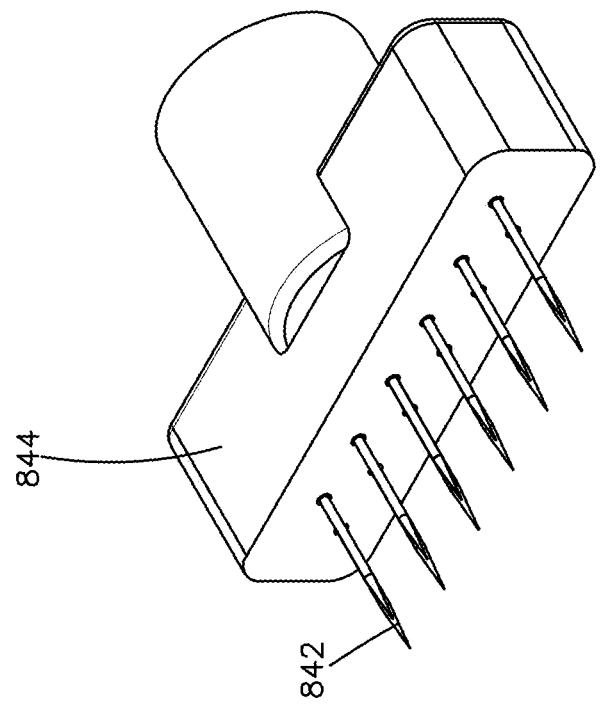

FIG. 103 is a diagram illustrating a perspective view of an example of a needle array.

Figure 104:
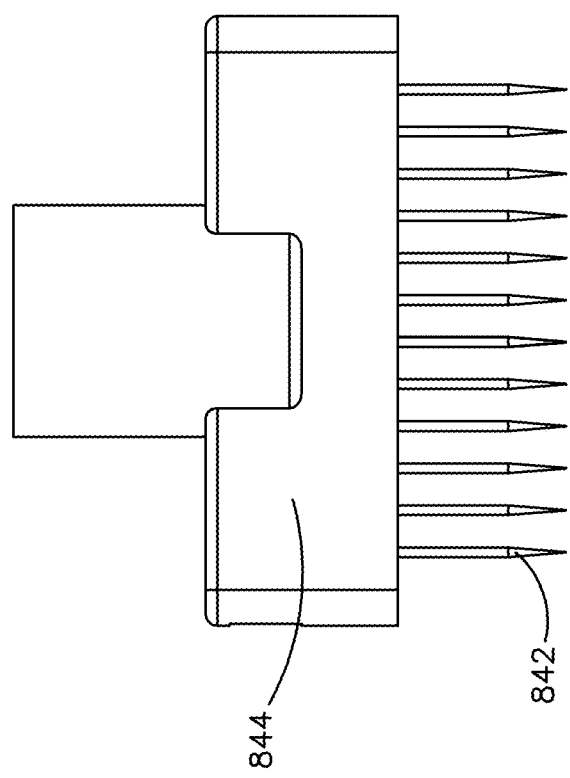

FIG. 104 is a diagram illustrating a side elevation view of an example of a needle array.

Figure 105:
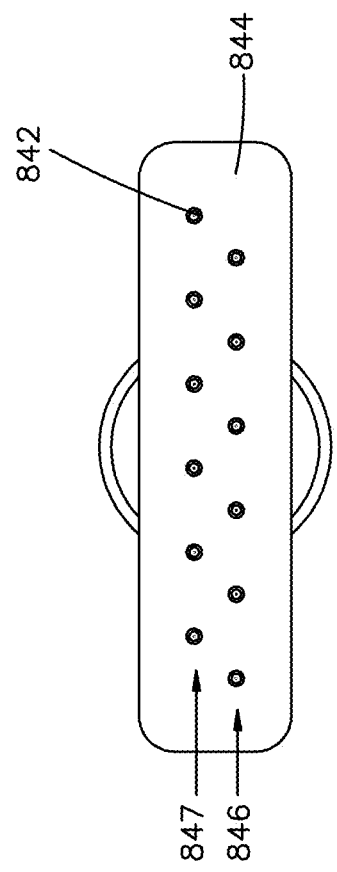

FIG. 105 is a diagram illustrating a bottom end elevation view of an example of a needle array.

FIG. 106 is a diagram illustrating a perspective view of another example of a drug applicator with a massage head and a charging station.

FIG. 107 is a diagram illustrating a cross-sectional view of another example of a drug applicator with a massage head and a charging station.

Figure 108:
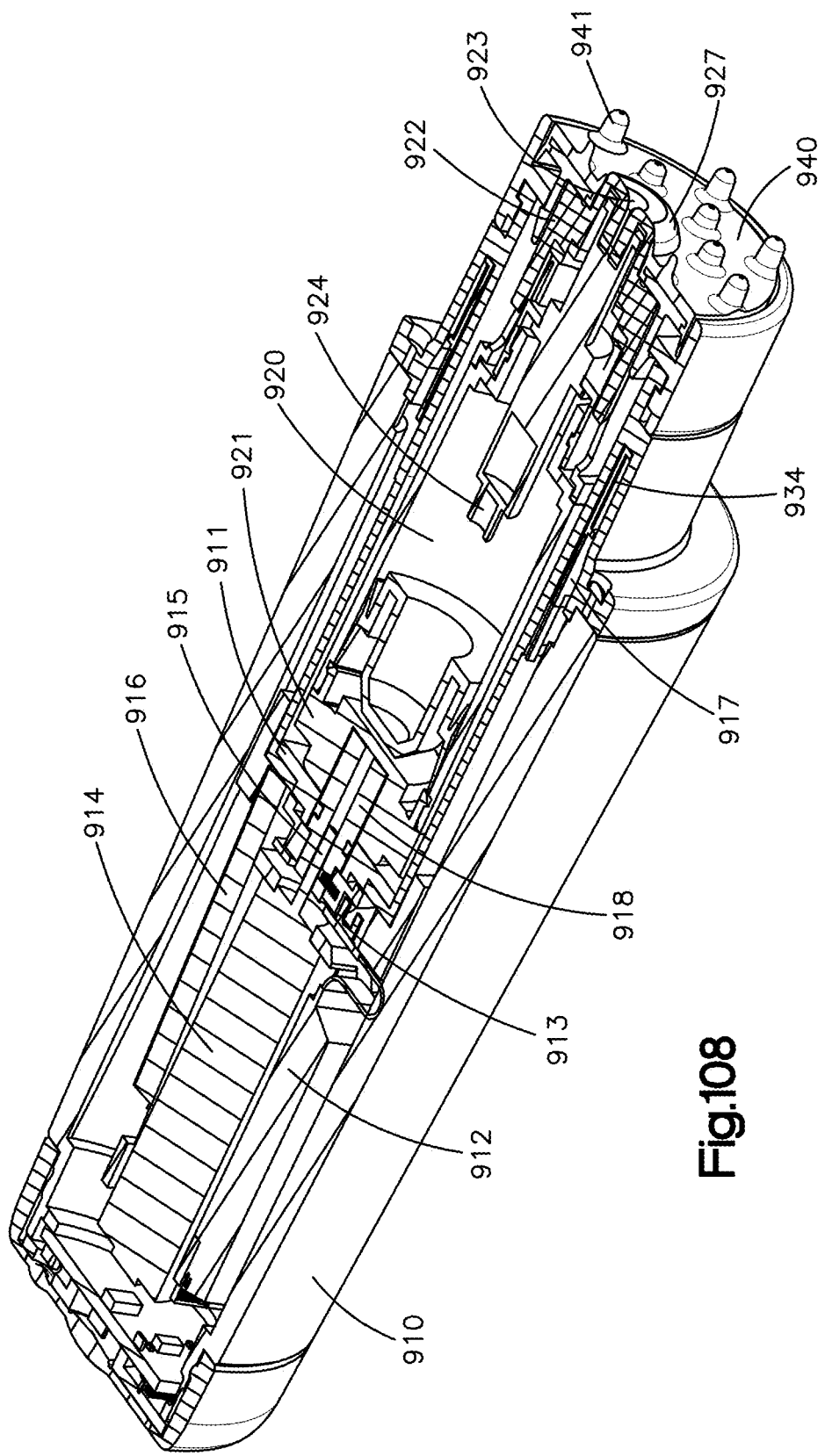

FIG. 108 is a diagram illustrating a cross-sectional view of another example of a drug applicator.

Figure 109:
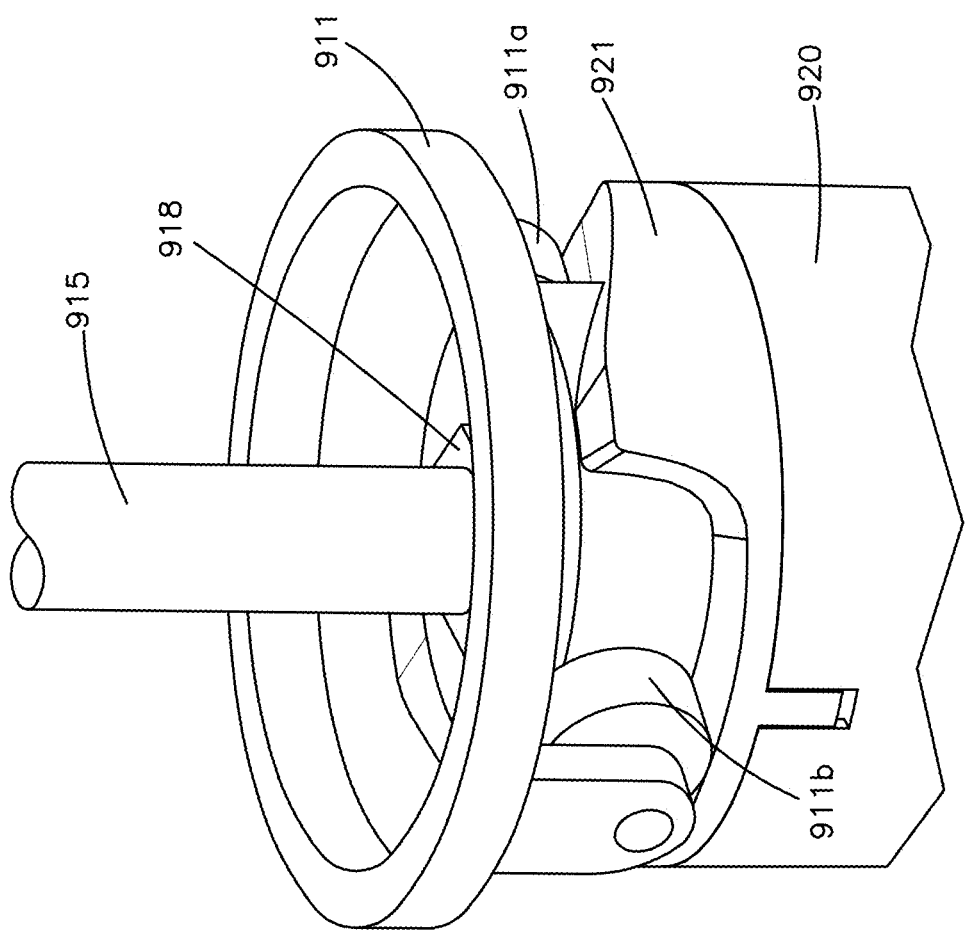

FIG. 109 is a diagram illustrating a magnified perspective view of the inner components of another example of a drug applicator.

Figure 110:
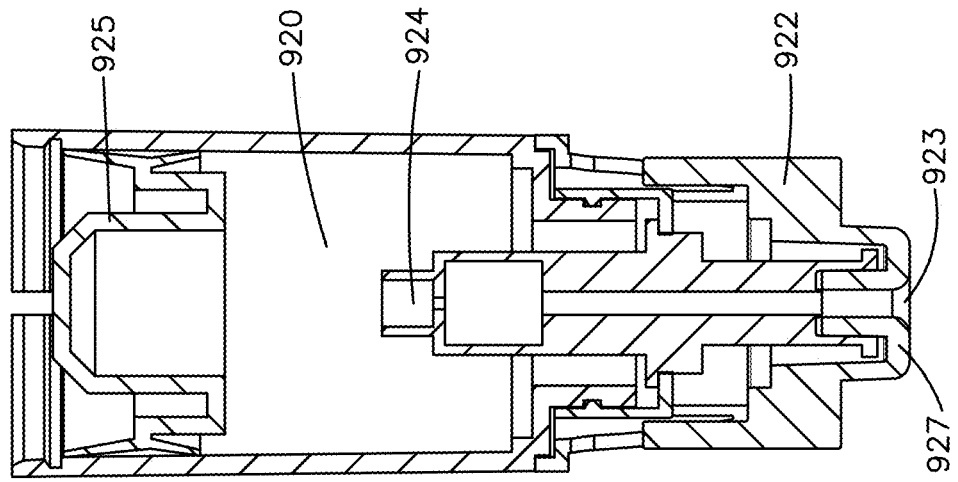

FIG. 110 is a diagram illustrating a cross-sectional view of an example of a cartridge for use with a drug applicator.

Figure 111:
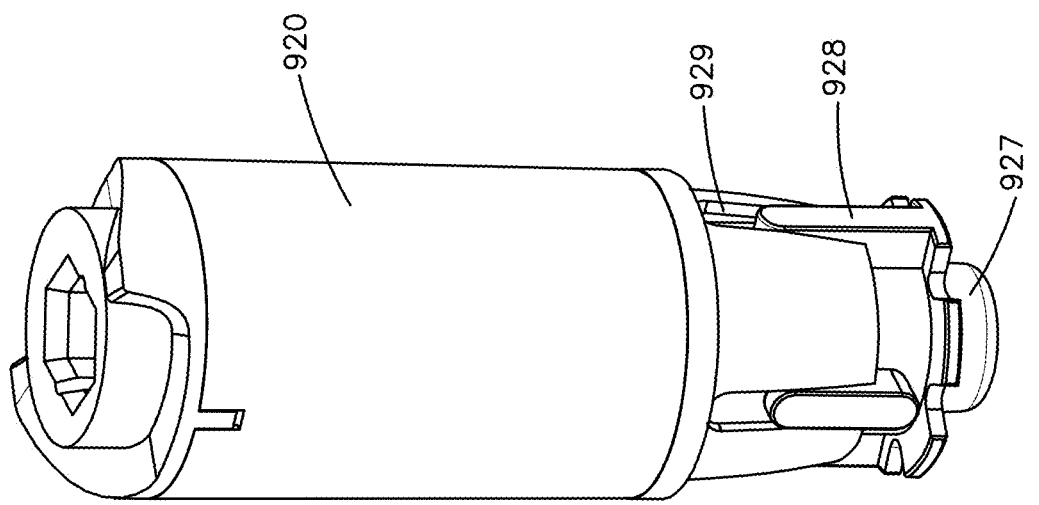

FIG. 111 is a diagram illustrating a perspective view of an example of a cartridge for use with a drug applicator.

Figure 112:
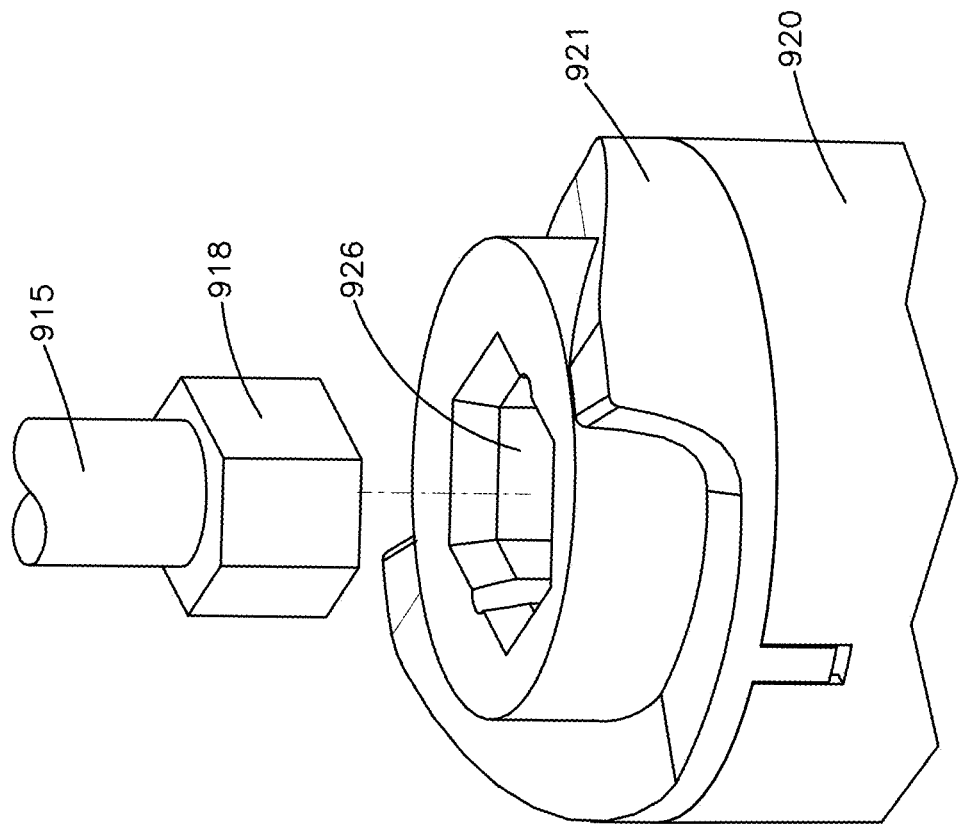

FIG. 112 is a diagram illustrating a perspective view of an example of a cam for use with a drug applicator.

Figure 113:
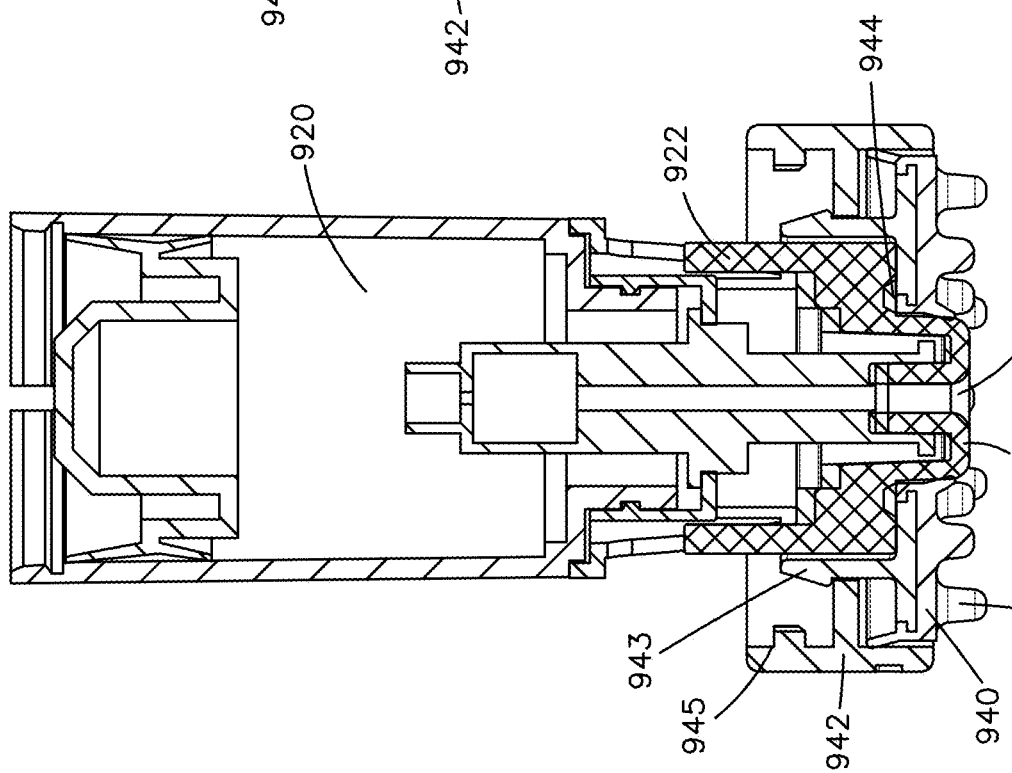

FIG. 113 is a diagram illustrating a cross-sectional view of another example of a drug applicator with a massage head.

Figure 114:
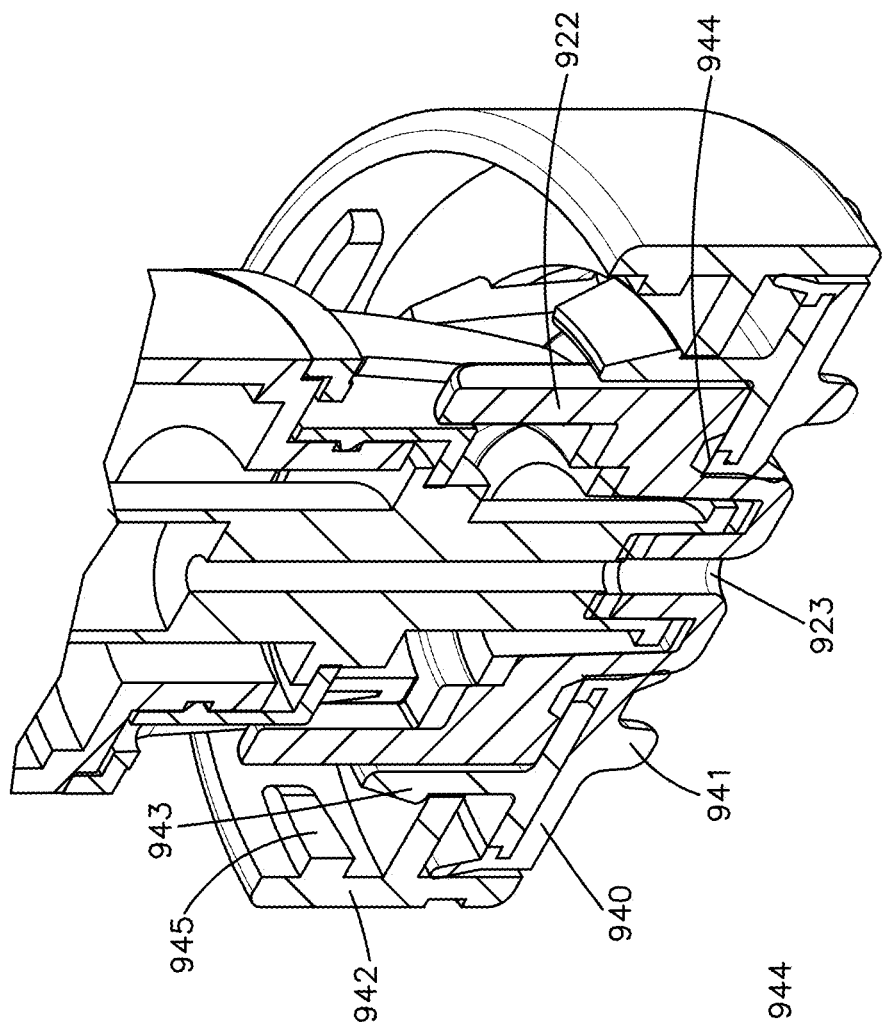

FIG. 114 is a diagram illustrating a magnified view of an example of an attachment between a drug applicator, a cartridge of the drug applicator, and a massage head of the drug applicator.

Figure 115:
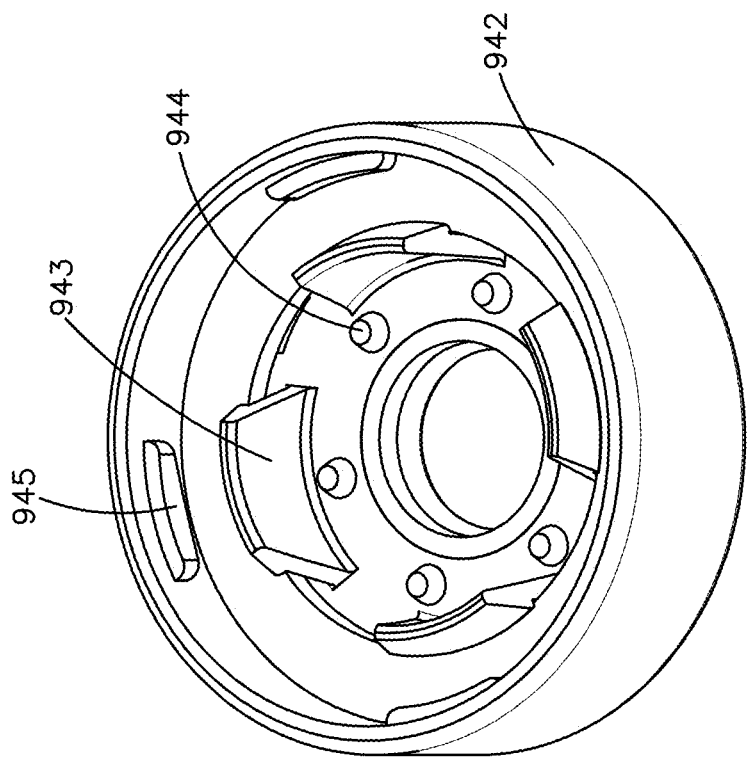

FIG. 115 is a diagram illustrating a bottom perspective view of another example of a massage head for use with the drug applicator.

Figure 116:
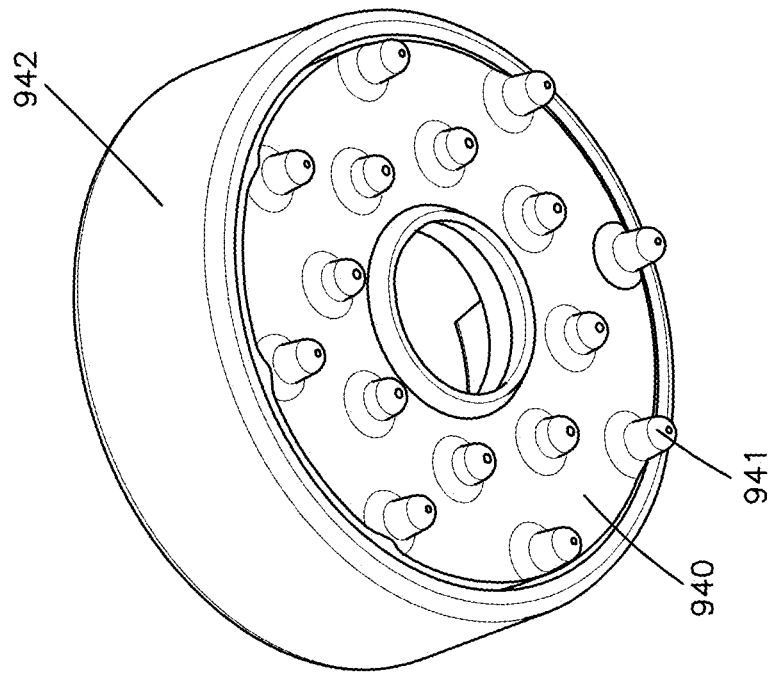

FIG. 116 is a diagram illustrating a top perspective view of another example of a massage head for use with the drug applicator.

5. DETAILED DESCRIPTION OF THE INVENTION

Before explaining at least one embodiment of the invention in detail, it is to be understood that the invention is not limited in its application to the details of construction and to the arrangements of the components set forth in the following description or illustrated in the drawings. The Figures and written description are provided to teach any person skilled in the art to make and use the inventions for which patent protection is sought. The invention is capable of other embodiments and of being practiced and carried out in various ways. Those skilled in the art will appreciate that not all features of a commercial embodiment are shown for the sake of clarity and understanding. Persons of skill in the art will also appreciate that the development of an actual commercial embodiment incorporating aspects of the present inventions will require numerous implementation—specific decisions to achieve the developer's ultimate goal for the commercial embodiment. While these efforts may be complex and time-consuming, these efforts nevertheless would be a routine undertaking for those of skill in the art having the benefit of this disclosure.

In addition, it is to be understood that the phraseology and terminology employed herein are for the purpose of description and should not be regarded as limiting. For example, the use of a singular term, such as, "a" is not intended as limiting of the number of items. Also the use of relational terms, such as but not limited to, "top," "bottom," "left," "right," "upper," "lower," "down," "up," "side," are used in the description for clarity in specific reference to the Figures and are not intended to limit the scope of the invention or the appended claims. Further, it should be understood that any one of the features of the invention may be used separately or in combination with other features. Other systems, methods, features, and advantages of the invention will be or become apparent to one with skill in the art upon examination of the Figures and the detailed description. It is intended that all such additional systems, methods, features, and advantages be included within this description, be within the scope of the present invention, and be protected by the accompanying claims.

5.1 Needling Devices

Needling devices described herein may be used for a number of different procedures including hair growth applications, wrinkle reduction, scar revision, hair removal, tattoo removal, and pigmentation. Advantages of the needling devices described this application include protecting a reusable main unit or needling device having a removable sheath or adaptor to provide ease of use by a patient or physician in performing needling operations for a number of different procedures. Methods of using the needling devices described in this application are provided in more detail in Section 5.4, below.

5.1.1 Illustrative Embodiments of the Needling Device

Referring to FIG. 1 by way of non-limiting example, and consistent with embodiments of the invention, a needling device 100, which in some embodiments may be a micropen 100 used for micro-needling, includes a body 110, a power interface 111, charging contacts 112, a first dial 113 for needle adjustment including a first measurement indicator 114, a second dial 115 for needle adjustment including a second measurement indicator 116, and a light pipe 117 for illuminating a light path in a direction parallel to the longitudinal axis of the micropen 100.

In an example, the micropen body 110 is made from an aluminum material with an anodized black or anodized satin finish, but is not limited thereto. The shape and contour of the micropen body 110, also the shape of the micropen body 110 as used in conjunction with the adaptor 200 discussed below, allows for a user to obtain improved control and handling of the micropen 100 during micro-needling operations.

Figure 1A:
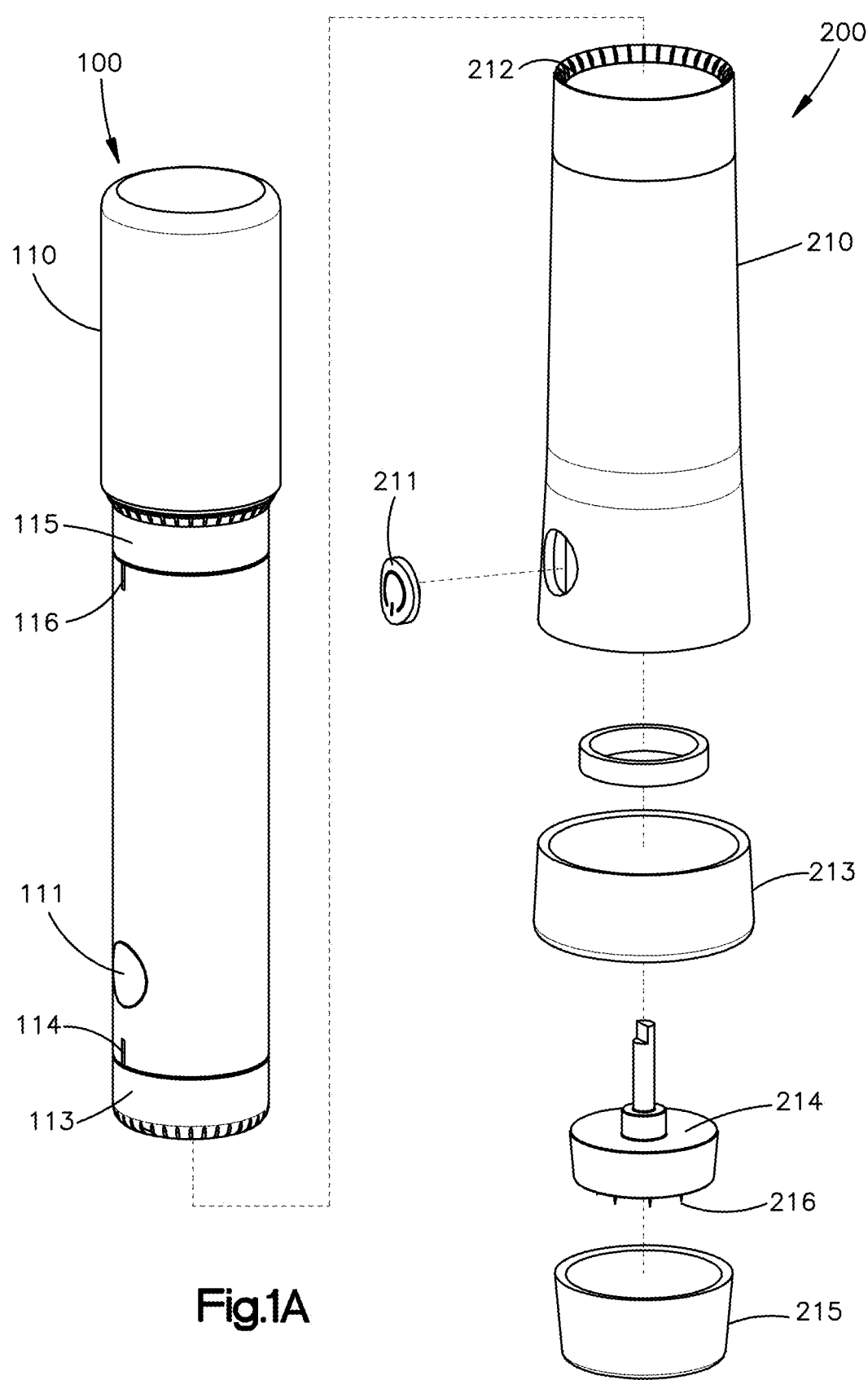
FIG. 1A is an exploded view illustrating an example of a needling device.

Referring to FIG. 1A, the micropen 100 is used with a corresponding needling adaptor 200 that includes an adaptor body 210, a power interface 211, a micropen connection section 212, a lower body 213, a needling head 214, a head covering 215, and a number of needles 216 on the needling head 214. The adaptor 200 may be formed from a variety of different materials. In an example, the adaptor 200 is formed from a polycarbonate or other plastic material. The needles 216 may also be formed from a variety of different materials, and an example includes needles formed from a high carbon steel material. The micropen 100 is inserted in the adaptor 200 prior to needling operations, and inserted such that the connection section 212 is covering the second dial 115, and the lower body 213 is covering the first dial 113. Each of the connection section 212 and the lower body 213 is independently rotatable with respect to the adaptor body 210 such that rotation of the connection section 212 allows rotation and control of the second dial 115, and the first dial 113, respectively. Further, the connection section 212 and the lower body 213 are preferably transparent such that the user may see the measurements on the first and second dials 113, 115 and corresponding measurement indicators 114, 116 while controlling each dial.

The first dial 113 and second dial 115 may be used for a variety of adjustment functions of the needles 216. Preferably the needles 216 can be adjusted in penetration depth and density. However, other adjustments may be available for a user such as needling speed. In an example, the first dial 113 is used for adjusting an indexing angle and thus the density of the needles 216 and the second dial 115 is used for adjusting the penetration depth of the needles 216. Density may be adjustable such that perforations per square area is different between one configuration and another; for example, rotation of the second dial 115 controls rotation of the needling head 214 and because needles are distributed according to different densities on the needling head 214 this controls the density of needling. However, it should be appreciated that other mechanisms for controlling the density of the needles 216 may be implemented. Further, the adaptor 200 may be available with different types of needling heads 214 such that using a first adaptor would provide a different needling density than using a second adaptor.

In an example, density control of the number of perturbations or skin perforations per square area of the target surface is available in a low density, medium density, and high density configuration for ease and simplicity to a user. The density of needling referred to herein is determined by the number of needles 216 in contact with a subject's skin at a given time during a needling operation and per square area of the subject's skin. The density may range in value and in an example the density ranges in value from the ratio of skin perforations surface area to the total skin surface area being 1% to that ratio being 40%. This ratio may also include at least 1%, at least 5%, at least 10%, at least 15%, at least 20%, at least 25%, at least 30%, at least 35%, at most 5%, at most 10%, at most 15%, at most 20%, at most 25%, at most 30%, at most 35%, or at most 40%. Thus, the first dial 113 may include indicia that correspond to a low, medium, and high density configuration, or may include percent indicia indicating the percent of skin perforation.

In an embodiment, the overall operation of the needles 216 are such that the needles automatically extend in a z-axis that is parallel with the longitudinal axis of the micropen 100. The needles 216 subsequently retract and then index through a predetermined angle, angle θ. This process then continues to repeat for a period of time until the desired needling density, as set by the first dial 113, is achieved.

Referring to FIGS. 3-8, different views of the micropen 100 are provided. The micropen 100 may include a rechargeable battery or other power unit in the upper section of the micropen body 110, a motor and drive mechanism between the first dial 113 and the second dial 115, and a printed circuit board or control circuit above the first dial 113 and at the area of power interface 111. In an example, a light pipe 117 is included on the bottom surface of the miropen 100 as shown in FIG. 8. This allows a user or operator to view the needling end of the device during a needling operation as light is projected from the light pipe 117 through the adaptor 200. FIG. 7 illustrates a solid upper surface 118 of the micropen 100 that may have a curvature or contour for design and ease of handling function.

Referring to FIGS. 9-16, different views of the micropen 100 with the adaptor 200 are provided. Specifically, referring to FIGS. 9A and 9B, the cross-sectional overlap of the adaptor 200 with the micropen 100 is illustrated.

Still referring to FIGS. 9A and 9B, the tapered shape and transparent plastic material of the head covering 215 allows a user to view the needles 216 beneath the head covering 215 during the needling operation. Referring to FIGS. 11-16, different views of the combined micropen 100 with adaptor 200 are shown.

FIGS. 17-24 illustrate different views of the needling adaptor 200 for use with the micropen needling device 100. Referring to FIGS. 17-18, the connection section 212 is configured to receive the micropen 100 to provide the combined device described above. FIG. 23 illustrates an upper surface view including the connection section 212 of the adaptor 200, and FIG. 24 illustrates a bottom surface view of the adaptor 200 including the needles 216.

Referring to FIGS. 25-40, a charging station 300 is also provided for charging and communication with the micropen 100. The micropen 100 may be directly inserted into the charging station 300 to provide the combined structure illustrated in FIGS. 25-32. The charging station 300 includes the charging station body 310, a station bottom surface 311 for placing on a table or other surface, and a station electrical connection 312, a lighting ring in the charging station 300 such that the station 300 is illuminated when the micropen 100 is inserted. Different levels of light illumination may indicate different levels of charge for the micropen 100. Further, lighting levels may indicate when charging is complete, or different colors of light may be used.

As illustrated in FIGS. 25A and 25B, the flush design of the micropen 100 when inserted into the charging station 300 provides for an aesthetically pleasing configuration and ease of handling the combined device by a user. The bottom surface 311 allows the combined device to be placed on a surface upright or stowed away when not in used.

Referring to FIGS. 33-40, different views of the charging station 300 without the micropen 100 are illustrated. The charging station 300 includes an indicator 314 for indicating power and whether charging is activated. Also, referring to FIGS. 33 and 34, an upper section 313 is configured to receive the micropen 100. It should be appreciated that communication between the charging contacts 112 and the station 300 allows for charging of the micropen 100 but also for other functions such as data transfer. Referring back to FIG. 2, the four charging contacts 112 may include power, ground, data, and overcharge contacts.

FIG. 95 is a diagram illustrating a perspective view of another example of a micropen needling device 700 (not visible), also referred to as the main unit, enclosed within a needling adaptor 800, also referred to as the sheath assembly, in an assembled state. FIG. 96 is a diagram illustrating an exploded view of the micropen needling device 700 enclosed within the needling adaptor 800 in a disassembled state.

Referring to FIG. 95, the needling device 700 is fully encapsulated within the needling adaptor 800 so that all parts of the needling device 700 are protected from the outside environment. This provides users or doctors with a device that is capable of being maintained at the most sterile conditions. For example, the needling device 700 may be used with a first needling adaptor 800 on a first subject, and then the first needling adaptor 800 may be removed and replaced with a second needling adaptor for use on a second subject while keeping the needling device 700 entirely protected from the outside environment. The needling adaptor 800 is provided in a sterile condition prior to being removed from packaging; this provides an advantage in that the system does not require a clinic, a doctor, or a user to sterilize the equipment. In another example, the needling device 700 may be used with different types of needling adaptors 800 having different types of needling arrays on the same subject. That is, a patient may use a needling adaptor 800 for hair growth applications, and subsequently use a different needling adaptor 800 for tattoo or scar removal without a need to sterilize the needling device 700 because it is fully encapsulated and protected from the outside environment during use. This provides at least prevention of cross-contamination, among other benefits such as ease of use and replacability, and reduced manufacturing costs.

Referring to FIG. 96, the needling device 700, which in some embodiment is micropen needling device 700, includes a micropen body 710, a micropen cap 720, and one or more buttons 730 for control of the needling device 700. The one or more buttons 730 may include buttons for controlling a penetration depth or a speed of the needling operation or perturbations applied to a subject's skin, an on/off power button for the needling device 700, a power control of a light tube that allows light to exit from a distal end of the needling device 700 to illuminate the perturbation region, and a trigger button, that is separate from the power button, for powering on the needling mechanism when pressed down by a user and powering off the needling mechanism when released by a user. In an example, needle penetration depth adjustment is controlled by a user rotating an adaptor cap 820 which in turn rotates the micropen cap 720 and a motor chassis 740 as described further below in reference to FIG. 98.

Still referring to FIG. 96, the needling adaptor 800 includes an adaptor body 810, an adaptor cap 820 for controlling and/or rotating the micropen cap 720, one or more buttons 830 for controlling the one or more buttons 730 of the encapsulated needling device 700, and a needle housing 840 surrounding a plurality of needles 842. The needle housing 840 may receive a transparent needle cover (not shown) having the same shape as the needle housing for covering and protecting the needles. The adaptor cap 820 and the one or more buttons 830 of the needling adaptor 800 cooperate with the micropen cap 720 and the one or more buttons 730 of the needling device 700, respectively. More specifically, in an example, the adaptor cap 820 includes a projection that interacts with a groove 722 of the micropen cap 720 (shown best in FIG. 97) so that rotation of the adaptor cap 820 causes rotation of the micropen cap 720. In addition, the one or more buttons 830 of the needling adaptor 800 cover and directly interact with the one or more buttons 730 of the needling device 700 so that a user may press the one or more buttons 830 of the needling adaptor 800 to control operations of the needling device 700 while it is encapsulated. In another example, the needling device 700 can be formed without buttons 730 and capable of connecting remotely to the needling adaptor 800 via wireless connection so that the buttons 830 of the needling adaptor 800 control the needling operations without pressing down on internal buttons.

FIG. 97 is a diagram illustrating a cross-sectional view of the needling device 700 enclosed within the needling adaptor 800.

Referring to FIG. 97, the needling device 700 further includes a battery or powering mechanism 724 for powering the device 700, a battery clip 725 for holding a position of the battery 724, and a motor 726 for powering the needling operation as described in further detail below in reference to FIGS. 99 and 100. The internal components of the needling adaptor 800 of this example include a bio-barrier 812 as an additional layer of protection and sealing of the needling device 700, and a drive shaft interface 814 that is connected to the needles 842 and removably attachable to a drive shaft 712 of the needling device 700. The interaction of the drive shaft interface 814 with the drive shaft 712, such as by a female-male attachment, allows for the needling device 700 to be securely attached to the needling adaptor 800 after it is placed within the needling device 700 and pushed fully within the needling adaptor 800. A snap feel and/or sound provides users with the assurance that the devices are secured together and ready for use. This positive engagement provides for a needle array coupling means the reduces vibration in the device and facilitates a higher quality procedure FIG. 98 is a diagram illustrating a perspective view of the inner components of the needling device 700.

Referring to FIG. 98, the inner components of the needling device 700 include the micropen cap 720, the battery 724, the battery clip 725, and the motor 726, as described above. In addition, the needling device 700 includes a motor shaft 718 that extends from the motor 720, an angled hub 716 secured to the motor shaft 718, a wobble plate 714 that is received by the angled hub 716, and the drive shaft 712 that is connected to the wobble plate 714. The inner components of the needling device 700, including at least the motor 726, the motor shaft 718, the angled hub 716, the wobble plate 714, and the drive shaft 712, are connected by a chassis 740 that is configured to hold together all components and move the components along the longitudinal axis of the needling device 700. The chassis 740 may be attached to the micropen cap 720 by a chassis pin 742 so that rotation of the micropen cap 720 in one direction moves the inner components axially in one direction towards or away from the subject's skin, and rotation of the micropen cap 720 in the opposite direction moves the inner components in the opposite direction. This in turn controls the penetration depth of the needles 842 prior to initiating the perturbation stroke of the needles 842 using the motor 726 and the corresponding actuation mechanisms 712, 714, 716, 718.

FIG. 99 is a diagram illustrating a magnified view of the actuation mechanisms 712, 714, 716, 718 of the needling device 700, and FIG. 100 is a diagram illustrating an exploded view of the actuation mechanisms 712, 714, 716, 718 of the needling device 700.

As also described above and best illustrated in FIG. 100, the motor shaft 718 extends from the motor 720, the angled shaft 716 is secured and is rotated by the motor shaft 718, the wobble plate 714, which has a rotating element 714a fixed to the angled-shaft 716 and a non-rotating element 714b connected to the drive shaft 712. The rotating element 714a and non-rotating element 714b are joined by a bearing element. As the motor shaft 718 rotates, the angled shaft 716 is rotated by the motor shaft 718. The non-rotating element 714b of the wobble plate oscillates in the plane of the motor axis, toward and away from the subject's skin surface, with each revolution of the motor shaft 718. The extent of the oscillation defines the travel of the needle holder 844 available for the needling operation.

Referring now to FIG. 101, the attachment of the needles 842 to the drive shaft 712 is more clearly illustrated. The needles 842 are arranged in an array on a needle holder 844 that is secured to the drive shaft interface 814. The drive shaft interface 814 is removably attached to the drive shaft 712 so that the axial displacement of the drive shaft 712, as described above, causes the axial displacement of the drive shaft interface 814, the needle holder 844, and the needles 842. In addition, the bio-barrier 812 may be securely attached about the needle holder 844 and configured to move axially with the needle holder 844. Other components that are illustrated include the previously described adaptor body 810, bio-barrier 812, needle housing 840, micropen body 710, actuation mechanisms 712, 714, 716, 718, and motor 726.

FIG. 102 is a diagram illustrating a cross-sectional view of the needling adaptor 800 without the needling device 700.

The needling adaptor 800 includes the adaptor body 810, having a needle housing 840, and the adaptor cap 820 that are securely attached to one another, the one or more buttons 830, the drive shaft interface 814, the needle holder 844, and the needles 842. The needling adaptor 800 is disposable and is intended for a single treatment session. The needles 842 and needle holder 844 may have a variety of different shapes and configurations. In this example, the needle holder 844 is rectangular and the needles 842 are arranged in two parallel rows.

FIGS. 103, 104, and 105 are diagrams illustrating different views of the needles 842 and needle holder 844. As illustrated in FIGS. 103-105, the needles 842 are arranged on the rectangular needle holder 844 in two parallel or substantially parallel rows that extend across the rectangular needle holder 844. Substantially parallel as used herein means in the range of plus or minus 10% In this example, there are 12 needles 842 with 6 needles 842 on a first row 846 and 6 needles 842 on a second row 847. Also, the needles 842 of the first row 846 are offset from the needles 842 of the second row 847 so that a needle on a first row 846 is horizontally between and equidistant from two needles on a second row 847. In another example, three rows or more may be used. In an example, the needles 842 are arranged in a rectangular arrangement so that the distance covered by the needles 842 in one row is greater than the distance covered by the needles 842 in one column. In another example, the needle holder may have a circular shape as illustrated in the example of FIGS. 18 and 24, and the needles 216 may be arranged on the circular shaped holder.

Advantages of the needles 842 and needle holder 844 being arranged in a rectangular configuration include allowing a user or physician the ability to view the target region during the needling operation. In another example, the shape of the needle holder allows the user to follow a more precise needling pattern of a series of straight lines that do not overlap which also provides for a quicker and more efficient needling operation in contrast to a rounded arrangement of needles or a circular needle array.

5.1.2 Aspects of the Described Embodiments of the Needling Device

In an aspect, the needling devices and needling adaptors described in all embodiments above suitable to promote hair follicle neogenesis through targeted cutaneous perturbation (TCP) of the skin (e.g., the scalp). In a specific embodiment, TCP refers to integumental perturbation of one or more epidermal layers (see, e.g., Sections 5.3 and 5.4), for example, the basal and/or suprabasal epidermal layers. In a specific embodiment, the integumental perturbation performed by the needling devices and needling adaptors described herein is followed by the application of a compound (see, e.g., Section 5.6) to the skin. Without being bound by any particular theory, TCP triggers generation of new hair follicles by induction of epithelial stem cells. See, e.g., Sections 5.3 and 5.4 for a more detailed discussion of integumental perturbation and methods of using the needling devices and needling adaptors. In other examples, the needling devices and needling adaptors or interchangeable needling adaptors with needle arrays having different configurations (such as is illustrated in the example of FIGS. 18 and 24) can be used for other applications such as wrinkle reduction, scar revision, hair removal, and tattoo removal.

In an example, the needling devices and needling adaptors of all embodiments may form a combined rechargeable, battery powered, handheld instrument. The devices are used to perform TCP by reciprocating a needle array into and out of the scalp to "injure" the scalp. The hand piece assemblies include a durable and reusable needling device and a single-use needling adaptor that also acts as a protective barrier such that the needling device is not exposed to blood or other contaminated materials.

In an example, the needling devices of all embodiments may include a sensor for detecting whether the needling adaptor is a previously used needling adaptor so as to disallow reuse of the previously used needling adaptor. The needling device and/or the needling adaptor may also include a controller for determining when the device is powered off and automatically retracting the needles and/or adjusting the needle penetration depth to the most retracted position in response to the device being powered off. The needling device may also be used in combination with guides that fit over the needle array in order to direct movement through a subject's hair; for example, the guides can be similar to hair clipper attachments. This limits the lateral movement of the needling device and guides a user's hand in moving using straight line strokes.

The adaptors of all embodiments, being a different component of the combined device, provide complete insulation of the needling device from the needles of the needling head. That is, because the adaptor is a replaceable, removable, and disposable sheath, this prevents blood contamination of the needling device and prevents cross-contamination between different users of the needling device. Equally important, these devices reduce the amount of time needed to begin a needling operation because a doctor receives a sheath or adaptor that is pre-sterilized once removed from its packaging and the sheath protects the main needling device unit from any contamination so it may be used immediately after with another sheath or adaptor. This function allows for safe and easy use of the devices.

In an example, the speed of needling may include three discrete speeds (60 Hz, 100 Hz, 140 Hz), and may range from 60 Hz to 140 Hz. The speed of needling includes at least 60 Hz, at least 70 Hz, at least 80 Hz, at least 90 Hz, at least 100 Hz, at least 110 Hz, at least 120 Hz, at least 130 Hz, at most 70 Hz, at most 80 Hz, at most 90 Hz, at most 100 Hz, at most 110 Hz, at most 120 Hz, at most 130 Hz, and at most 140 Hz. In addition, needle penetration depth adjustment may include incremental needle penetration depth adjustment (0.5 mm above skin surface—2.5 mm below skin surface). This prevents the dragging of the needle within the subject's skin so that if the needles are in the 0.5 mm retracted position above the skin, the needles are fully retracted and do not drag within the subject's skin while the device is being moved by the user. Reducing drag and having a light source lighting the target region provides for higher quality procedure and more precise, more consistent needling.

With regards to penetration depth control of the needles, a variety of different penetration depth adjustments may be available. In an embodiment, penetration depth may range from 0.5 millimeters in the retracted position to 2.5 millimeters; however, it should be appreciated that the penetration depth of the needles is available in a broader range. For example, the penetration depth may include a range from −0.5 millimeters where the needles are in a completely retracted position to a range of 5 millimeters or more. The penetration depth may include at least −0.5 millimeters, at least 0 millimeters, at least 0.5 millimeters, at least 1 millimeter, at least 1.5 millimeters, at least 2 millimeters, at least 2.5 millimeters, at least 3 millimeters, at least 3.5 millimeters, at least 4 millimeters, at least 4.5 millimeters, at most 0.5 millimeters, at most 1 millimeter, at most 1.5 millimeters, at most 2 millimeters, at most 2.5 millimeters, at most 3 millimeters, at most 3.5 millimeters, at most 4 millimeters, at most 4.5 millimeters, or at most 5 millimeters.

In one aspect, a needling device or needling adaptor described herein is suitable for disrupting skin to a penetration depth of between 30 μm to 200 μm (e.g., to a maximum depth of 30, 40, 50, 60, 70, 80, 85, 90, 95, 100, 105, 110, 120, 130, 140, 150, 160, 170, 180, 190 or 200 μm), and preferably to approximately 100-150 μm. In one aspect, a needling device or needling adaptor described herein is suitable for disrupting skin to a depth of 100 μm. In one aspect, a needling device or needling adaptor described herein is suitable for disrupting skin to a depth of 150 μm.

5.2 Applicator Devices

Examples of a needling device and other components including adaptors and charging stations have been described, and a description of fluid or drug applicators, massage heads for use with drug applicators, cartridges for use with drug applicators, and drug applicator charging stations will now be described in reference to the remaining figures. The fluid or drug applicators described herein may be used with any type of fluid. In an example, the fluid applicator is a drug applicator that is used for the application of minoxidil to a subject's scalp or for a variety of different applications using different chemicals. With respect to all embodiments of the drug or fluid applicators, it should be appreciated that any type of fluid may be used and this invention is not limited to the use of a drug. For convenience, the devices may be referred to throughout the specification as "drug applicators", "fluid applicators", or simply "applicators". Methods of using the applicator devices described in this application are provided in more detail in Section 5.4, below.

In one aspect, drug applicators may be used in combination with other agents or treatments that stimulate hair growth. For example, hair growth-promoting agents for use, alone or in combination, in accordance with this aspect include but are not limited to: agents affecting prostaglandins, such as Prostaglandin F2α analogs, e.g. latanoprost (trade name Xalatan), travoprost (trade name Travatan), tafluprost, unoprostone, dinoprost (trade name Prostin F2 Alpha), AS604872, BOL303259X, PF3187207, carboprost (trade name Hemabate); Prostamides, e.g., bimatoprost (trade names Latisse, Lumigan); Prostanoid receptor agonists, e.g. fluprostenol; Prostaglandin D2 receptor antagonists, e.g. laropiprant, AM211; Prostglandin E2 analogs, e.g. sulprostone; and EP 2 receptor agonists, e.g. butaprost; 5α-reductase inhibitors, such as, e.g., finasteride, dutasteride, turosteride, bexlosteride, izonsteride, episteride, epigallocatechin, Fluridil (Sovak et al, *Dermatol Surg.* 2002; 28(8):678-685), RU 58841 (Pan et al. Endocrine. 1998; 9(1):39-43), N,N-diethyl-4-methyl-3-oxo-4-aza-5 alpha-androstane-17 beta-carboxamide (Rittmaster et al., J Clin Endocrinol Metab. 1987; 65(1):188-193), MK-386, azelaic acid, FCE 28260, SKF 105,111; Minoxidil; ATP-sensitive potassium channel openers, e.g. diazoxide; and the hair growth-promoting agents described herein or otherwise known in the art, such as, e.g., kopexil (for example, the product Keranique™), $CaCl_2$, botilinum toxin A, adenosine, ketoconazole, DoxoRx, Docetaxel, FK506, GP11046, GP11511, LGD 1331, ICX-TRC, MTS-01, NEOSH101, HYG-102440, HYG-410, HYG-420, HYG-430, HYG-440, spironolactone, CB-03-01, RK-023, Abatacept, Viviscal®, MorrF, ASC-J9, NP-619, AS101, Metron-F-1, PSK 3841, Targretin (e.g., 1% gel), MedinGel, PF3187207, BOL303259X, AS604872, THG11331, PF-277343, PF-3004459, Raptiva, caffeine, and coffee. Other hair-growth promoting agents include arginine, isoleucine, leucine, lysine, methionine, phenylalanine, threonine, tryptophan, valine, gamma linoleic acid and polyphenol catechins, copper peptides. Other hair-growth promoting agents that can be formulated as a hair wash tonic could include but are not limited to, jojoba oil, extract of apple, saw palmetto, emu oil, beta carotene and green tea. In another aspect, the applicators may also be used in combination with drugs for alopecia being developed by SWITCH Biotech LLC.

In addition, other compounds that may be used with the applicator include compounds identified by the following company and company ID, Actelion ACT-129968 (setipiprant), Actimis AP768, Amira AM211, Amira AM461, Amgen AMG853, Array BiPharma ARRY-502, AstraZeneca AZD1981, AstraZeneca AZD8075, AstraZeneca AZD5985, Merck MK-7246, Novartis QAV680, Oxagen 00000459, Ocagen 00002417, Pulmagen ADC3680B, Shionogi S-555739, BBI-5000, SM04554, and KYTH105 (setipiprant).

In a specific embodiment, other compounds that may be used with the applicator include agents described in Section 5.6, below. In a specific embodiment, the compound(s) that may be used with the applicator is in a dose as described in Section 5.7, below.

5.2.1 Illustrative Embodiments of the Applicator Device

Referring to FIGS. 41-48, different views of the applicator 400 with the massage head 500 attached thereto are provided. The applicator 400 may be formed of one or more different materials including but not limited to polycarbonate. The massage head 500 may be formed of one or more different materials including one or more of synthetic rubber, silicone, and low durometer plastics. The applicator 400 includes an applicator body 410 and an upper covering surface 411. The details of the applicator components will be described in further detail below in reference with FIGS. 89-93. The massage head 500 includes a massage head body 510 and a number of massage nubs 511, 512. The massage nubs 511, 512 include closed nubs 512 and open nubs 511 that provide for the flow of a compound directly to the subject's scalp. The opening in the open nubs 511 is directly at the bottom of each nub 511 thus allowing direct access to the subject's scalp rather than the subject's hair.

FIGS. 49-56 illustrate different views of the applicator 400 as placed within the charging station 600. The charging station 600 includes a charging station body 610 and a charging station bottom surface 612. The bottom surface 612 may be curved with a flat area in the center to allow for the charging station 600 to stand upright on a surface or table. The station 600 may come in a variety of different colors and materials, but in an example, the charging station 600 is transparent and capable of being illuminated by light emitted from the applicator 400. As discussed in more detail below in reference with FIG. 93, the applicator 400 may include an LED ring 430 that become more illuminated as the applicator 400 becomes more charged. Accordingly, a user may detect the amount of charge to the applicator 400 based on the illuminated lighting of the transparent charging station 600.

FIGS. 57-64 illustrate different views of the charging station 600 without the applicator 400. Referring to FIG. 57, the charging station 600 includes an upper section 611 for receiving and connecting to the applicator 400. The bottom surface 612 is also illustrated in FIGS. 58 and 64. The charging station 600 is a dock that gives the applicator 400 a base to charge up. The charging station 600 can be plugged in when needed for charging.

As illustrated in FIG. 93, an LED ring 430 of the applicator 400 may interact in various ways with the charging station 600. For example, the light from the LED ring 430 may glow to indicate that it is time for a subject or user to use the device. This may vary based on the type or gender of the subject. Lifting the applicator 400 out of the charging station 600 will turn the lighting off and acknowledge the subject's progress. Once placed back in the station 600, other alerts may indicate power or fluid level issues and will also alert the subject or user of the next use period. Further, while the applicator 400 is in the station 600, the applicator 400 may be rotated to adjust the intensity of chemical dispensing. The LED ring 430 may change intensity to match the user's settings. The applicator 400 may also be controlled by connecting with a smart phone or device via Bluetooth LTE.

FIGS. 65-72 illustrate different views of a first massage head 500 without the applicator 400. Referring to FIGS. 65 and 66, the massage head 500 includes a massage head body 510, open nubs 511, closed nubs 512, massage head connecting surface 513, male connecting projections 514, and a massage head central opening 515. The connecting surface 513 is for receiving the applicator 400, and the connecting projections 514 are for connection to corresponding female connecting sections 452 of the applicator 400, as illustrated in FIG. 90. The massage head 500, also known as a smart head, is interchangeable and allows for treatment based on hair type, regeneration goals, and comfort. The open nubs 511 include dispensing tips, and in this example, there are three open nubs 511. The closed nubs 512 are for combing and massaging. The massage head 500 may also include two sensor tips that are formed of carbonized rubber material these inform when the tips are in contact with the skin and can automatically initiate activation.

FIGS. 73-80 illustrate different views of a second massage head 500b without the applicator 400. Referring to FIGS. 73 and 74, the massage head 500b includes a massage head body 510b, open nubs 511b, closed nubs 512b, a massage head connecting surface 513b, and male connecting projections 514b. The connecting surface 513b is for receiving the applicator 400, and the connecting projections 514b are for connection to corresponding female connecting sections 452 of the applicator 400, as illustrated in FIG. 90.

Referring to FIGS. 81-88, a third massage head 500c without the applicator 400 is illustrated. Referring to FIGS. 81 and 82, the massage head 500c includes a massage head body 510c, massaging nubs 511c, a massage head connecting surface 513c, male connecting projections 514c, and a massage head central opening 515c. The connecting surface 513c is for receiving the applicator 400, and the connecting projections 514c are for connection to corresponding female connecting sections 452 of the applicator 400, as illustrated in FIG. 90. This third massage head 500c aids a user in finding areas of male pattern baldness.

Referring now to FIGS. 89-90, a description of the components of the applicator 400 will be described. The applicator 400 may include a removable cartridge 450 in the central portion of the applicator 400. This cartridge 450 may be used for Minoxidil solution or other types of fluid.

The removable cartridge 450 may include female connecting sections 452 for connecting with the male sections 514 of the massage heads 500. Also, the cartridge 450 may include a transparent upper surface window and walls for showing fluid levels. Alternatively, fluid level can be communicated to the user via LED display. The cartridge 450 also preferable includes nubs that would correspond with nubs of the massage heads 500 and include open tips for excreting the fluid directly through the massage head open nubs 511.

Referring still to FIGS. 89 and 90, the drug applicator 400 includes an internal body 460 for housing the power and actuation mechanisms 462, 464. Specifically, the internal body 460 may include an actuation mechanism 462 such as a motor and actuator for controlling the rotating aspects of the massage head 500. Also, the internal body 460 may include a power mechanism 464 such as a rechargeable battery for providing power to the applicator 400. Further, the drug applicator 400 includes a dispensing mechanism for ejecting the chemical through the drug applicator 400 and massage head 500. A number of different dispensing mechanisms may be used such as an actuatable piston as used in syringes, a vacuum system for suctioning the fluid, or other pumping mechanism. While the drug applicator 400 may include a power button for turning on and off, in an example, the drug applicator 400 may turn on and off by user contact or a touch interface on the device.

Referring now to FIG. 93, the applicator 400 may include a tri-color LED array 430 and a light pipe 432. As discussed above in the second and fourth paragraphs of Section 5.2.1, the LED array 430 may interact with the charging station 600 for providing different functionalities and alerts to a user.

Referring to FIG. 94, other embodiments of the applicator 400 include a cartridge 450 that is removably attached to the top of the applicator 400 instead of the applicator upper cover 411, or a cartridge 450 that is combined with a massage head 500 to provide a combined disposable cartridge and massage head structure.

FIG. 106 is a diagram illustrating a perspective view of another example of a drug applicator 900 with a massage head 940 and a charging station 930.

Referring to FIG. 106, the drug applicator 900 includes an applicator body 910, a keypad 905 including buttons for powering and controlling the operations of the drug applicator 900, and a charging station 930 which receives the drug applicator 900 for charging. The buttons may include one or more of a power button for powering the device on and off, a speed button for controlling the speed of the massaging, and a mode button for setting a mode of the operation such as setting to a massage only mode or to a massage and dispense mode. In an example, the speed includes 3 discrete speeds: 1 Hz, 2 Hz, 4 Hz. The charging station 930 may operate using inductive charging as described in more detail in reference to FIG. 107.

FIG. 107 is a diagram illustrating a cross-sectional view of the drug applicator 900 with the massage head 940 and the charging station 930. FIG. 108 is a diagram illustrating a cross-sectional view of the drug applicator 900 with the massage head 940 and without the charging station 930.

Referring to FIGS. 107 and 108 together, the drug applicator 900 further includes a controller 912, a position sensor 913, a motor 914, a motor shaft 915, a battery or powering mechanism 916 for powering the drug applicator 900, a roller frame 911 for holding the one or more rollers 911b (illustrated in FIG. 109), a drive key 918 attached to the motor shaft 915, a cam drive 921 that receives the drive key 918 and supports the rollers 911b, an internal cavity 919 for receiving a cartridge 920 which contains a liquid that is dispensable, a cartridge actuator 922 that is configured to be actuated for dispensing the liquid from the cartridge 920, and an LED ring 917 that is formed around an upper circumferential portion of the applicator body 910 so that it is visible 360 degrees about the applicator body 910 while the applicator 900 is being charged in the charging station 930. In an example, the LED ring 917 may indicate if the device is powered on and may range in intensity of light in response to the level of charge of the device; that is, the light may incrementally increase as the device becomes more charged in the charging station 930.

Referring to FIG. 107 alone, the drug applicator 900 may be charged by inductive charging; that is, using an electromagnetic field to transfer energy from the charging station 930 to the drug applicator 900 through electromagnetic induction. The charging station 930 may include a charge coil 932 and the drug applicator 900 may include a corresponding coil 934 for interacting with the charge coil 932 of the charging station 900 and charging the drug applicator 900. In this example, the battery 916 is a rechargeable battery and the use life per battery charge is 14 treatments, each treatment cycle lasting approximately five minutes. Referring to FIG. 108 alone, the cartridge 920 also includes a nozzle 927 for dispensing the liquid and an orifice 923 extending through the nozzle 927 and connected to the passageway through which the liquid is dispensed from the cartridge 920. Also included with the drug applicator 900 is a removable massage head 940 with one or more massage nodules 941 for massaging a subject's skin.

The dispensing and massaging process will now be described in reference to FIGS. 109-112 with a focus on the liquid dispensing mechanism of the drug applicator 900 and the cartridge 920 placed within the drug applicator 900. As previously described, the cartridge 920 includes a reservoir for holding a liquid, for example a drug, that is dispensed by the drug applicator 900. In this example, the massaging and dispensing operations of the drug applicator 900 are actuated by the same motor 914 and the motor shaft 915 attached to the motor 914.

Referring to FIG. 109, a magnified perspective view of the interaction between the roller frame 911 and the cam drive 921 is illustrated. The cam drive 921 has an upper surface for receiving rollers 911b of the roller frame 911. The upper surface includes a flat or substantially flat, least-raised portion and gradually rises to a most-raised portion. The rollers 911b and roller frame 911 remain fixed while the cartridge 920 is rotated by the motor shaft 915. In another example, the drug applicator 900 operates without a roller frame 911 or rollers 911b, and one or more bumps or molded features are formed on the drug applicator 900 for interaction with the cam drive 921. In fact, molded features might obviate the need for rollers 911b, if friction between molded features on the housing and the cam surfaces on the cartridge is adequately low.

FIG. 112 is a diagram illustrating a perspective view of the cam drive 921 for use with the drug applicator 900. Referring briefly to FIG. 112, the cartridge 920 includes a receptacle 926 for receiving a drive key 918 at the end of the shaft 915. The drive key 918 remains within the receptacle 926 throughout the entire rotation of the cartridge 920 but may move up and down within the receptacle 926 depending on the position of the cartridge 920.

Referring back to FIG. 109, it should be appreciated that, because the roller frame 911 and the rollers 911b are fixed, when the rollers 911b are above the flat, least-raised portion, the cartridge simply rotates. As the cartridge 920 is rotated further by the motor shaft 915 so that the cam drive 921 is beneath the rollers 911b at the gradually raised portion of the cam drive 921, the top of the cartridge is pressed down and towards the cartridge actuator 923 to begin dispensing. Once the rollers 911b reach the most raised portion of the cam drive 921, the cartridge 920 is in the most compressed position so that the dispensing cycle is fully actuated. As the cartridge 920 is then rotated in the counter-direction, the cartridge 920 is decompressed as the top of the cartridge returns to its original position. The rotation angle of the cartridge 920 may be sensed by the position sensor 913 which may include three opto-electronic devices, either interrupter or reflector, which sense moving flags or marks for determining the stage of a cycle or the quantity of liquid or drug that is dispensed, and send such data to the controller 912. The controller 912 communicates with the motor 914 for controlling the massaging and dispensing operations.

FIG. 110 is a diagram illustrating a cross-sectional view of the cartridge 920 for use with the drug applicator 900. In an example, the cartridge 920 may be sold and packaged separately from the drug applicator 900 and may be refillable with fluid or liquid. In this example, the cartridge 920 may include a conventional, off-the-shelf container with a piston 925 that may be placed within the cartridge 920 when the cartridge 920 needs to be refilled. The cartridge 920 includes an opening 924 extending through the reservoir of the cartridge 920 through which liquid is suctioned to the nozzle 927 and ultimately dispensed through the orifice 923 of the nozzle 927. The cartridge actuator 922 interacts with the cartridge 920 as explained in more detail in reference to the suctioning operation and FIG. 111.

FIG. 111 is a diagram illustrating a perspective view of the cartridge 920. As shown in FIG. 111, the cartridge actuator 922 includes one or more ribs 928 that are received in slots 929 formed at the bottom portion of the cartridge 920 to ensure that actuator 922 and cartridge 920 rotate together and not relative to each other. As described above, once the cartridge 920 is rotated so that the rollers 911b are above the raised portion of the cam drive 921, the body of the cartridge 920 is pressed down and into the cartridge actuator 921. Because the cartridge actuator 922 including the nozzle 927 is fixedly attached in the longitudinal direction (up and down) to the massage head 940 which is fixedly attached in the longitudinal direction (up and down) to the drug applicator 920, the cartridge actuator 922 does not move up and down within the drug applicator 900. Rather, the body of the cartridge 920 is pressed so that the top of the cartridge 920 is pushed down into the cartridge actuator 922. This pressing motion dispenses drug. On counter-rotation, cartridge 920 returns to full length and pump 924 refills with drug from the reservoir. Piston 925 slides to decrease reservoir volume. During operation, the entire inner reservoir does not receive any air thus the cartridge 920 functions as an airless dispenser.

The massaging operation will now be described in reference to FIGS. 113 and 114. FIG. 113 is a diagram illustrating a cross-sectional view of the drug applicator 900 with the massage head 940. FIG. 114 is a diagram illustrating a magnified view of the attachment between the drug applicator 900, the cartridge 920, and the massage head 940.

Referring to FIGS. 113 and 114, the cartridge 920 and cartridge actuator 922 including the nozzle 927 and orifice 923 are shown. The nozzle 927 is fixedly attached to the massage head 940. As the cartridge 920 including the cartridge actuator 922 are rotated, the massage head 940 is also rotated causing the massaging operation. The massage head 940 is rotatably attached to a massage head holder 942 by a bearing having one or more plates 943 that slide on the surface of the massage head holder 942. The massage head holder 942 including the attached massage head 940 and the cartridge 920 are removably attached to the drug applicator 900 by a collar including one or more securing elements 945. A user can remove and replace the massage head 940 and attached portions for swapping an empty cartridge 920 with a new, full cartridge 920. The massage head 940 also includes cartridge securing nubs 940 for receiving the bottom of the cartridge actuator 922. More specifically, as best shown in FIG. 111, the cartridge actuator 922 includes a star-shaped bottom surface below the bars 928 and forms gaps. Each of the gaps can have a cartridge securing nub 944 placed within it so that the massage head 940 is secured to the cartridge 920 and both are rotated together. Accordingly, the rotating motion is consistently applied to the whole cartridge 920 and the massage head 940 while the massage head holder 942 does not rotate and is fixedly attached to the drug applicator 900.

Referring to FIGS. 115 and 116, the massage head may be two parts—a mechanical disc and a rubber portion—or, in another example, the message head may be a single part with an elastomer molded over a rigid disc. In these figures, a magnified illustration of the massage head 940, massage nodules 941, the massage head holder 942, the bearing plates 943, the cartridge securing nubs 944, and the securing elements 945 is provided. It should be appreciated that any of the shapes, types, designs, or configurations of massage heads described above throughout this application may be used with this drug applicator 900 and a number of different types of massage heads 940 are interchangeable.

It should be appreciated that the keypad 905, the controller 912, and the position sensors 913 can work together for programming the massaging and/or massaging and dispensing cycles of the drug applicator 900.

5.2.2 Aspects of the Described Embodiments of the Applicator Device

In all embodiments of the drug applicators described above, the drug applicators may be programmed remotely using an external or mobile device via Bluetooth® or other wireless communications. In an example, the total dose is 1 ml per treatment and is delivered in five pulses of 0.2 ml each (or an appropriate number of smaller pulses). Each pulse is a full-stroke dispenser actuation. In an example, the drug applicators may be programmed to perform a Massage+Dispense cycle for 1 minute that is followed by a Massage-only cycle for 5 minutes. A number of different programmable cycles may also be selected by a user.

It should be appreciated that a number of different compounds, liquids or drugs may be used with the drug applicators and cartridges, and cartridges may be sold separately including a variety of different compounds, liquids or drugs. In addition to those described above in the second paragraph of Section 5.2, a number of different drugs or compounds may be used including proteasome inhibitor such as lactacystin, a peptidyl aldehyde, or pentoxyfilline (PTX), and the compounds described in Section 5.6, below.

For example, water cartridges may be used for practicing or a cartridge including a healing solution may be used by those who have had micro-needling procedures. Further, a special cleaning cartridge can be provided for cleaning the applicator systems, among other types of fluid and viscous material cartridges. Cartridges may be 14 milliliters in volume to last for approximately two weeks or more; however, other volumes should be appreciated by those of skill in the art. For example, the volume of the cartridge may range from 5 milliliters to 20 milliliters and the volume includes at least 5 milliliters, at least 6 milliliters, at least 7 milliliters, at least 8 milliliters, at least 9 milliliters, at least 10 milliliters at least 11 milliliters, at least 12 milliliters, at least 13 milliliters, at least 14 milliliters, at least 15 milliliters, at least 16 milliliters, at least 17 milliliters, at least 18 milliliters, at least 19 milliliters, at most 6 milliliters, at most 7 milliliters, at most 8 milliliters, at most 9 milliliters, at most 10 milliliters, at most 11 milliliters, at most 12 milliliters, at most 13 milliliters, at most 14 milliliters, at most 15 milliliters, at most 16 milliliters, at most 17 milliliters, at most 18 milliliters, at most 19 milliliters, and at most 20 milliliters. Alternative design embodiments for the cartridges may include smaller sized cartridges providing for daily or unit dosing such as with metered dosing for syringes.

In an aspect, it should be appreciated that advantages of the applicators include massaging and parting hair simultaneously while dispensing a chemical, omni-directional movement of the massage heads, a charging station acting as a light pipe and luminous display, buttonless powering, remote control and smart phone application control and monitoring, among other features. A major concern with the use of minoxidil is that it is often mostly applied to the hair rather than directly to the scalp. This is ineffective and inefficient use of the compound as minoxidil must reach the surface of the skin for optimal effect. The applicators deliver drug directly to the skin and the massage mode spreads the drug over the skin providing for more consistent and evenly distributed administration of the drug. A problem with minoxidil administration is that it is typically delivered to the hair and not the scalp. Accordingly, among other advantages, the described drug applicators provide a more effective means of applying the compound to a subject's scalp.

In another aspect, it should be appreciated that the cartridges described in all embodiments above may include a two-chamber or multi-chamber cartridge for housing and dispensing two or more drugs separately, or mixing two or more drugs and dispensing the two or more drugs together. Further, all embodiments of the applicators described above include an applicator that is capable of detecting information related to an inserted cartridge by detecting labeling provided on the inserted cartridge using RFID technology. For example, the drug applicator is capable of detecting any one or more of (a) whether a cartridge is provided by the same manufacturer of the drug applicator device or a different manufacturer, (b) what type of compound is in the cartridge, for example, a Minoxidil-5% compound for men or Minoxidil-2% compound for women, (c) how much compound is left in the cartridge, and (d) the usage history of the cartridge, for example, whether this is the first time that this cartridge has been inserted in a drug applicator device or the number of times this cartridge was previously inserted in a drug applicator device.

5.3 Integumental Perturbation

In a specific embodiment, a needling device and/or a needling adaptor are suitable for performing integumental perturbation on a subject. In a specific embodiment, a mobile app described herein is suitable for measuring integumental perturbation on a subject. In certain aspects, the needling device and/or adaptor is used in a fashion that exerts control over the extent of integumental perturbation (e.g., targeted cutaneous perturbation (TCP)) and/or control over the way in which the integumentally perturbed skin heals. In one embodiment, integumental perturbation causes only superficial wounding to the area of skin on which hair growth is desired. In a particular embodiment, the extent of wounding is minimized by controlling the depth of integumental perturbation. For example, integumental perturbation can be controlled to limit perturbation to part or all of the epidermis, to part or all of the stratum corneum, or deeper into the papillary dermis, reticular dermis, and/or hypodermis. The occurrence of pinpoint bleeding would indicate removal of the stratum corneum, epidermis (or part thereof) and portions of the upper layer of the dermis, such as the superficial papillary dermis. The occurrence of increased bleeding would indicate deeper penetration (and thus perturbation) into the deeper papillary dermis and reticular dermis layer.

In one embodiment, integumental perturbation does not remove the epidermis. In some embodiments, integumental perturbation achieves removal of part of the epidermis. In some embodiments, integumental perturbation removes the entire epidermis. In some embodiments, integumental perturbation removes all of the epidermis and part of the dermis. In some embodiments, integumental perturbation removes part of the stratum corneum. In some embodiments, integumental perturbation removes the stratum corneum. In some embodiments, integumental perturbation removes part of the papillary dermis. In some embodiments, integumental perturbation removes part of the more superficial papillary dermis. In some embodiments, integumental perturbation removes part of the deeper papillary dermis. In some embodiments, integumental perturbation removes the papillary dermis. In some embodiments, integumental perturbation removes the reticular dermis, or part of the reticular dermis. The depth of integumental perturbation depends on the thickness of the skin at a particular treatment area. For example, the skin of the eyelid is significantly thinner than that of the scalp. The occurrence of pinpoint bleeding indicates that the epidermis and portions of the dermis have been removed. Deeper penetration can result in much more bleeding, and the perturbation can go as deep as the hypodermis.

In particular embodiments, integumental perturbation is done to a clinical endpoint of pinpoint bleeding. In some embodiments, the depth reaches the level of blood vessels of the follicular papilla. In some embodiments, the depth does not go deeper than the level of blood vessels of the capillary loops in the dermal papilla, e.g., the area of papillary dermis in between rete pegs. In some embodiments, integumental perturbation does not penetrate the dermis. In some embodiments, integumental perturbation does not completely remove all, or in some embodiments, most, of the hair follicles in an area of treated skin. In one embodiment, integumental perturbation does not penetrate the reticular dermis. In one embodiment, integumental perturbation does not penetrate more than halfway through the papillary dermis.

In some embodiments, integumental perturbation penetrates the skin to a depth of between 5 and 40 µm, 40 and 100 µm, 30 and 200 µm, 50 and 150 µm, 70 and 130 µm, 80 and 120 µm, 90 and 110 µm, 95 and 105 µm, or 100 and 150 µm.

In some embodiments, integumental perturbation penetrates the skin to a depth of at least 30 µm. In some embodiments, integumental perturbation penetrates the skin to a depth of 30 µm. In some embodiments, the device penetrates the skin to a depth of 50 µm. In some embodiments, integumental perturbation penetrates the skin to a depth of 60 µm. In some embodiments, the device penetrates the skin to a depth of 30-100 µm. In some embodiments, integumental perturbation penetrates the skin to a depth of 60-100 µm. In some embodiments, integumental perturbation penetrates the skin to a depth of 60-200 µm. In some embodiments, integumental perturbation penetrates the skin to a depth of 100 µm. In some embodiments, integumental perturbation penetrates the skin to a depth of 100-150 µm. In some embodiments, integumental perturbation penetrates the skin to a depth of 150 µm. In some embodiments, integumental perturbation penetrates the skin to a depth of 100-200 µm. In some embodiments, integumental perturbation penetrates the skin to a depth of 30-200 µm. In some embodiments, integumental perturbation penetrates the skin to a depth of 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 µm. In some embodiments, the maximum depth of penetration is, e.g., 30, 40, 50, 60, 70, 80, 85, 90, 95, 100, 105, 110, 120, 130, 140, 150, 160, 170, 180, 190 or 200 µm.

In some embodiments, integumental perturbation penetrates the skin to a depth of 100-500 µm. In some embodiments, integumental perturbation penetrates the skin to a depth of less than 500 µm. In some embodiments, integumental perturbation penetrates the skin to a depth of 500-1000 µm. In some embodiments, integumental perturbation penetrates the skin to a depth of about 1 mm. In some embodiments, integumental perturbation penetrates the skin to a depth of about 1 mm or more. In some embodiments, integumental perturbation penetrates the skin to a depth of about 2 mm. In some embodiments, integumental perturbation penetrates the skin to a depth of about 2 mm or more. In some embodiments, integumental perturbation penetrates the skin to a depth of 1 mm to 3 mm. In some embodiments, integumental perturbation penetrates the skin to a depth of 1 mm to 5 mm. In a particular embodiment, integumental perturbation does not exceed 500 µm. In a particular embodiment, integumental perturbation does not exceed 1 mm. In a particular embodiment, the depth of penetration of the skin by the device does not exceed 2 mm.

In a specific embodiment, integumental perturbation removes the first 10-30 µm of these dead skin cells.

In a specific embodiment, integumental perturbation removes the stratum corneum and part or all of the epidermis by removing the first 30-100 µm of the skin. This is not deep enough to remove the sebaceous gland, bulge, or hair papilla of existing follicle structures. The removal of the epidermis can be detected by the appearance of a shiny, smooth, whiteish layer of skin.

In a specific embodiment, integumental perturbation removes the stratum corneum, all of the epidermis, and disrupts the papillary dermis (e.g., between 100 µm and 150 µm of the skin). Disruption of the papillary dermis can be detected by the appearance of small pinpoints of blood in the treated area.

In a specific embodiment, integumental perturbation removes the stratum corneum, the full epidermis, and part of the dermis down to approximately 200 µm.

In a specific embodiment, the integumental perturbation is performed in a method of use described in Section 5.4.

5.4 Methods of Use

The devices described herein are suitable for achieving one, two, or more biological outcomes described in Section 5.4.5(a). Without being bound by theory, the devices described herein can induce hair follicle neogenesis, and can also stimulate, activate, and reorganize follicular structures in order to promote hair growth. Many conventional pharmacologic treatments for hair growth promotion (e.g., agents described in Section 5.6, below) encourage the switch from vellus to terminal hair. In a specific embodiment, the devices described herein are suitable for promoting the formation of stimulated, activated and reorganized hair follicle structures which correlate with increased vellus hair, if not terminal hair. By increasing the number of stimulated and activated hair follicles, and vellus hair or terminal hair, the devices described herein may be suitable for providing additional substrates for the action of these pharmacologic treatments. Thus, in certain aspects, devices described herein are suitable for increasing hair, increasing hair thickness, and/or yielding longer lasting hair. Accordingly, such treatments may be more effective, efficient, cost-effective, and user friendly as compared to the pharmacologic treatment alone. For example, fewer treatments may be required. The hair that results may be more cosmetically satisfactory, longer lasting, thicker, more uniform, longer, and properly pigmented hair. For example, in certain aspects, the needling devices and/or needling adaptors described herein, when used in combination with administration of a pharmacologic treatment, are suitable for yielding a 1.25-fold, 1.5-fold, 2-fold, 2.5-fold, 3-fold, 3.5-fold, or 4-fold or more increase in one or more of the biological outcomes described in Section 5.4.5(a) as compared to treatment with the pharmacologic treatment alone. For example, in a specific embodiment, a method of treatment described herein comprising integumental perturbation (e.g., by a needling device and/or adaptor described herein) and administration of a pharmacologic treatment (e.g., an agent described in Section 5.6, below) yields a 1.25-fold, 1.5-fold, 2-fold, 2.5-fold, 3-fold, 3.5-fold, or 4-fold or more increase in one or more of the biological outcomes described in Section 5.4.5(a) as compared to treatment with the pharmacologic treatment alone (i.e., without the integumental perturbation step). In a specific embodiment, the needling devices and/or needling adaptors described herein, when used in combination with administration of a pharmacologic treatment, are suitable for yielding one or more of the biological outcomes described in Section 5.4.5(a) in at least 5%, 10%, 20%, 30%, 40%, 50%, 60%, 70%, 80%, 90%, or 98% of the time that a control method requires to achieve the one or more biological outcomes. In a specific embodiment, the needling devices and/or needling adaptors described herein, when used in combination with administration of a pharmacologic treatment, are suitable for yielding one or more of the biological outcomes described in Section 5.4.5(a) in at most 5%, 10%, 20%, 30%, 40%, 50%, 60%, 70%, 80%, 90%, or 98% of the time that a control method requires to achieve the one or more biological outcomes. In a specific embodiment, the control method is a method comprising microdermabrasion and administration of an agent (e.g., an agent described in Section 5.6, below). In a specific embodiment, the control method is a method of treatment with the pharmacologic treatment alone (i.e., without the integumental perturbation step). The synergistic effect of the integumental perturbation and administration of an agent described herein may be measured as an improvement over a control subject (or a control skin site on the same subject) receiving the agent and not the integumental perturbation.

5.4.1 Methods of Using the Needling Device

In an example, methods of using a needling device include providing a needling device, having a sheath assembly with a needle array and a main unit including a motor for driving the needle array, opening the sheath assembly and placing the main unit within the sheath assembly so that the main unit is fully encapsulated and protected from the outside environment; and powering on the needling device. The method may further include removing the sheath assembly and replacing the sheath assembly with another sheath assembly having a different needle array.

For example, a needle array having a rectangular configuration may be provided on a first sheath adaptor that is used by a physician on a patient for hair growth applications. After use, the first adaptor may be replaced by a second sheath adaptor having a different needle array configuration, for example, a circular needle array configuration. The needling device may be used on different parts of one patient's skin without a need to clean the needling device because it is fully encapsulated within the adaptor sheath. Also, the needling device may be used on different patients. For example, a physician may use the first needling adaptor with the device on a first patient and then remove and replace the first adaptor with a second needling adaptor for use on a second patient. As described above in reference to the description of the needling devices, a number of different procedures may be conducted such as procedures for hair growth applications, wrinkle reduction, scar revision, hair removal, tattoo removal, and pigmentation.

In a specific embodiment, the needling device is used in a method of treatment described in Section 5.4.5.

5.4.2 Methods of Using the Applicator Device

In an example, methods of using applicator devices include providing an applicator comprising having a housing, a drug delivery cartridge carried by the housing, and a massage head which is mounted on the housing, powering on the applicator; and dispense a drug automatically by a dispensing mechanism that is linked to movement of the massage head or by any other dispensing mechanism. In an example, the applicator devices are programmed by a physician or any user to follow a preset cycle of massage-only or massage and dispense; for example, a 5-minute massage cycle is followed by a 1-minute massage and dispense cycle. The device may be programmed from a keypad on the device or wirelessly using an external device.

The method may further include removing the massage head and attached drug delivery cartridge; and replacing the massage head and attached drug delivery cartridge with another massage head having another drug delivery cartridge and other massage head nodules having a different nodule arrangement. The method may further include receiving notifications from and interacting with the applicator using a remote user interface.

In a specific embodiment, the applicator device is used in a method of treatment described in Section 5.4.5.

5.4.3 Methods of Using the Needling Device and Applicator Device Together

A method of using needling devices and drug applicators together for stimulating hair growth, may include providing a needling device having a sheath assembly including a needle array; and a main unit comprising a motor for driving the needle array; providing a drug applicator for drug delivery and massaging, including a housing; a drug delivery cartridge carried by the housing; and a massage head which is mounted on the housing for massaging a subject's skin; using the needling device to perform targeted cutaneous perturbation for disrupting a layer of a human scalp; and after using the needling device, using the drug applicator for applying a drug to the disrupted layer of the human scalp.

The method may further include disrupting the layer of the human scalp that is the basal or suprabasal epidermal layer, with the drug that is being applied being minoxidil or a proteasome inhibitor including lactacystin, a peptidyl aldehyde, or pentoxyfilline (PTX) or a compound described in Section 5.6.

In a specific embodiment, the needling device and applicator device are used in a method of treatment described in Section 5.4.5.

5.4.4 Mobile App and Methods of Use in Combination with the Needling Device and/or the Applicator Device A mobile app may be used to control and provide feedback to a physician or a user and may be used in combination with each of the needling devices or fluid applicators. For example, a user may control all aspects of the needling device and applicator device including needle depth, needling speed, length of needling cycle, applicator massaging speed, length of massaging cycle, amount of fluid dispensed, speed of dispensing, and other aspects of a needling, massaging, and dispensing operation as applicable to the devices described in this application. The app may allow a user to customize a needling, massaging, and dispensing procedure so that the needler is controlled according to preset parameters, followed by a cycle of massaging according to preset parameters, and followed by a cycle of dispensing a fluid according to preset parameters.

The mobile app may also be used to provide notifications to a physician or a user. For example, the app may notify a user if a procedure has not been performed for a period of time, whether it is time for their next procedure, if a fluid cartridge needs to be replaced, how much fluid is remaining in a fluid cartridge, the current depth of needles in a needle array, the shape of the needle array configuration, along with a number of other programmable parameters of each of the needling devices and applicator devices.

In a specific embodiment, the needling device, applicator device, and/or mobile app are used in a method of treatment described in Section 5.4.5.

5.4.5 Methods of Prophylactic and Therapeutic Use

The devices and/or mobile apps described herein are suitable to achieve one or more biological outcomes described Section 5.4.5(a). Accordingly, provided herein is a method of treatment comprising use of (i) a needling device and/or a needling adaptor described herein; and/or (ii) an applicator device described herein, on an area of skin of a subject in need thereof, wherein the method of treatment achieves in the subject one or more biological outcomes described in Section 5.4.5(a). In a specific embodiment, the method further comprises use of a mobile app described herein.

In a specific embodiment, provided herein is a method of treatment, comprising (a) integumental perturbation of an area of skin of a subject in need thereof, wherein the integumental perturbation is performed by a needling device and/or adaptor described herein; and (b) after a first period of time, administering to the subject a first pharmaceutically effective dose of an agent described in Section 5.6 or formulation thereof, wherein the method of treatment achieves one or more biological outcome described in Section 5.4.5(a). In a specific embodiment, the method further comprises: (c) after a second period of time, administering to the subject a second pharmaceutically effective amount of the agent or formulation thereof. In a specific embodiment, step (c) of the method is repeated 1, 2, 3, 4, 5, 6, 7, 8, 9, 10 or more times or until an outcome described in Section 5.4.5(a) is achieved. In a specific embodiment, the integumental perturbation is as described in Section 5.3.

In a specific embodiment, provided herein is a method of treatment, comprising administering a first pharmaceutically effective dose of an agent described in Section 5.6 or formulation thereof to an area of skin of a subject in need thereof, wherein the area of skin is integumentally perturbed. In a specific embodiment, the agent or formulation thereof is administered to the subject after a first period of time, wherein the first period of time is the time since the skin was integumentally perturbed. In a specific embodiment, the method further comprises: (c) after a second period of time, administering to the subject a second pharmaceutically effective amount of the agent or formulation thereof. In a specific embodiment, step (c) of the method is repeated 1, 2, 3, 4, 5, 6, 7, 8, 9, 10 or more times or until an outcome described in Section 5.4.5(a) is achieved. In a specific embodiment, the integumental perturbation is as described in Section 5.3.

In a specific embodiment, a method of treatment provided herein further comprises use of a mobile app described herein. In a specific embodiment, the mobile app is suitable for determining one or more of the biological outcomes described in Section 5.4.5(a).

In a specific embodiment, the area of skin is an area of a subject in which hair growth is desired, for example, the scalp, the face (e.g., the eyebrow, eyelashes, upper lip, lower lip, chin, cheeks, beard area, or mustache area), or another part of the body, such as, e.g., the chest, abdomen, arms, armpits (site of auxiliary hair), legs, or genitals. In a specific embodiment, the area of skin is the head. In a specific embodiment, the area of skin is the scalp. In some embodiments, the area of skin is a balding scalp. In a specific embodiment, the area of skin is not on the face. In a specific embodiment, the area of skin is not on an area of the skin that is normally covered with only, or mostly, vellus hair. In a specific embodiment, hair restoration to a wounded or scarred part of the skin is desired and/or scar revision is desired. Thus, in a specific embodiment, the area of skin is a wounded or scarred part of the skin. In a specific embodiment, the scar is caused by surgery, such as a face lift, skin graft, or hair transplant.

In another embodiment, tattoo removal is desired. Thus, in a specific embodiment, the area of skin is a tattooed area of the skin.

In another embodiment, reduction in the visibility of a wrinkle is desired. Thus, in a specific embodiment, the area of skin is a wrinkled area of the skin.

In another embodiment, alteration in the pigmentation of skin is desired. Thus, in a specific embodiment, the area of skin is an area of the skin with altered pigmentation as compared to the majority of the pigmentation of the skin of the subject.

In a specific embodiment, the area of skin is an area of skin of any desired size, for example, between 0-3 mm in width (e.g., 1 mm, 2 mm, 3 mm, or greater), 0-2 cm in width (e.g., 1 cm, 1.5 cm, and 2.0 cm), or greater (for example, up to 10%, 30%, 50%, 70%, 90%, or 100% of a subject's skin). Optionally, the area of skin is interfollicular.

In a specific embodiment, the first period of time is less than 1 minute, 2 minutes, 3 minutes, 4 minutes, 5 minutes, 10 minutes, 15 minutes, 20 minutes, 25 minutes, 30 minutes, 45 minutes, 60 minutes, 3 hours, 6 hours, 12 hours, 24 hours, 2 days, 3 days, 4 days, 5 days, 6 days, 7 days, 8 days, 9 days, 10 days, 11 days, 12 days, 13 days, 14 days, 3 weeks, or 4 weeks. In a specific embodiment, the first period of time between is at least 1 minute, 2 minutes, 3 minutes, 4 minutes, 5 minutes, 10 minutes, 15 minutes, 20 minutes, 25 minutes, 30 minutes, 45 minutes, 60 minutes, 3 hours, 6 hours, 12 hours, 24 hours, 2 days, 3 days, 4 days, 5 days, 6 days, 7 days, 8 days, 9 days, 10 days, 11 days, 12 days, 13 days, 14 days, 3 weeks, or 4 weeks. In a specific embodiment, the first period of time between is at most 1 minute, 2 minutes, 3 minutes, 4 minutes, 5 minutes, 10 minutes, 15 minutes, 20 minutes, 25 minutes, 30 minutes, 45 minutes, 60 minutes, 3 hours, 6 hours, 12 hours, 24 hours, 2 days, 3 days, 4 days, 5 days, 6 days, 7 days, 8 days, 9 days, 10 days, 11 days, 12 days, 13 days, 14 days, 3 weeks, or 4 weeks.

In a specific embodiment, the agent is administered to the subject via an applicator device described herein.

In a specific embodiment, the agent is administered to the area of skin on the subject on which the needling device was used.

In a specific embodiment, the second period of time is less than 1 minute, 2 minutes, 3 minutes, 4 minutes, 5 minutes, 10 minutes, 15 minutes, 20 minutes, 25 minutes, 30 minutes, 45 minutes, 60 minutes, 3 hours, 6 hours, 12 hours, 24 hours, 2 days, 3 days, 4 days, 5 days, 6 days, 7 days, 8 days, 9 days, 10 days, 11 days, 12 days, 13 days, 14 days, 3 weeks, or 4 weeks. In a specific embodiment, the second period of time at least 1 minute, 2 minutes, 3 minutes, 4 minutes, 5 minutes, 10 minutes, 15 minutes, 20 minutes, 25 minutes, 30 minutes, 45 minutes, 60 minutes, 3 hours, 6 hours, 12 hours, 24 hours, 2 days, 3 days, 4 days, 5 days, 6 days, 7 days, 8 days, 9 days, 10 days, 11 days, 12 days, 13 days, 14 days, 3 weeks, or 4 weeks. In a specific embodiment, the second period of time is at most 1 minute, 2 minutes, 3 minutes, 4 minutes, 5 minutes, 10 minutes, 15 minutes, 20 minutes, 25 minutes, 30 minutes, 45 minutes, 60 minutes, 3 hours, 6 hours, 12 hours, 24 hours, 2 days, 3 days, 4 days, 5 days, 6 days, 7 days, 8 days, 9 days, 10 days, 11 days, 12 days, 13 days, 14 days, 3 weeks, or 4 weeks.

In a specific embodiment, the first pharmaceutically effective dose of the agent is a dose described in Section 5.7. In a specific embodiment, the second pharmaceutically effective dose of the agent is a dose described in Section 5.7.

In some embodiments, the integumental perturbation induces a wound in the skin. In a specific embodiment, the integumentally perturbed skin is wounded. In some such embodiments, the wounded skin is healed by primary intention. In other embodiments, the wounded skin is healed by secondary intention. In yet other embodiments, the wounded skin is healed by tertiary intention. In certain embodiments, the wounded skin is healed more slowly than usually indicated for that kind of wound. This may enhance scarless wound healing and/or prolong the period during which hair growth in the wounded area of skin is promoted. In a specific embodiment, the method further comprises administering a post-perturbation wound healing compound.

In a specific embodiment, the subject is a subject described in Section 5.5.

In a specific embodiment, the method of treatment is a method of treating a condition or disorder of a subject described in Section 5.5.

For any of the treatments described above, in specific embodiments, a particular treatment (e.g., integumental perturbation) can be administered prior to, concurrently with, or subsequent to the administration of a second (or third, or more) treatment (e.g., administration of the first or second pharmaceutically effective dose of the agent). In certain embodiments, the second or third or later treatment comprises treatment with the same active agent, albeit at a different (e.g., in one embodiment, higher) dose.

In one embodiment, one treatment is administered to a subject at reasonably the same time as the other treatment. This method provides that the two administrations are performed within a time frame of less than one minute to about five minutes, or up to about sixty minutes from each other, for example, at the same doctor's visit. In another embodiment, one treatment and another treatment are administered at exactly the same time.

In yet another embodiment, one treatment and the other treatment are administered in a sequence and within a time interval such that the one treatment and the other treatment can act together to provide an increased benefit than if they were administered alone. In another embodiment, the one treatment and the other treatment are administered sufficiently close in time so as to provide the desired outcome. Each can be administered simultaneously or separately, in any appropriate form and by any suitable route. In one embodiment, the one treatment and the other treatment are administered by different routes of administration. In an alternate embodiment, each is administered by the same route of administration. In certain embodiments, the one treatment and the other treatment can be administered at the same or different sites of the subject's body. When administered simultaneously, the one treatment and the other treatment may or may not be administered in a single formulation, a mixture of formulations, or at the same site of administration, or by the same route of administration.

In various embodiments, the one treatment and the other treatment are administered less than 1 hour apart, at about 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In other embodiments, the one treatment and the other treatment are administered 2 to 4 days apart, 4 to 6 days apart, 1 week apart, 1 to 2 weeks apart, 2 to 4 weeks apart, one month apart, 1 to 2 months apart, 2 to 3 months apart, 3 to 4 months apart, 4 to 5 months apart, 6 months apart, 6 months to one year apart, or one year or more apart. In some embodiments, the one treatment and the other treatment are administered in a time frame where both are still active. One skilled in the art would be able to determine such a time frame by determining the half life of each administered component.

In one embodiment, the one treatment and the other treatment are administered within the same patient visit. In one embodiment, the one treatment is administered prior to the administration of the other treatment. In an alternate embodiment, the one treatment is administered subsequent to the administration of the other treatment.

In certain embodiments, the one treatment and the other treatment are cyclically administered to a subject. Cycling treatment involves the administration of one or more treatments once or for a period of time, followed by the administration of the other treatment once or for a period of time, and repeating this sequential administration. The first treatment may be with the one treatment or with the other treatment, depending on the subject's prior treatment history and the intended outcome. Not only does such cycling treatment have the advantages described herein, cycling treatment can also reduce the development of resistance to one or more of the treatments, avoid or reduce the side effects of one of the treatments, and/or improve the efficacy of the treatment. In such embodiments, alternating administration of the one or more treatments may be followed by the administration of another treatment (or vice versa) 1 year later, 6 months later, 3 months later, 1 month later, 3 weeks later, 2 weeks later, 1 week later, 4 to 6 days later, 2 to 4 days later, or 1 to 2 days later, wherein such a cycle may be repeated as many times as desired. In certain embodiments, the one (or more) treatments and the other treatment are alternately administered in a cycle of 3 weeks or less, once every two weeks, once every 10 days or once every week. Such time frames can be extended or reduced depending on properties of the treatment, e.g., whether a controlled release formulation is used, and/or depending on the progress of the treatment course.

In a specific embodiment, an applicator device described herein is suitable for administration of a compound to a subject. Accordingly, provided herein is a method of administering a compound to a subject in need thereof, comprising use of an applicator device described herein. In a specific embodiment, the compound is a compound described in Section 5.6.

(a) Biological Outcomes

In a specific embodiment, a needling device, a needling adaptor, an applicator device, and/or a mobile app described herein are suitable for achieving one or more of the biological outcomes described herein. In a specific embodiment, a needling device described herein is suitable for achieving one or more of the biological outcomes described herein. In a specific embodiment, a needling adaptor described herein is suitable for achieving one or more of the biological outcomes described herein. In a specific embodiment, an applicator device described herein is suitable for achieving one or more of the biological outcomes described herein. In a specific embodiment, a mobile app described herein is suitable for achieving one or more of the biological outcomes described herein. Accordingly, a method of treatment comprising use of one or more of the devices described herein and/or the mobile app described herein achieve one or more of the biological outcomes described herein.

In a specific embodiment, the devices and/or mobile apps described herein are suitable to achieve one or more of the following nonlimiting examples of biological outcomes in a subject on which the devices and/or mobile apps were used: hair growth applications, wrinkle reduction, scar revision, hair removal, tattoo removal, and pigmentation adjustment. Nonlimiting examples of hair growth applications include increasing the amount of hair, increasing hair thickness, increasing hair longevity, inducing hair follicle neogenesis, treating baldness, treating alopecia, promoting hair follicle development and/or activation on an area of the skin of the subject, and/or treatment of a condition described in Section 5.5.

In a specific embodiment, the devices and/or mobile apps described herein are suitable to achieve one or more of the following nonlimiting examples of biological outcomes in a subject on which the devices and/or mobile apps were used: to promote generation of new hair follicles ("follicle neogenesis"); to promote formation of neogenic-like (NL) follicular structures; to promote activation (possibly by reorganization) of existing hair follicles; to promote formation of pre-existing-like (PEL) or pre-existing-like, attached (PELA) follicular structures; to promote development of hair follicles, for example, to promote the growth of terminal hair (in preference to vellus hair); to promote the branching of pre-existing hair follicles (seen as an increased number of hair shafts per pore); to increase the width of hair follicles (thereby promoting growth of an increased shaft width); and/or to delay or prevent follicle senescence.

In a specific embodiment, the devices and/or mobile apps described herein are suitable to achieve one or more of the following nonlimiting examples of biological outcomes in a subject on which the devices and/or mobile apps were used: to promote the growth of hair; to promote growth of vellus hair; to promote the transition of vellus hair to terminal hair; to increase the amount of hair follicles in anagen, to prolong anagen, to shorten telogen, to promote growth of terminal hair; to increase the amount of hair; to increase the thickness of hair; and/or to reduce or prevent hair loss.

In a specific embodiment, the devices and/or mobile apps described herein are suitable to achieve one or more of the following nonlimiting examples of biological outcomes in a subject on which the devices and/or mobile apps were used: to promote the growth of hair in follicular units; to promote growth of vellus hair in follicular units, to promote the transition of vellus hair in follicular units to terminal hair in follicular units; to promote growth of terminal hair in follicular units; to increase the amount of hair in follicular units; to increase the thickness of hair in follicular units; and/or to reduce or prevent hair loss or hair miniaturization in follicular units.

In one embodiment, the biological outcome is growth of hair on the area of skin of a subject. In some embodiments, the biological outcome is an increase in the amount or thickness of hair on a treated area of skin of a subject. In some embodiments, the biological outcome is an increase in the amount of vellus hair on a treated area of skin of a subject. In some embodiments, the biological outcome is an increase in the amount of terminal hair on a treated area of skin of a subject. In some embodiments, the biological outcome is the maintenance of terminal hair growth, i.e. help prevent miniaturization of terminal hairs. In some embodiments, the biological outcome is an increase in the ratio of terminal-to-vellus hair on a treated area of skin of a subject. In some embodiments, the biological outcome is an increase in the amount of anagen hair or an increase in anagen growth on a treated area of skin of a subject. In some embodiments, the biological outcome is an increase in the ratio of anagen-to-telogen hair on a treated area of skin of a subject. In some embodiments, the biological outcome is hair follicle neogenesis in a treated area of skin of a subject. In some embodiments, the biological outcome is an increased number of hair follicles in a treated area of skin of a subject. In some embodiments, the biological outcome is formation of new hair follicles with nonvellus-sized hair shafts (i.e., hair shafts with diameters equal to or greater than 30 microns) in a treated area of skin of a subject. In some embodiments, the biological outcome is an increased number of stimulated and activated hair follicles, such as pre-existing hair follicles, in a treated area of skin of a subject. In some embodiments, the biological outcome is an increased number of pre-existing hair follicles with nonvellus-sized hair shafts in a treated area of skin of a subject. In some embodiments, the biological outcome is the presence and/or increased numbers of neogenic-like (NL) follicular structures, pre-existing-like (PEL), and pre-existing-like, attached (PELA) follicular structures.

Success of a device to achieve one or more of the biological outcomes described herein and/or success of a method of the invention can be measured by, for example: (i) improved overall cosmetic outcome (e.g., using the Visual Analogue Scale (VAS)); (ii) patient assessment of his/her hair growth (e.g., based on questionnaire); (iii) investigator assessment of hair growth in a patient (e.g., based on a rating scale); (iv) patient assessment of his/her hair growth in photographs; (v) investigator assessments of hair growth in patient photographs; (vi) increased hair count (e.g., by measuring new hair growth as an increased number of fibers in an affected area of the skin); (vii) increased hair density; (viii) increased thickness of hair or hair shaft (e.g., based on diameter); (ix) increased hair weight; (x) hair cuttings; (xi) longer hair; (xii) increase in the amount of terminal hair (by, e.g., measuring new hair growth as an increased number of fibers in an affected area of the skin, or increased thickness (e.g., diameter) or length of hair fibers); (xiii) increase in the amount of vellus hair (by, e.g., measuring new hair growth as an increased number of fibers in an affected area of the skin) (e.g., as measured photographically); (xiv) increase in the amount of nonvellus hair, e.g., intermediate or terminal hair; (xv) an increase in the ratio of terminal-to-vellus hair; (xvi) increased number of hair germs; (xvii) increased number of hair follicles (e.g., as evaluated by a skin biopsy); (xviii) increased number of hair follicles at a more mature stage of development; (xix) increased numbers of follicular units with 3 or more hair follicles; (xx) increased hair follicle branching; (xxi) formation of new hair follicles ("hair follicle neogenesis"); (xxii) formation of new hair follicles with vellus-sized hair shafts (i.e., hair shafts with diameters less than 30 microns); (xxiii) formation of new hair follicles with nonvellus-sized hair shafts (i.e., hair shafts with diameters 30 microns or greater); (xxiv) hair follicle regeneration; (xxv) increased activation of existing hair follicles; (xxvi) increased number of hair follicles; (xxvii) increased number of activated hair follicles; (xxviii) increased number of activated pre-existing hair follicles; (xxix) presence or increased numbers of neogenic-like (NL) hair follicles (based on, e.g., examination of a biopsy or by confocal microscope, by assessing number of hair follicles, and/or by assessing morphology of hair follicles compared to baseline or a negative control); (xxx) presence or increased numbers of pre-existing hair follicles (based on, e.g., examination of a biopsy or by confocal microscope, by assessing number of hair follicles, and/or by assessing morphology of hair follicles compared to baseline or a negative control); (xxxi) presence or increased numbers of primitive structures of interest (SOIs), such as neogenic-like (NL), pre-existing-like (PEL), and/or pre-existing-like, attached (PELA) follicular structures (based on, e.g., examination of a biopsy or by confocal microscope, by assessing number of hair follicles, and/or by assessing morphology of hair follicles compared to baseline or a negative control, as described for example in Section 5.8.4 infra); (xxxii) increased number of pre-existing hair follicles with vellus-sized hair shafts in a treated area of skin of a subject; (xxxiii) increased number of neogenic-like hair follicles with vellus-sized hair shafts in a treated area of skin of a subject; (xxxiv) increase in the amount of anagen hair; (xxxv) increase in the amount of telogen hair; (xxxvi) increased proportion of hair follicles in anagen or decreased proportion of hair follicles in telogen (i.e., an increase in the ratio of anagen-to-telogen hair) (based on, e.g., examination of a biopsy or phototrichogram); (xxxvii) increased proliferation of dermal papilla (based on, e.g., examination of a biopsy); and/or (xxxviii) increased recruitment or proliferation of stem cells to the follicle (based on, e.g., examination of a biopsy).

In certain embodiments, the devices described herein are suitable for achieving uniform integumental perturbations. For example, in certain embodiments, the devices described herein are suitable for achieving uniformity in the perforations of the integumental perturbation. In a specific embodiment, uniformity is measured by the variance in perforations per square centimeter. In a specific embodiment, the uniformity is at least +/−1%, at least +/−3%, at least +/−5%, at least +/−10%, at least +/−15%, at least +/−20%, at least +/−30%, at least +/−50%. In a specific embodiment, the uniformity is at most +/−1%, at most +/−3%, at most +/−5%, at most +/−10%, at most +/−15%, at most +/−20%, at most +/−30%, at most +/−50%, at most +/−60%, at most +/−70%, at most +/−80%, or at most 90%.

In certain embodiments, success of treatment is assessed by examination of hair follicles in a treated area of the subject's skin. In certain embodiments, hair follicles are examined histologically, or by determination of the presence or absence of certain markers of hair follicle development or morphology. The area of skin for examination may be obtained by biopsy, such as a punch biopsy; alternatively or in addition, in a less invasive method, the skin may be analyzed directly by, e.g., confocal microscopy or other technique that permit imaging beneath the surface of the skin.

5.5 Subject Populations that May be Treated Using the Needling Device and/or the Applicator Device The devices and/or mobile apps described herein are suitable for use on subjects described herein. Thus, described herein are candidate subjects for treatment with a device and/or one or more methods described herein. In a specific embodiment, the subject is any subject suffering from hair loss, hair thinning, balding, or who has or has had a disease or condition associated therewith, or who wishes to enhance the growth or thickness of hair or prevent hair loss. In a specific embodiment, the subject has a tattoo and wishes to remove or reduce the visibility of the tattoo. In a specific embodiment, the subject has a wrinkle and wishes to remove or reduce the visibility of the wrinkle. In a specific embodiment, the subject has a scar and wishes to remove or reduce the visibility of the scar. In a specific embodiment, the subject has an altered pigmentation of an area of skin as compared to a control area of skin on the subject, and wishes to remove or reduce the visibility of the altered pigmentation.

The subject may be any subject, preferably a human subject, including male, female, intermediate/ambiguous (e.g., XO), and transsexual subjects. In certain embodiments, the subject is a human adolescent. In certain embodiments, the subject is undergoing puberty. In certain embodiments, the subject is a middle-aged adult. In certain embodiments, the subject is a premenopausal adult. In certain embodiments, the subject is undergoing menopause. In certain embodiments, the subject is elderly. In certain embodiments, the subject is a human of 1 year old or less, 2 years old or less, 2 years old, 5 years old, 5 to 10 years old, 10 to 15 years old, e.g., 12 years old, 15 to 20 years old, 20 to 25 years old, 25 to 30 years old, 30 years old or older, 30 to 35 years old, 35 years old or older, 35 to 40 years old, 40 years old or older, 40 to 45 years old, 45 to 50 years old, 50 years old or older, 50 to 55 years old, 55 to 60 years old, 60 years old or older, 60 to 65 years old, e.g., 65 years old, 65 to 70 years old, 70 to 75 years old, 75 to 80 years old, 80 to 85 years old, 85 to 90 years old, 90 to 95 years old or 95 years old or older. In some embodiments, the subject is a male 20 to 50 years old. In some embodiments, the subject is a male 20 to 60 years old. In some embodiments, the subject is a male 30 to 60 years old. In some embodiments, the subject is a male 40 to 60 years old. In some embodiments, the subject is a male or female 12 to 40 years old. In some embodiments, the subject is not a female subject. In some embodiments, the subject is not pregnant or expecting to become pregnant. In some embodiments, the subject is not a pregnant female in the first trimester of pregnancy. In some embodiments, the subject is not breastfeeding.

The subject may have a disease or disorder of balding or hair loss (including hair thinning), such as forms of nonscarring (noncicatricial) alopecia, such as androgenetic alopecia (AGA), including male-patterned hair loss (MPHL) or female-patterned hair loss (FPHL) (e.g., thinning of the hair, i.e., diffuse hair loss in the frontal/parietal scalp), or any other form of hair loss caused by androgens, toxic alopecia, alopecia areata (including alopecia universalis), scarring (cicatricial) alopecia, pathologic alopecia (caused by, e.g., medication, trauma stress, autoimmune diseases, malnutrition, or endocrine dysfunction), trichotillomania, a form of hypotrichosis, such as congenital hypotrichosis, or lichen planopilaris, or any other condition of hair loss or balding known in the art or described infra.

In some embodiments, the subject has hair loss caused by a genetic or hereditary disease or disorder, such as androgenetic alopecia.

In some embodiments, the subject has hair loss caused by anagen effluvium, such as what occurs during chemotherapy (with, e.g., 5-fluorouracil, methotrexate, cyclophosphamide, vincristine). In addition to chemotherapy drugs, anagen effluvium can be caused by other toxins, radiation exposure (including radiation overdose), endocrine diseases, trauma, pressure, and certain diseases, such as alopecia areata (an autoimmune disease that attacks anagen follicles.)

In some embodiments, the subject has hair loss caused by telogen effluvium. Telogen effluvium is caused frequently by drugs like lithium and other drugs like valproic acid and carbamazepine. In addition to psychiatric drugs, telogen effluvium can be induced by childbirth, traction, febrile illnesses, surgery, stress, or poor nutrition. (See, Mercke et al., 2000, Ann. Clin. Psych. 12:35-42).

In some embodiments, the subject has hair loss caused by or associated with medication, such as chemotherapy (e.g., anti-cancer therapy or cytotoxic drugs), thallium compounds, vitamins (e.g., vitamin A), retinoids, anti-viral therapy, or psychological therapy, radiation (such as the banding pattern of scalp hair loss that may be caused by radiation overdose), trauma, endocrine dysfunction, surgery, physical trauma, x-ray atrophy, burning or other injury or wound, stress, aging, an autoimmune disease or disorder, malnutrition, an infection (such as, e.g., a fungal, viral, or bacterial infection, including chronic deep bacterial or fungal infections), dermatitis, psoriasis, eczema, pregnancy, allergy, a severe illness (e.g., scarlet fever), myxedema, hypopituitarism, early syphilis, discoid lupus erythematosus, cutaneous lupus erythematosus, lichen planus, deep factitial ulcer, granuloma (e.g., sarcoidosis, syphilitic gummas, TB), inflamed tinea capitis (kerion, favus), a slow-growing tumor of the scalp or other skin tumor, or any other disease or disorder associated with or that causes balding or hair loss known in the art or described infra.

In some embodiments, the subject has hair thinning, or "shock loss," or a bald patch caused by prior use as a source of tissue or follicles for hair transplantation or follicular unit transplantation.

In some embodiments, a candidate subject is a subject who wishes to enhance hair growth, for example, to have more hair, faster-growing hair, longer hair, and/or thicker hair. In some embodiments, the candidate is a subject who wishes to increase hair pigmentation. In some embodiments, the subject is not affected by a condition of excessive hair loss.

As used herein, the terms "patient" and "subject" are used interchangeably.

5.6 Agents

Also provided herein are agents that may be administered via a device provided herein, used in combination with a device described herein, and/or used in a method described herein. In a specific embodiment, the agent is formulated in a pharmaceutical composition. In a specific embodiment, the pharmaceutical composition comprises the agent and a pharmaceutically acceptable carrier or excipient. Pharmaceutically acceptable carriers and excipients are known in the art.

In one aspect, the agent is an agent that promotes hair growth. For example, hair growth-promoting agents for use, alone or in combination, in accordance with this aspect include but are not limited to: agents affecting prostaglandins, such as Prostaglandin F2a analogs, e.g. latanoprost (trade name Xalatan), travoprost (trade name Travatan), tafluprost, unoprostone, dinoprost (trade name Prostin F2 Alpha), AS604872, BOL303259X, PF3187207, carboprost (trade name Hemabate); Prostamides, e.g., bimatoprost (trade names Latisse, Lumigan); Prostanoid receptor agonists, e.g. fluprostenol; Prostaglandin D2 receptor antagonists, e.g. laropiprant, AM211; Prostglandin E2 analogs, e.g. sulprostone; and EP 2 receptor agonists, e.g. butaprost; 5α-reductase inhibitors, such as, e.g., finasteride, dutasteride, turosteride, bexlosteride, izonsteride, epristeride, epigallocatechin, Fluridil (Sovak et al, Dermatol Surg. 2002; 28(8):678-685), RU 58841 (Pan et al. Endocrine. 1998; 9(1):39-43), N,N-diethyl-4-methyl-3-oxo-4-aza-5 alpha-androstane-17 beta-carboxamide (Rittmaster et al., J Clin Endocrinol Metab. 1987; 65(1):188-193), MK-386, azelaic acid, FCE 28260, SKF 105,111; Minoxidil; ATP-sensitive potassium channel openers, e.g. diazoxide; and the hair growth-promoting agents described herein or otherwise known in the art, such as, e.g., kopexil (for example, the product Keranique™), CaCl2, botilinum toxin A, adenosine, ketoconazole, DoxoRx, Docetaxel, FK506, GP11046, GP11511, LGD 1331, ICX-TRC, MTS-01, NEOSH101, HYG-102440, HYG-410, HYG-420, HYG-430, HYG-440, spironolactone, CB-03-01, RK-023, Abatacept, Viviscal®, MorrF, ASC-J9, NP-619, AS101, Metron-F-1, PSK 3841, Targretin (e.g., 1% gel), MedinGel, PF3187207, BOL303259X, AS604872, THG11331, PF-277343, PF-3004459, Raptiva, caffeine, and coffee. Other hair-growth promoting agents include arginine, isoleucine, leucine, lysine, methionine, phenylalanine, threonine, tryptophan, valine, gamma linoleic acid and polyphenol catechins, copper peptides. Other hair-growth promoting agents that can be formulated as a hair wash tonic could include but are not limited to, jojoba oil, extract of apple, saw palmetto, emu oil, beta carotene and green tea. In another aspect, the applicators may also be used in combination with drugs for alopecia being developed by SWITCH Biotech LLC. In addition, other agents include compounds identified by the following company and company ID, Actelion ACT-129968 (setipiprant), Actimis AP768, Amira AM211, Amira AM461, Amgen AMG853, Array BiPharma ARRY-502, AstraZeneca AZD1981, AstraZeneca AZD8075, AstraZeneca AZD5985, Merck MK-7246, Novartis QAV680, Oxagen 00000459, Ocagen 00002417, Pulmagen ADC3680B, Shionogi S-555739, BBI-5000, SM04554, and KYTH105 (setipiprant). Further, additional agents include proteasome inhibitors such as lactacystin, a peptidyl aldehyde, or pentoxyfilline (PTX).

In one aspect, the agent is an agent that is useful in reducing wrinkles. Agents useful in the reduction of wrinkles are known in the art. Nonlimiting examples of agents useful in reducing wrinkles include immune response modifier (IRM) compounds such as idazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, a thiazolonaphthyridine amine, or a combination thereof.

In one aspect, the agent is an agent that is useful in scar revision. Agents useful in scar revision are known in the art. Nonlimiting examples of agents useful in scar revision include immune response modifier (IRM) compounds such as imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, a thiazolonaphthyridine amine, or a combination thereof.

In one aspect, the agent is an agent that is useful in hair removal. Agents useful in hair removal are known in the art. Nonlimiting examples of agents useful in hair removal include ntiandrogens, androgen inhibitors, chromaphores, photosensitizers, enzymes, phosphonic acid derivatives, matrix metalloproteinases, and combinations thereof.

In one aspect, the agent is an agent that is useful in tattoo removal. Agents useful in the tattoo removal are known in the art. Nonlimiting examples of agents useful in tattoo removal include immune response modifier (IRM) compounds such as compounds with antiviral and/or anti-tumor activity, compounds that induce the production and secretion of cytokines, purine derivatives, imidazoquinoline amid derivatives, imidazopyridine derivatives, benzimidazole derivatives, derivatives of a 4-aminopyrimidine fused to a five membered nitrogen containing heterocyclic ring, certain 3-beta-D-ribofuranosylthiazolo[4,5-d]pyrimidine derivatives, and aminoalkyl glucosaminide phosphates, 5% imiquimod (1-(2-methylpropyl)-1H-imidazo[4,5-c]quinolin-4-amin) cream.

In one aspect, the agent is an agent that is useful in pigmentation. Agents useful in pigmentation are known in the art. Nonlimiting examples of agents useful in pigmentation include a vitamin C derivative, niacinamide, cucumber extract, lemon extract, and S-acyl glutathione derivatives.

In another aspect, the agent is a topical anesthetic.

As used herein, the terms "compound" and "agent" are used interchangeably.

5.6.1 Hair Growth-Promoting Agents

In a specific embodiment, a compound described herein is a hair growth-promoting agent.

The integumental perturbation methods described in Section 5.1 supra, alone or in combination with a post-perturbation treatment described in Section 5.2 supra, may be used in combination treatments with hair growth-promoting agents, and optionally in combination with the treatments described in Section 5.4 below. In some embodiments, a hair growth-promoting agent described herein promotes hair follicle development and growth, resulting in the transition of vellus hair on an area of the skin to non-vellus, e.g., intermediate or terminal, hair. In some embodiments, a hair growth-promoting agent described herein acts synergistically with the integumental perturbation method to promote hair growth. The effect that each treatment offers could be an additive or synergistic improvement, or a combination of two different biologically defined effects, to achieve the desired end result.

In some embodiments, the hair growth-promoting agent is a treatment that promotes hair growth and/or treats a disease or condition associated with excessive hair loss. Any treatment that promotes hair growth and/or treats a disease or condition associated with excessive hair loss that is known in the art or yet to be developed is contemplated for use in accordance with these embodiments.

In some embodiments, the hair growth-promoting agent treatment comprises treatment with one or more channel openers (e.g., potassium channel opener, e.g., an ATP-sensitive potassium channel (KATP opener), or an activator of such a channel), such as, e.g., minoxidil (e.g., marketed as Rogaine or Regaine), diazoxide, or phenytoin. In a particular embodiment, the hair growth-promoting agent treatment comprises treatment with minoxidil. Commonly used dosage forms of minoxidil that may be used in accordance with these embodiments are topical solutions comprising 2% minoxidil or 5% minoxidil, for example, topical minoxidil foam 5%.

In some embodiments, the hair growth-promoting agent treatment comprises treatment with one or more 5α-reductase inhibitors. Non-limiting examples of 5α-reductase inhibitors include finasteride, dutasteride (e.g., Avodart), turosteride, bexlosteride, izonsteride, epristeride, epigallocatechin, MK-386, azelaic acid, FCE 28260, and SKF 105,111. Commonly used dosage forms of finasteride that may be used in such treatments are, for example, oral finasteride at 1 mg/day. See, e.g., Physicians' Desk Reference, 2009, 63rd ed., Montvale, N.J.: Physicians' Desk Reference Inc., entries for Propecia® and Proscar® at pages 2095-2099 and 2102-2106, respectively, which are incorporated herein by reference in their entireties.

In some embodiments, the hair growth-promoting agent treatment comprises treatment with one or more antiandrogens, such as, e.g., finasteride (e.g., marketed as Propecia or Proscar), ketoconazole, fluconazole, spironolactone, flutamide, diazoxide, 17-alpha-hydroxyprogesterone, 11-alpha-hydroxyprogesterone, ketoconazole, RU58841, dutasteride (marketed as Avodart), fluridil, or QLT-7704, an antiandrogen oligonucleotide, or others described in Poulos & Mirmirani, 2005, Expert Opin. Investig. Drugs 14:177-184, the contents of which is incorporated herein by reference.

In some embodiments, the hair growth-promoting agent treatment comprises treatment with one or more prostaglandin F2α analogs, prostaglandin analogs, or prostaglandins. Non-limiting examples of prostaglandin F2α analogs include bimatoprost (e.g., Latisse, Lumigan), latanoprost (trade name Xalatan), travoprost (trade name Travatan), tafluprost, unoprostone, dinoprost (trade name Prostin F2 Alpha), AS604872, BOL303259X, PF3187207, carboprost (trade name Hemabate). For exemplary prostaglandin F2α analogs, as well as formulations, dosages, and treatment regimens, for use in accordance with the methods described herein, see, e.g., U.S. Pat. Nos. 8,017,655, 5,688,819, 6,403,649, 5,510,383, 5,631,287, 5,849,792, 5,889,052, 6,011,062, 7,163,959, 5,296,504, 5,422,368, 6,429,226, and 6,946,120, the entire contents of each of which is incorporated herein by reference in its entirety. See also, with respect to latanoprost, Uno et al., 2002, Acta Derm Venereol 82:7-12, the contents of which is incorporated herein by reference in its entirety.

In some embodiments, the hair growth-promoting agent treatment comprises treatment with one or more of the following hair growth-promoting agents: kopexil (for example, the product Keranique™), CaCl2, botilunum toxin A, adenosine, ketoconazole, DoxoRx, Docetaxel, FK506, GP11046, GP11511, LGD 1331, ICX-TRC, MTS-01, NEOSH101, HYG-102440, HYG-410, HYG-420, HYG-430, HYG-440, spironolactone, CB-03-01, RK-023, Abatacept, Viviscal®, MorrF, ASC-J9, NP-619, AS101, Metron-F-1, PSK 3841, Targretin (e.g., 1% gel), MedinGel, PF3187207, BOL303259X, AS604872, THG11331, PF-277343, PF-3004459, Raptiva, caffeine, an coffee. In some embodiments, the hair growth-promoting agent treatment comprises drugs for alopecia being developed by SWITCH Biotech LLC.

In some embodiments, the hair growth-promoting agent treatment comprises treatment with one or more of the following: herbs (such as, e.g., saw palmetto, *Glycine soja, Panax ginseng, Castanea Sativa, Arnica Montana, Hedera Helix Geranium Maculatum*), triamcinolone acetonide (e.g., suspension of 2.5 to 5 mg/ml for injection), a topical irritant (e.g., anthralin) or sensitizer (e.g., squaric acid dibutyl ester [SADBE] or diphenyl cyclopropenone [DPCP]), clomipramine, unsaturated fatty acids (e.g., gamma linolenic acid), a fatty acid derivative, thickeners (such as, e.g., carbomer, glycol distearate, cetearyl alcohol), a hair loss concealer, niacin, nicotinate esters and salts, adenosine, and methionine. In some embodiments, the hair growth-promoting agent treatment comprises treatment with nitroxide spin labels (e.g., TEMPO and TEMPOL). See U.S. Pat. No. 5,714,482, which is incorporated herein by reference.

In some embodiments, the hair growth-promoting agent treatment comprises treatment with an androgen receptor inhibitor, which have been shown to be useful for stimulating scalp hair growth (Hu L Y, et al., 2007, Bioorg Med Chem Lett. 2007 17:5983-5988).

In some embodiments, the hair growth-promoting agent treatment comprises treatment with a copper peptide(s), preferably applied topically, or another compound with superoxide dismutation activity. In some embodiments, the hair growth-promoting agent treatment comprises treatment with an agent that increases nitric oxide production (e.g., arginine, citrulline, nitroglycerin, amyl nitrite, or sildenafil (Viagra)). In preferred embodiments, such compounds are administered further in combination with a catalase or catalase mimetic, or other antioxidant or free radical scavenger.

In some embodiments, the hair growth-promoting agent treatment comprises treatment with a compound that mobilizes bone marrow—derived stem cells (e.g., growth factors such as G-CSF and/or chemical agents such as plerixafor (Mozobil®)); and/or that regulates the differentiation of these stem cells into gender-specific specialized human hair follicles (e.g., using agents such as finasteride, fluconazole, spironolactone, flutamide, diazoxide, 11-alpha-hydroxyprogesterone, ketoconazole, RU58841, dutasteride, fluridil, or QLT-7704, an antiandrogen oligonucleotide, cyoctol, topical progesterone, topical estrogen, cyproterone acetate, ru58841, combination 5α-reductase inhibitors, oral contraceptive pills, and others in Poulos & Mirmirani, 2005, Expert Opin. Investig. Drugs 14:177-184, incorporated herein by reference, or any other antiestrogen, an estrogen, or estrogen-like drug (alone or in combination with agents that increase stem cell plasticity; e.g., such as valproate), etc., known in the art), that can result in, e.g., the appearance of specialized follicles having features that are different from natural follicles in the target location of skin.

In some embodiments, the hair growth-promoting agent treatment comprises treatment with one or more agents that counteract age-related hair thinning and/or hair follicle cell senescence (also referred to herein as "anti-senescence agents") for example, anti-oxidants such as glutathione, ascorbic acid, tocopherol, uric acid, or polyphenol antioxidants); inhibitors of reactive oxygen species (ROS) generation, such as superoxide dismutase inhibitors; stimulators of ROS breakdown, such as selenium; mTOR inhibitors, such as rapamycin; or sirtuins or activators thereof, such as resveratrol, or other SIRT1, SIRT3 activators, or nicotinamide inhibitors.

In some embodiments, the hair growth-promoting agent treatment comprises treatment with one or more agents that induce an immune response or cause inflammation, such as, e.g., tetanus toxoid, topical non-specific irritants (anthralin), or sensitizers (squaric acid dibutyl ester [SADBE] and diphenyl cyclopropenone [DPCP]). While not intending to be bound by any theory, it is thought that by contacting these agents to the skin, lymphocytes and hair follicle stem cells may be recruited to skin. In some embodiments, the hair growth-promoting agent treatment comprises treatment with a chemical or mechanical (such as those discussed infra) treatment that induces an inflammatory process in the skin. While not intending to be bound by any theory, inducing inflammation in the site where hair growth is desired helps to recruit stem cells to the tissues that drive the formation of new follicles.

In some embodiments, the hair growth-promoting agent treatment comprises treatment with an antiapoptotic compound. In one embodiment, the antiapoptotic compound is not a Wnt or a Wnt agonist.

In some embodiments, the hair growth-promoting agent treatment comprises treatment with stem cell therapy, hair cloning, hair transplantation, scalp massage, a skin graft, hair plugs, follicular unit extraction, or any surgical procedure aimed at hair restoration.

In certain embodiments, a hair growth-promoting agent described herein may be used at a dosage or in a range of dosages known in the art for that agent (e.g., as made available on a package insert or in the Physicians' Desk Reference). In other embodiments the regular dosage of the hair growth-promoting agent is adjusted to optimize a combination treatment (e.g., integumental perturbation or treatment with another active ingredient) described herein. For example, the regular dosage may be increased or decreased as directed by the physician. For example, a lower dosage may be used over a shorter duration owing to the synergistic effect of combination with another treatment described herein.

In certain embodiments, the hair growth-promoting agent may be used in its commercially available form. In other embodiments, the form of the hair growth-promoting agent is adjusted to optimize a combination treatment (e.g., integumental perturbation or treatment with another active ingredient) described herein. In a particular embodiment, the hair growth-promoting agent is formulated as a different salt form than that which is commercially available. In a particular embodiment, the hair growth-promoting agent is formulated for topical administration, e.g., by incorporation into a pharmaceutical composition for post-perturbation treatment described in Section 5.2 infra.

In some embodiments, the hair growth-promoting agent enhances conversion of vellus hair to non-vellus hair. In a particular embodiment, the hair growth-promoting agent enhances conversion of vellus hair to terminal hair. Exemplary hair growth-promoting agents that promote conversion of vellus to non-vellus hair that may be used in accordance with these embodiments are prostaglandin F2α analogs (in one aspect, latanoprost), minoxidil, etc. In some embodiments, the hair growth-promoting agent enhances conversion of telogen hair to anagen hair. In a particular embodiment, the hair growth-promoting agent enhances conversion of telogen hair to anagen hair. Exemplary hair growth-promoting agents that promote conversion of telogen to anagen hair that may be used in accordance with these embodiments are prostaglandin F2α analogs (in one aspect, latanoprost), minoxidil, etc.

In some embodiments, the hair growth-promoting agent treatment comprises treatment with an antiandrogen (e.g., a 5α-reductase inhibitor) and a channel opener (e.g., minoxidil). In one such embodiment, a 5α-reductase inhibitor is administered in combination with minoxidil. In one such embodiment, finasteride is administered in combination with minoxidil. In some embodiments, the hair growth-promoting agent treatment comprises treatment with a prostaglandin F2α or prostamide analog (e.g., latanoprost, bimatoprost, etc.) in combination with a channel opener (e.g., minoxidil). In one such embodiment, a prostaglandin F2α or prostamide analog is administered in combination with minoxidil. In one such embodiment, latanoprost is administered in combination with minoxidil. In another such embodiment, bimatoprost is administered in combination with minoxidil.

In some embodiments, a treatment described herein for promoting hair growth in a female subject does not comprise finasteride or ketoconazole. In some embodiments, a treatment described herein for promoting hair growth in a pregnant female subject is not finasteride or ketoconazole.

In some embodiments a treatment described herein for promoting hair growth does not comprise minoxidil. In some embodiments a treatment described herein for promoting hair growth does not comprise finasteride. In some embodiments a treatment described herein for promoting hair growth does not comprise dutasteride. In some embodiments a treatment described herein for promoting hair growth does not comprise fluridil. In some embodiments a treatment described herein for promoting hair growth does not comprise spironolactone. In some embodiments a treatment described herein for promoting hair growth does not comprise cyproterone acetate. In some embodiments a treatment described herein for promoting hair growth does not comprise bicalutamide. In some embodiments a treatment described herein for promoting hair growth does not comprise flutamide. In some embodiments a treatment described herein for promoting hair growth does not comprise nilutamide. In some embodiments a treatment described herein for promoting hair growth does not comprise an inhibitor of an androgen receptor. In some embodiments a treatment described herein for promoting hair growth does not comprise an androgen antagonist. In some embodiments a treatment described herein for promoting hair growth does not comprise an anti-androgen.

5.7 Doses

The dose of the agent used in accordance with the devices and/or methods provided herein should be adjusted so that maximum benefit is achieved while reducing potential side effects.

In some embodiments, the target concentration of the agent should be maintained in the skin or blood, and preferably the skin, for at least 1 day; at least 2 days; at least 3 days; at least 4 days; at least 5 days; at least 6 days; at least 7 days; at least 8 days; at least 9 days; at least 10 days; at least 11 days; at least 12 days; at least 13 days; at least 14 days; at least 15 days; at least 16 days; at least 19 days; or at least 21 days; and, in certain embodiments, not more than 28 days. In certain embodiments, the target concentration of the agent is maintained in skin or blood, and preferably the skin, for 1 month or more, 2 months or more, 3 months or more, 3 to 6 months or more, or 6 to 12 months or more. This can be accomplished using, e.g., repeated applications of the agent or a single application of a sustained release or extended release agent formulation. For example, a modified release form can be used to achieve the target concentration of the agent for shorter maintenance periods (i.e., for at least 1, 2 or 3 days). Maintenance periods longer than 3 days may require repeated application of the agent treatments. In some embodiments, it is preferable to allow the concentration of the agent to decline between dosages.

Care should be taken to avoid toxicity. In this regard, a dosage should be chosen that maximizes efficacy while minimizing toxicity. Patients should be monitored for toxic side effects according to standard clinical practice. In some embodiments, agent doses should be adjusted on the basis of the blood concentration (serum or plasma) drawn (by convention) 12 or 24 hours after the last dose of the agent. It may be possible to predict dosage requirements for an individual patient based on the results of administration of a single test dose, followed by a skin and/or blood sample assay (plasma or serum) at the peak concentration time; followed by blood sample assays to monitor toxicity at the 12 hour or 24 hour trough concentration; and 24 or 48 or 96 hours later (when hair growth-promoting agent is generally eliminated) which serves as the control value. Once the dose is established for a patient, routine monitoring for toxicity is recommended. It may also be possible to predict who will respond better to Minoxidil by checking levels of minoxidil sulfotransferase (Buhl et al., J Invest Dermatol. 1990; 95(5): 553-557).

In another embodiment, the dose of the agent is a dose sufficient to achieve one or more of the biological outcomes described in Section 5.4.5(a).

5.8 Kits and Device Combinations

In an example, the devices described above may each be packaged and sold separately, packaged separately and sold in another packaging together, or packaged and sold together.

For example, a needling device may be sold in a package including a needling device, an adaptor sheath with a rectangular needing array, and a charging station. Also, the needling device may be sold without the charging station. Also, the needling device may be sold with a one or more additional needling adaptors or sheaths having a different needling array such as a circular needling array for providing a precision tip.

In another example, any embodiment of needling devices and components as describe above may be sold with a fluid or drug applicator. The drug applicator may include the applicator device, one or more massage heads, one or more massage cartridges, and an applicator charging station.

In a further example, the needling device and applicator are sold together as a system with a needling device, a needling sheath adaptor, a fluid applicator, a fluid cartridge, one or more charging stations, and a software or a downloadable mobile app for controlling each of the devices together and/or separately for procedures involving needling, massaging, and fluid dispensing cycles, separately or in combination.

It will be appreciated by those skilled in the art that changes could be made to the embodiments described above without departing from the broad inventive concept thereof. It is understood, therefore, that the invention disclosed herein is not limited to the particular embodiments disclosed, but it is intended to cover modifications within the spirit and scope of the present invention as defined by the appended claims.

The invention claimed is:

1. A needling device, comprising:
a sheath assembly comprising a needle array on a needle holder that is secured to a drive shaft interface; and
a main unit comprising a motor for driving the needle array,
wherein the main unit is configured to be fully encapsulated within the sheath assembly so that all parts of the main unit are protected from an outside environment, characterized in that internal components of the sheath assembly include a bio-barrier as an additional layer of protection and sealing of the main unit, wherein the bio-barrier is attached about the needle holder and is configured to move with the needle holder, and
the sheath assembly further comprises a sheath body and a sheath cap, wherein the sheath cap is separable from the sheath body, and wherein the main unit is reversibly removable from the sheath body when the sheath body is separated from the sheath cap.

2. The needling device of claim 1, wherein the needle array is driven axially by the motor in a direction that is parallel with a longitudinal axis of the needling device along which the needling device extends.

3. The needling device of claim 1, wherein the needling device is adapted to perform needling of a human scalp for promoting hair growth, of skin tissue for skin repair, or of scar tissue for scar removal.

4. The needling of claim 3, wherein the needling device is adapted to treat baldness or chemotherapy-induced alopecia.

5. The needling device of claim 1, wherein the needling device is adapted to disrupt a basal or suprabasal epidermal layer of a human skin.

6. The needling device of claim 1, wherein the sheath assembly keeps the main unit substantially germ free, sterile, or free from biological contamination as a result of fully encapsulating the main unit.

7. The needling device of claim 6, wherein the bio-barrier within the sheath assembly is to prevent contamination from a subject's blood.

8. The needling device of claim 1, wherein the sheath cap is configured to control a depth of the needle array without removing the main unit from within the sheath assembly.

9. The needling device of claim 8, wherein the depth of the needle array ranges from a depth extending beyond an end of the sheath assembly and towards a subject's skin to a depth that is fully retracted within the sheath assembly and away from the subject's skin.

10. The needling device of claim 8, wherein the main unit further comprises a main unit cap and the sheath cap is configured to rotate the main unit cap.

11. The needling device of claim 1, further comprising one or more buttons for controlling the needling device positioned on a surface of the sheath assembly without removing the main unit from within the sheath assembly.

12. The needling device of claim 11, wherein the one or more buttons are configured to control one or more of a depth of the needle array, a speed of needling, a power of the needling device, and a LED for illumination of a perturbation area.

13. The needling device of claim 1, wherein the main unit further comprises a main unit cap and a drive shuttle chassis for controlling a depth of the needle array, the sheath assembly further comprising the sheath cap, and in response to a user rotating the sheath cap, the main unit cap is rotated, the drive shuttle chassis is axially displaced, and the depth of the needle array is adjusted.

14. The needling device of claim 13, wherein the needling device eliminates dragging of needles in a subject's skin.

15. The needling device of claim 1, wherein the needle array comprises a rectangular base and two substantially parallel rows of needles on the rectangular base so that a speed of needling is increased and a number of needling strokes is reduced.

16. The needling device of claim 1, wherein the drive shaft interface is configured to contact the needle array for controlling needling.

17. The needling device of claim 16, wherein the main unit further comprises a drive cam and wherein the drive cam is attached to the drive shaft interface for actively controlling a positive and return motion of the needle array, the positive motion being towards a skin of a subject and the return motion being away from the skin of the subject and towards the needling device.

18. The needling device of claim 1, wherein the main unit further comprises a drive cam that is attached to the motor for controlling a positive and return motion of needling, the positive motion being towards a skin of a subject and the return motion being away from the skin of the subject and towards the needling device.

19. The needling device of claim 1, further comprising a light for illuminating a target region on a subject's skin.

20. A method of using a needling device for stimulating hair growth, comprising:
opening a sheath assembly, the sheath assembly comprising a needle array on a needle holder that is secured to a drive shaft interface, the sheath assembly further comprising a sheath body and a sheath cap, wherein the sheath cap is separable from the sheath body, and wherein a main unit is reversibly removable from the sheath body when the sheath body is separated from the sheath cap;
placing the main unit within the sheath assembly, the main unit comprising a motor for driving the needle array;
closing the sheath assembly to fully encapsulate the main unit within the sheath assembly so that all parts of the main unit are protected from an outside environment, characterized in that internal components of the sheath assembly include a bio-barrier as an additional layer of protection and sealing of the main unit, wherein the bio-barrier is attached about the needle holder and is configured to move with the needle holder; and
powering on the needling device.

* * * * *